United States Patent
Barany et al.

(10) Patent No.: US 9,598,728 B2
(45) Date of Patent: Mar. 21, 2017

(54) METHOD FOR RELATIVE QUANTIFICATION OF NUCLEIC ACID SEQUENCE, EXPRESSION, OR COPY CHANGES, USING COMBINED NUCLEASE, LIGATION, AND POLYMERASE REACTIONS

(71) Applicant: CORNELL UNIVERSITY, Ithaca, NY (US)

(72) Inventors: Francis Barany, New York, NY (US); Eugene Spier, Los Altos, CA (US); Alain Mir, Redwood City, CA (US)

(73) Assignee: Cornell University, Ithaca, NY (US)

( * ) Notice: Subject to any disclaimer, the term of this patent is extended or adjusted under 35 U.S.C. 154(b) by 167 days.

(21) Appl. No.: 14/378,268

(22) PCT Filed: Feb. 14, 2013

(86) PCT No.: PCT/US2013/026180
§ 371 (c)(1),
(2) Date: Aug. 12, 2014

(87) PCT Pub. No.: WO2013/123220
PCT Pub. Date: Aug. 22, 2013

(65) Prior Publication Data
US 2015/0038336 A1    Feb. 5, 2015

Related U.S. Application Data

(60) Provisional application No. 61/598,343, filed on Feb. 14, 2012, provisional application No. 61/605,057, (Continued)

(51) Int. Cl.
*C12Q 1/68* (2006.01)

(52) U.S. Cl.
CPC .......... *C12Q 1/6853* (2013.01); *C12Q 1/6806* (2013.01); *C12Q 1/6855* (2013.01); (Continued)

(58) Field of Classification Search
None
See application file for complete search history.

(56) References Cited

U.S. PATENT DOCUMENTS 5,573,907 A    11/1996   Carrino et al.
5,854,033 A *   12/1998   Lizardi ............... C12Q 1/6804
                                                                      435/6.12

(Continued)

FOREIGN PATENT DOCUMENTS

WO      2004/053105 A2    6/2004

OTHER PUBLICATIONS

Extended European Search Report for EP 13749841.6 dated Nov. 10, 2015.
(Continued)

*Primary Examiner* — Joseph G Dauner
(74) *Attorney, Agent, or Firm* — LeClairyRyan, a Professional Corporation

(57) ABSTRACT

The present invention is directed to methods for identifying the presence of one or more target nucleotide sequences in a sample that involve a nuclease-ligation reaction. In some embodiments, the ligation products formed in the nuclease-ligation process of the present invention are subsequently amplified using a polymerase chain reaction. The ligated product sequences or extension products thereof are detected, and the presence of one or more target nucleotide sequences in the sample is identified based on the detection.

14 Claims, 17 Drawing Sheets

Related U.S. Application Data filed on Feb. 29, 2012, provisional application No. 61/644,405, filed on May 8, 2012.

(52) U.S. Cl.
CPC ..... *C12Q 1/6851* (2013.01); *C12Q 2525/301* (2013.01); *C12Q 2533/107* (2013.01)

(56) References Cited

U.S. PATENT DOCUMENTS

| | | | |
|---|---|---|---|
| 6,270,967 | B1 | 8/2001 | Whitcombe et al. |
| 7,601,821 | B2 | 10/2009 | Andersen et al. |
| 2002/0137036 | A1 | 9/2002 | Sorge et al. |
| 2005/0142543 | A1 | 6/2005 | Barany et al. |
| 2005/0239089 | A1 | 10/2005 | Johnson et al. |
| 2006/0110748 | A1* | 5/2006 | Sorge .............. C12Q 1/6844 435/6.1 |
| 2006/0234252 | A1 | 10/2006 | Andersen |
| 2007/0092880 | A1 | 4/2007 | Crothers et al. |
| 2007/0275375 | A1 | 11/2007 | Van Eijk |
| 2009/0156412 | A1 | 6/2009 | Boyce, IV et al. |
| 2011/0212846 | A1 | 9/2011 | Spier |

OTHER PUBLICATIONS

Haqqi, "Direct Ligation of PCR Products for Cloning and Sequencing," Nucleic Acids Research 20(23):6427 (1992).
International Search Report and Written Opinion for corresponding application No. PCT/US13/26180 (mailed May 3, 2013).
Partial European Search Report for corresponding EP 13749841.6 (Jul. 17, 2015).
Dobosy et al., "RNase H-Dependent PCR (rhPCR): Improved Specificity and Single Nucleotide Polymorphism Detection Using Blocked Cleavable Primers," BMC Biotechnol. 11:80 (2011).
Lyamichev et al., "Comparison of the 5' Nuclease Activities of Taq DNA Polymerase and Its Isolated Nuclease Domain," Proc. Nat'l. Acad. Sci. U.S.A. 96:6143-6148 (1999).
Third Office Action for CN201380018363.1 dated Sep. 5, 2016.
Notice of Reasons for Rejection JP2014-557776 dated Nov. 24, 2016.
Voelkerding et al., "Next-Generation Sequencing: From Basic Research to Diagnostics," Clinical Chemistry 55(4):641-658 (2009).
Chan, E., "Advances in Sequencing Technology," Mutation Research 573:13-40 (2005).
Schuster, S., "Next-Generation Sequencing Transforms Today's Biology," Nature Methods 5(1):16-18 (2008).

* cited by examiner

METHOD FOR RELATIVE QUANTIFICATION OF NUCLEIC ACID SEQUENCE, EXPRESSION, OR COPY CHANGES, USING COMBINED NUCLEASE, LIGATION, AND POLYMERASE REACTIONS

This application is a national stage application under 35 U.S.C. §371 of PCT Application No. PCT/US2013/026180, filed Feb. 14, 2013, which claims the benefit of U.S. Provisional Patent Application Ser. No. 61/598,343, filed Feb. 14, 2012; 61/605,057, filed Feb. 29, 2012; and 61/644,405 filed May 8, 2012 which are hereby incorporated by reference in their entirety.

FIELD OF THE INVENTION

The present invention relates to a method for relative quantification of nucleic acid sequence, expression, or copy changes using combined nuclease, ligation, and polymerase reactions.

BACKGROUND OF THE INVENTION

Ligation-based nucleic acid detection reactions typically employ two or more nucleic acid-based oligonucleotides annealed to a complementary nucleic acid target. These oligonucleotides immediately abut one-another and a ligase is employed to generate a phosphodiester bond across a nick by joining the 5'-phosphate of one oligonucleotide with the 3'-OH of the immediately adjacent oligonucleotide. The ligation assays are usually multiplexed. However, non-specific ligations, especially having two oligonucleotides ligating on a third oligonucleotide in a multiplex reaction can generate undesirable false positive results. Moreover, multiplex polymerase chain reaction (PCR), ligation chain reaction (LCR) and ligation detection reaction (LDR)/PCR methods are limited by the number of primers that can be combined for a variety of reasons including: (i) propensity for combinations of oligonucleotides and targets to form "primer-dimer" off target-type complexes, (ii) PCR amplification bias derived from amplification using primer sequences that have inherently different annealing bias and varying target specificities, (iii) for LCR and LDR/PCR, the abundant 5' phosphate groups produce a high background of unintended ligation and subsequently spurious amplification products, and (iv) biochemical, informatic, and raw material cost issues associated with scaling amplification reactions as multiplex target numbers increase.

In order to improve the ability to specifically amplify single or multiple nucleic acids targets in an inexpensive and robust manner, methodologies outside traditional single/multiplex PCR or LCR need to be deployed. The ability to reliably detect low frequency mutations for single-plex and multiplex use (for example, a single mutated molecule in $10^4$ normal background (specificity to detect signal that is 0.01% of DNA with similar sequence) would be of great value, especially in the diagnostic arena. Achieving this specificity may enable detection of cancer signatures in samples with low/rare amounts of tumor DNA, e.g., samples containing circulating tumor cells and cell-free DNA from tumor cells. Simple, specific and inexpensive assays to do this are needed, but do not exist.

The present invention is directed at overcoming this and other deficiencies in the art.

SUMMARY OF THE INVENTION

A first aspect of the present invention is directed to a method for identifying the presence of one or more target nucleotide sequences in a sample. This method involves providing a sample potentially containing the one or more target nucleotide sequences and providing one or more oligonucleotide probe sets. Each probe set comprises (a) a first oligonucleotide probe having a target-specific portion, and (b) a second oligonucleotide probe having a target specific portion. The first and second oligonucleotide probes of a probe set are configured to hybridize adjacent to one another on the target nucleotide sequence with a junction between the first and second oligonucleotide probes, and, in a probe set, the target specific portion of the second oligonucleotide probe has an overlapping identical nucleotide at the junction with the first oligonucleotide probe. The method further involves contacting the sample and the one or more oligonucleotide probe sets under conditions effective for first and second oligonucleotide probes of a probe set to hybridize at adjacent positions in a base specific manner to their corresponding target nucleotide sequences, if present in the sample, where upon hybridization the overlapping identical nucleotide of the second oligonucleotide probe forms a flap at the junction comprising the overlapping identical nucleotide. The overlapping identical nucleotide of the second oligonucleotide probe is cleaved with an enzyme having 5' nuclease activity, thereby liberating a phosphate at the second oligonucleotide probe's 5'end, and the first and second oligonucleotide probes of a probe set ligate together at the junction to form ligated product sequences. The ligated product sequences in the sample are detected and the presence of one or more target nucleotide sequences in the sample is identified based on the detection.

Another aspect of the present invention is directed to a method for identifying a presence of one or more target nucleotide sequences in a sample. This method involves providing a sample potentially containing the one or more target nucleotide sequences and providing one or more oligonucleotide probe sets. Each probe set comprises (a) a first oligonucleotide probe having a target-specific portion, and (b) a second oligonucleotide probe having 5' non-target specific flap portion and a target-specific portion containing one or more thiophosphate-modified nucleotide bases, wherein the first and second oligonucleotide probes of a probe set are configured to hybridize on the target nucleotide sequence. The sample and the one or more oligonucleotide probe sets are contacted under conditions effective for first and second oligonucleotide probes of a probe set to hybridize in a base specific manner to their corresponding target nucleotide sequences, if present in the sample. The 5' non-target specific flap portion of the second oligonucleotide probe is cleaved with an enzyme having 5' nuclease activity, thereby liberating a 5' phosphate at a first nucleotide base of the target-specific portion of the second oligonucleotide, and the first and second oligonucleotide probes of the one or more oligonucleotide probe sets are ligated together to form ligated product sequences containing the target-specific portions with the one or more thiophosphate-modified nucleotide bases. The method further comprises detecting ligated product sequences in the sample and identifying the presence of the one or more target nucleotide sequences in the sample based on this detection.

Another aspect of the present invention is directed to a method for identifying a presence of one or more target nucleotide sequences in a sample. This method involves providing a sample potentially containing the one or more target nucleotide sequences and providing one or more oligonucleotide probe sets. Each probe set has (i) a first oligonucleotide probe comprising a 5' primer-specific portion, a first portion of a zip-code portion, a first tag portion that is 3' to the first zip-code portion, and a target-specific portion, and (ii) a second oligonucleotide probe comprising a 3' primer-specific portion, a second portion of the zip-code portion, a second tag portion that is 5' to the second zip-code portion, and a target-specific portion. The first and second zip-code portions of an oligonucleotide probe set, when adjacently positioned, form a full-length zip-code portion, and the first and second tag portions of an oligonucleotide probe set are complementary to each other. The sample and the one or more oligonucleotide probe sets are contacted under conditions effective for first and second oligonucleotide probes of a probe set to hybridize in a base specific manner to their corresponding target nucleotide sequences, if present in the sample, and first and second oligonucleotide probes of the one or more probe sets are ligated together to form ligated product sequences. This method further involves providing one or more oligonucleotide primer sets, each set comprising (a) a first oligonucleotide primer comprising the same nucleotide sequence as the 5' primer-specific portion of the ligated product sequence and (b) a second oligonucleotide primer comprising a nucleotide sequence that is complementary to the 3' primer-specific portion of the ligated product sequence. The ligated product sequences, the one or more oligonucleotide primer sets, and a DNA polymerase are blended to form a polymerase chain reaction mixture, and the polymerase chain reaction mixture is subjected to one or more polymerase chain reaction cycles thereby forming primary extension products. A collection of capture oligonucleotides that are complementary to a portion of the first zip-code portion and a portion of the second zip-code portion are provided. Each capture oligonucleotide of the collection for each different primary extension product has a different nucleotide sequence and comprises a quencher molecule and a detectable label separated from each other. The primary extension products and the collection of capture oligonucleotides are subjected to conditions effective for (i) the first and second tag portions of a particular primary extension product to hybridize to each other to form hairpinned extension products with adjacently positioned first and second zip-code portions and (ii) the capture oligonucleotides of the collection to hybridize to complementary adjacently positioned first and second zip-code portions of the hairpinned extension products. The quencher molecule or the detectable label is cleaved from hybridized capture oligonucleotides, and the detectable label separated from the quencher molecule is detected. The presence of the one or more target nucleotide sequences in the sample is identified based on this detection Another aspect of the present invention is directed to a method for identifying a presence of one or more target nucleotide sequences in a sample. This method involves providing a sample potentially containing the one or more target nucleotide sequences and providing one or more oligonucleotide probe sets. Each probe set has (i) a first oligonucleotide probe comprising a 5' primer-specific portion, a first portion of a zip-code portion, a first tag portion that is 3' to the first zip-code portion, and a target-specific portion, and (ii) a second oligonucleotide probe comprising a 3' primer-specific portion, a second portion of the zip-code portion, a second tag portion that is 5' to the second zip-code portion and a target-specific portion. The first and second zip-code portions of an oligonucleotide probe set, when adjacently positioned, form a full-length zip-code portion, and the first and second tag portions of an oligonucleotide probe set are complementary to each other. The sample and the one or more oligonucleotide probe sets are contacted under conditions effective for first and second oligonucleotide probes of a probe set to hybridize in a base specific manner to their corresponding target nucleotide sequences, if present in the sample, and the first and second oligonucleotide probes of the one or more probe sets are ligated together to form ligated product sequences. The method further involves providing one or more oligonucleotide primer sets, each set comprising (i) a first oligonucleotide primer having (a) a nucleotide sequence that is the same as the second primer-specific portion of the first oligonucleotide probe, (b) a capture oligonucleotide portion that is complementary to adjacently positioned first and second zip-code portions of an oligonucleotide probe set, (c) a quencher molecule and a detectable label separated by said capture oligonucleotide portion, (ii) a second oligonucleotide primer comprising a nucleotide sequence that is complementary to the 3' primer-specific portion of the ligated product sequence. The ligated product sequences, the one or more oligonucleotide primer sets, and a DNA polymerase are blended to form a polymerase chain reaction mixture and the polymerase chain reaction mixture is subjected to one or more polymerase chain reaction cycles thereby forming primary extension products. The primary extension products are subject to conditions effective for the first and second tag portions of a particular primary extension product to hybridize to each other to form hairpinned primary extension products with adjacently positioned first and second zip-code portions and (ii) the capture oligonucleotide portion of a particular hairpinned primary extension product to hybridize to complementary adjacently positioned first and second zip-code portions of the hairpinned extension product. The quencher molecule or the detectable label of the hairpinned primary extension products is cleaved, and the detectable label separated from the quencher molecule is detected. The presence of the one or more target nucleotide sequences in the sample is identified based on this detection Another aspect of the present invention is directed to a kit for identifying a presence of one or more target nucleotide sequences in a sample. The kit contains an enzyme having 5' nuclease activity, a ligase, and one or more oligonucleotide probe sets. The oligonucleotide probe sets each have (a) a first oligonucleotide probe having a target-specific portion, and (b) a second oligonucleotide probe having a target specific portion, wherein the first and second oligonucleotide probes of a probe set are configured to hybridize adjacent to one another on the target nucleotide sequence with a junction between the first and second oligonucleotide probes, and where, in a probe set, the target specific portion of the second oligonucleotide probe has an overlapping identical nucleotide at the junction with the first oligonucleotide probe.

Another aspect of the present invention is directed to a kit for identifying a presence of one or more target nucleotide sequences in a sample. This kit contains an enzyme having 5' nuclease activity, a ligase, and one or more oligonucleotide probe sets. The oligonucleotide probe sets each have (a) a first oligonucleotide probe having a target-specific portion, and (b) a second oligonucleotide probe having 5' non-target specific flap portion and a target-specific portion containing one or more thiophosphate-modified nucleotide bases, where the first and second oligonucleotide probes of a probe set are configured to hybridize on the target nucleotide sequence.

Described herein are methods that resolve primer target promiscuity and the difficulty in balancing amplification between primer pairs in a multiplex amplification reaction.

The method permits: (a) a fundamental increase in the number of targets that can be simultaneously examined in a single sample, (b) decreases the amount of sample required, and (c) provides a method to examine rare, or low quantity/low quality/degraded (e.g., single cell/Formalin-Fixed, Paraffin-Embedded (FFPE)/maternal circulating fetal or tumor-derived nucleic acid samples.

BRIEF DESCRIPTION OF THE DRAWINGS

In FIG. 1A, a first oligonucleotide probe having a target-specific portion with a ligation competent 3' OH is overlapped by the immediately flanking 5' OH end of the second oligonucleotide probe, also having a target-specific portion, when the first and second oligonucleotide probes hybridize at adjacent positions on a target nucleotide sequence. When the overlapping flap nucleotide of the second oligonucleotide probe is the same nucleotide as the terminating 3' nucleotide on the first oligonucleotide probe, the phosphodiester bond immediately upstream of the matching nucleotide of second oligonucleotide probe can be discriminatingly cleaved by an enzyme with FEN activity. On both probes, the 3' and 5' terminating nucleotides are the same, "X". "X" on the target nucleic acid molecule can be either a variable, e.g., a SNP or conserved nucleotide. As shown in FIG. 1B, nuclease-type flap activity generates a ligation competent 5' $PO_4$ and the flap cleavage product (X) is released. Because first and second oligonucleotide probes hybridize immediately adjacent to one another, a ligase seals the nick (FIG. 1C). Multiple rounds of heat, anneal, nuclease-ligation actions can be used to generate multiple ligated molecules on a single target. Ligation products (~70-250 nucleotide length) can be readily purified from lower MW ligation product, e.g., using Sephadex. In this depiction, the first oligonucleotide probe has a 5' primer-specific portion and the second oligonucleotide probe has a 3' primer-specific portion which aid in downstream detection of the ligation product. The oligonucleotide probes can contain alternative portions related to detection as described herein. FIG. 1D shows a double ligation-nuclease reaction with first, second, and third oligonucleotide probes.

In FIG. 4A the second oligonucleotide probe has a 3' tail $C_1$ that is complementary to the $C_1$'5' tail on the first oligonucleotide probe, and in FIG. 4B, the second oligonucleotide probe has a 3' tail $A_1$' that is complementary to the $A_1$ 5' tail on the first oligonucleotide probe. In both cases, the correct ligation products form a hairpin at the temperature used for exonuclease I treatment. Single-strand-specific 3' exonuclease cleaves single-stranded unligated oligonucleotides, but not ligated products that form hairpins. In FIG. 4C, the first and second oligonucleotide probes bear allele specific complementary tags, $C_1$ and $C_1$', and additionally, the second oligonucleotide probe has a universal tag $L_1$. After ligation, a hairpin forms upon hybridization of $C_1$ and $C_1$'. A universal biotinylated oligonucleotide ($L_1$') is ligated to the hairpinned product in the same reaction permitting streptavidin selection for biotin-bearing ligation products.

FIG. 9B shows detection using the zipcode in a traditional Taqman® (Roche Molecular Systems, Pleasanton, Calif.) type assay where the capture oligonucleotide serves as the Taqman® probe. FIG. 9C shows zipcode mediated capture of the products on a universal array containing complementary capture oligonucleotides.

FIGS. 12A-12B show that either strand of a target nucleic acid can be used for ligation with probes containing UniTaq detection and primer portions.

In FIG. 14, Step 1, allele specific first oligonucleotide probes with 5' tails Aix and Aio, and allele-specific second oligonucleotide probes, where i=1 to N, are used for multiplexed nuclease-ligase reaction. Universal primers with dyes D1 & D2, which are specific for each allele (FIG. 14, Step 2), are used to generate a signal in colors D1 and/or D2 depending on the presence of the two alleles in the target nucleic acid (FIG. 14, Step 3) using UniTaq mediated hairpin formation.

FIG. 15A shows multiplex encoding nuclease-ligase encoding reaction for N targets on chromosome 21. All targets have been selected to have a short universal tag B1 and ligation point is picked somewhere within the tag or within one of the ligation oligonucleotides. For the control region, a double ligation method with a middle oligonucleotide is shown: all ligation products having a universal tag B2. In FIG. 15B, ligation products have universal tags at the ends and short middle tags B1 and B2. In FIGS. 15C and 15D, a detection example is shown using UniTaq method and short universal tag. Counts of wells with D1 and D2 signal can be used to detect fetal aneuploidy. A short universal probe can be used as well, e.g., FIG. 15B. C1 and C2 can be the same primer.

DETAILED DESCRIPTION OF THE INVENTION

Figure 1:
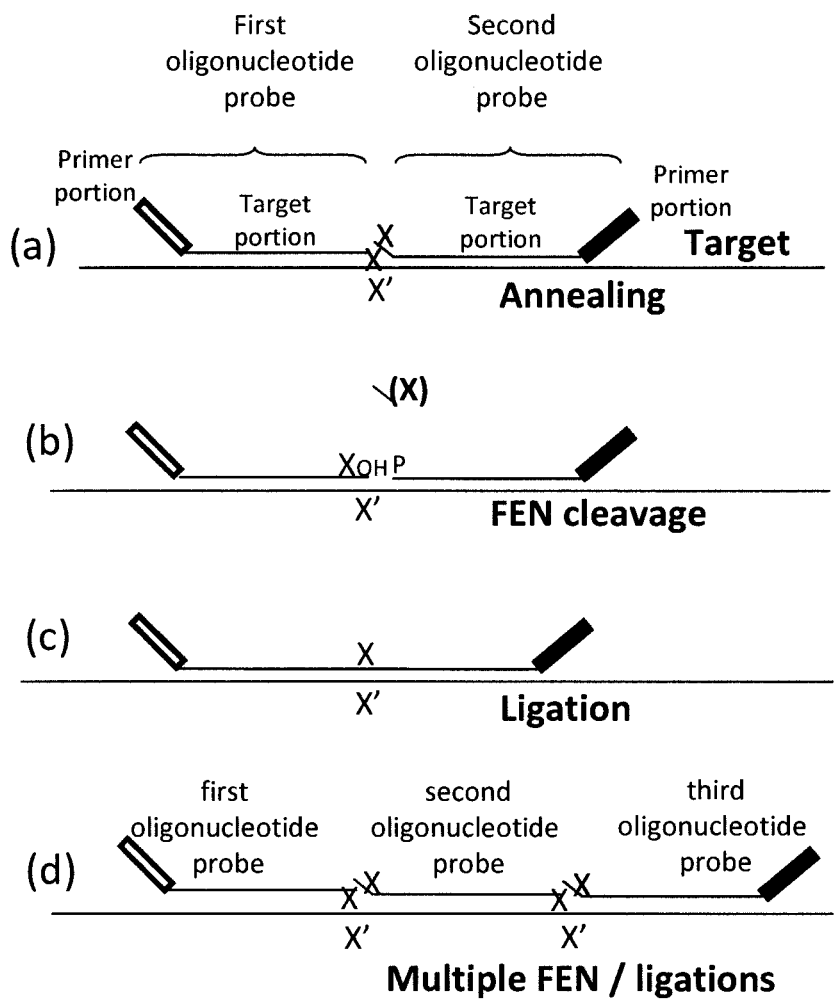
FIGS. 1A-1D show the 5'-nuclease (FEN)-ligation process of the present invention.

A first aspect of the present invention is directed to a method for identifying the presence of one or more target nucleotide sequences in a sample. This method involves providing a sample potentially containing the one or more target nucleotide sequences and providing one or more oligonucleotide probe sets. Each probe set comprises (a) a first oligonucleotide probe having a target-specific portion, and (b) a second oligonucleotide probe having a target specific portion. The first and second oligonucleotide probes of a probe set are configured to hybridize adjacent to one another on the target nucleotide sequence with a junction between the first and second oligonucleotide probes, and, in a probe set, the target specific portion of the second oligonucleotide probe has an overlapping identical nucleotide at the junction with the first oligonucleotide probe. The method further involves contacting the sample and the one or more oligonucleotide probe sets under conditions effective for first and second oligonucleotide probes of a probe set to hybridize at adjacent positions in a base specific manner to their corresponding target nucleotide sequences, if present in the sample, where upon hybridization the overlapping identical nucleotide of the second oligonucleotide probe forms a flap at the junction comprising the overlapping identical nucleotide. The overlapping identical nucleotide of the second oligonucleotide probe is cleaved with an enzyme having 5' nuclease activity, thereby liberating a phosphate at the second oligonucleotide probe's 5'end, and the first and second oligonucleotide probes of a probe set ligate together at the junction to form ligated product sequences. The ligated product sequences in the sample are detected and the presence of one or more target nucleotide sequences in the sample is identified based on the detection.

FIGS. 1A-1D depict the process of detecting a target nucleic acid molecule using the coupled nuclease-ligase reaction of the present invention. The reaction utilizes a plurality of probe sets, each probe set consisting of at least a first and a second oligonucleotide probe. Each oligonucleotide probe has a target-specific portion that is complementary to a region of a target nucleic acid molecule sequence. The first oligonucleotide probe bears a ligation competent 3' OH group while the second oligonucleotide probe bears a ligation incompetent 5' end (i.e., an oligonucleotide probe without a 5' phosphate). In accordance with the method of the present invention the oligonucleotide probes of a probe set are designed such that the 3'-most base of the first oligonucleotide probe is overlapped by the immediately flanking 5'-most base of the second oligonucleotide probe that is complementary to the target nucleic acid molecule. The overlapping nucleotide is referred to as a "flap". When the overlapping flap nucleotide of the second oligonucleotide probe is complementary to the target nucleic acid molecule sequence and the same sequence as the terminating 3' nucleotide of the first oligonucleotide probe, the phosphodiester bond immediately upstream of the flap nucleotide of the second oligonucleotide probe is discriminatingly cleaved by an enzyme having flap endonuclease (FEN) or 5' nuclease activity. That specific FEN activity produces a novel ligation competent 5' phosphate end on the second oligonucleotide probe that is precisely positioned alongside the adjacent 3' OH of the first oligonucleotide probe. As a consequence of (a) target specific annealing by oligonucleotide probes adjacent to each other, (b) selective generation of 5' phosphates only when the cleaved flap nucleotide matches the template, and (c) addition of a ligase that discriminates against non-Watson-Crick pairing for the 3'-base of the first oligonucleotide probe, the method of the present invention is able to achieve very high target detection specificity and sensitivity. Kinetic approaches, such as altering the cycling times and conditions can also be employed to enhance the discrimination between wild-type and mutant target nucleic acid molecules Ligase discrimination can be further enhanced by employing various probe design features. For example, an intentional mismatch or nucleotide analogue (e.g., Inosine, Nitroindole, or Nitropyrrole) can be incorporated into the first oligonucleotide probe at the $2^{nd}$ or $3^{rd}$ base from the 3' junction end to slightly destabilize hybridization of the 3' end if it is perfectly matched at the 3' end, but significantly destabilize hybridization of the 3' end if it is mis-matched at the 3' end (FIG. 2A). This design reduces inappropriate misligations when mutant probes hybridize to wild-type target. Alternatively, RNA bases that can be cleaved by RNAses can be incorporated into the oligonucleotide probes to ensure template-dependent product formation. For example, Dobosy et. al. "RNase H-Dependent PCR (rh-PCR): Improved Specificity and Single Nucleotide Polymorphism Detection Using Blocked Cleavable Primers," BMC Biotechnology 11(80): 1011 (2011), which is hereby incorporated by reference in its entirety, describes using an RNA-base close to the 3' end of an oligonucleotide probe with 3'-blocked end, and cutting it with RNAse H2 generating a PCR-extendable and ligatable 3'-OH. This approach can be used to generate either ligation-competent 3'OH or 5'-P, or both, provided a ligase that can ligate 5'-RNA base is utilized.

For insertions or deletions, incorporation of a matched base or nucleotide analogues (e.g., -amino-dA or 5-propynyl-dC) in the first oligonucleotide probe at the $2^{nd}$ or $3^{rd}$ position from the junction improves stability and may improve discrimination of such frameshift mutations from wild-type sequences (FIGS. 2B-2C). For insertions, use of one or more thiophosphate-modified nucleotides downstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target (FIG. 2B). Likewise, for deletions, use of one or more thiophosphate-modified nucleotides upstream from the desired scissile phosphate bond of the second oligonucleotide probe will prevent inappropriate cleavage by the 5' nuclease enzyme when the probes are hybridized to wild-type DNA, and thus reduce false-positive ligation on wild-type target (FIG. 2C).

Other possible modifications included abasic sites, e.g., dSpacer (aka, THF tetrahydrofuran) or oxo-G. These abnormal "bases" have specific enzymes that remove abnormal base and generate ligation-competent 3'-OH or 5'P sites. Endonuclease IV, Tth EndoIV (NEB) will remove abasic residues after the ligation oligonucleotides anneal to the target nucleic acid, but not from a single-stranded DNA. Similarly, one can use oxo-G with Fpg or inosine/uracil with EndoV or Thimine glycol with EndoVIII.

As shown in FIG. 1D, a probe set of the present invention can further comprise a third oligonucleotide probe also having a target-specific portion that is complementary to a region of the target nucleic acid molecule. In this embodiment, the second and third oligonucleotide probes of a probe set are configured to hybridize adjacent to one another on the target nucleotide sequence with a junction between them. The target specific portion of the third oligonucleotide probe has an overlapping identical nucleotide flap at the junction with the second oligonucleotide probe in a probe set that is removed by an enzyme having FEN activity when it is complementary to the target nucleotide sequence and is the same sequence as the terminating 3' nucleotide of the second oligonucleotide probe. Cleavage of the flap liberates a ligation competent 5'phosphate on the third oligonucleotide probe that allows ligation between the second and third oligonucleotide probes at the junction to form a ligated product sequence The utilization of three probes in a primer set allows for detection of longer target regions with increased specificity Flap endonucleases or 5' nucleases that are suitable for cleaving the 5' flap of the second oligonucleotide probe prior to ligation include, without limitation, polymerases the bear 5' nuclease activity such as E. coli DNA polymerase and polymerases from Taq and T. thermophilus, as well as T4 RNase H and TaqExo.

The ligation reaction utilized in the method of the present invention is well known in the art. Ligases suitable for ligating oligonucleotide probes of a probe set together following cleavage of the 5' flap on the second oligonucleotide probe include, without limitation Thermus aquaticus ligase, E. coli ligase, T4 DNA ligase, T4 RNA ligase, Taq ligase, 9 N° ligase, and Pyrococcus ligase, or any other thermostable ligase known in the art. In accordance with the present invention, the nuclease-ligation process of the present invention can be carried out by employing an oligonucleotide ligation assay (OLA) reaction (see Landegren, et al., "A Ligase-Mediated Gene Detection Technique," Science 241:1077-80 (1988); Landegren, et al., "DNA Diagnostics—Molecular Techniques and Automation," Science 242:229-37 (1988); and U.S. Pat. No. 4,988,617 to Landegren, et al.), a ligation detection reaction (LDR) that utilizes one set of complementary oligonucleotide probes (see e.g., WO 90/17239 to Barany et al, which is hereby incorporated by reference in their entirety), or a ligation chain reaction (LCR) that utilizes two sets of complementary oligonucleotide probes see e.g., WO 90/17239 to Barany et al, which is hereby incorporated by reference in their entirety).

The oligonucleotide probes of a probe sets can be in the form of ribonucleotides, deoxynucleotides, modified ribonucleotides, modified deoxyribonucleotides, peptide nucleotide analogues, modified peptide nucleotide analogues, modified phosphate-sugar-backbone oligonucleotides, nucleotide analogs, and mixtures thereof.

The hybridization step in the ligase detection reaction, which is preferably a thermal hybridization treatment discriminates between nucleotide sequences based on a distinguishing nucleotide at the ligation junctions. The difference between the target nucleotide sequences can be, for example, a single nucleic acid base difference, a nucleic acid deletion, a nucleic acid insertion, or rearrangement. Such sequence differences involving more than one base can also be detected. Preferably, the oligonucleotide probe sets have substantially the same length so that they hybridize to target nucleotide sequences at substantially similar hybridization conditions.

The nuclease-ligation products of the present invention can be detected using a variety of detection methods known in the art. For example, the ligation products can be detected by sequencing the ligation product using methods well known in the art. Alternatively, the ligation products can be separated by size and detected. To facilitate detection via sequencing or size separation, the oligonucleotide probes of a probe set may further comprise one or more detectable labels, primer-portions, or other detection portions. A number of suitable detection portions and methods of detections are illustrated in the accompanying figures and described in more detail below.

In one embodiment of the present invention, detection of the ligation products is facilitated by a zip-code portion. In accordance with this embodiment, one of the oligonucleotide probes in a probe set further comprises a zip-code portion and the other oligonucleotide probe of the probe set comprises a detectable label. As used herein, a zip-code is a short nucleotide sequence, e.g., between 16 to 24 nucleotides in length, that has no sequence identity to the target nucleotide sequence, and preferably, little or no sequence identify to any genomic nucleotide sequence. In a collection of zip-codes, each zip-code differs in sequence from the sequence of other zip-codes in the collection by at least 25%, yet all zip-codes of a collection are designed to have similar melting temperatures so as to facilitate hybridization to complementary capture oligonucleotides under uniform hybridization conditions with little or no non-specific hybridization to non-capture oligonucleotide sequences. In one embodiment of the present invention, the zip-code portion of an oligonucleotide probe of a probe set is used to identify and distinguish individual ligated product sequences in a sample, therefore the zip-code portion for each different ligated product sequence has a different nucleotide sequence (i.e., the zip-code portions are allele specific). This embodiment is particularly useful for detecting and distinguishing different allele mutations. In an alternative embodiment, where the goal is to simply detect the presence of a mutation in a gene or chromosome copy number, but the identity of the mutation or chromosomal region is not critical, the same zip-code portion may be used to detect different ligation products. In either embodiment, incorporation of zip-codes into one of the oligonucleotide probes of a probe set allows for highly multiplexed detection of various target sequences simultaneously. Methods of designing collections of zip-code sequences and their complementary capture oligonucleotides sequences are described in detail in U.S. Pat. Nos. 6,852,487, 7,455,965, and 6,506,594 all to Barany et al., which are hereby incorporated by reference in their entirety.

Ligation products containing zip-code portions are contacting with a collection of immobilized capture oligonucleotides under uniform hybridization conditions effective to hybridize the zip-code portion of each ligated product sequence to its complementary capture oligonucleotide. Since zip-codes in the collection vary in nucleotide sequence, e.g., by at least 25% of their sequence when aligned, hybridization between a plurality of ligation product zip-codes and their complementary capture oligonucleotides occurs with minimal non-specific hybridization. Immobilized ligation products are detected via their detectable label.

Figure 3:
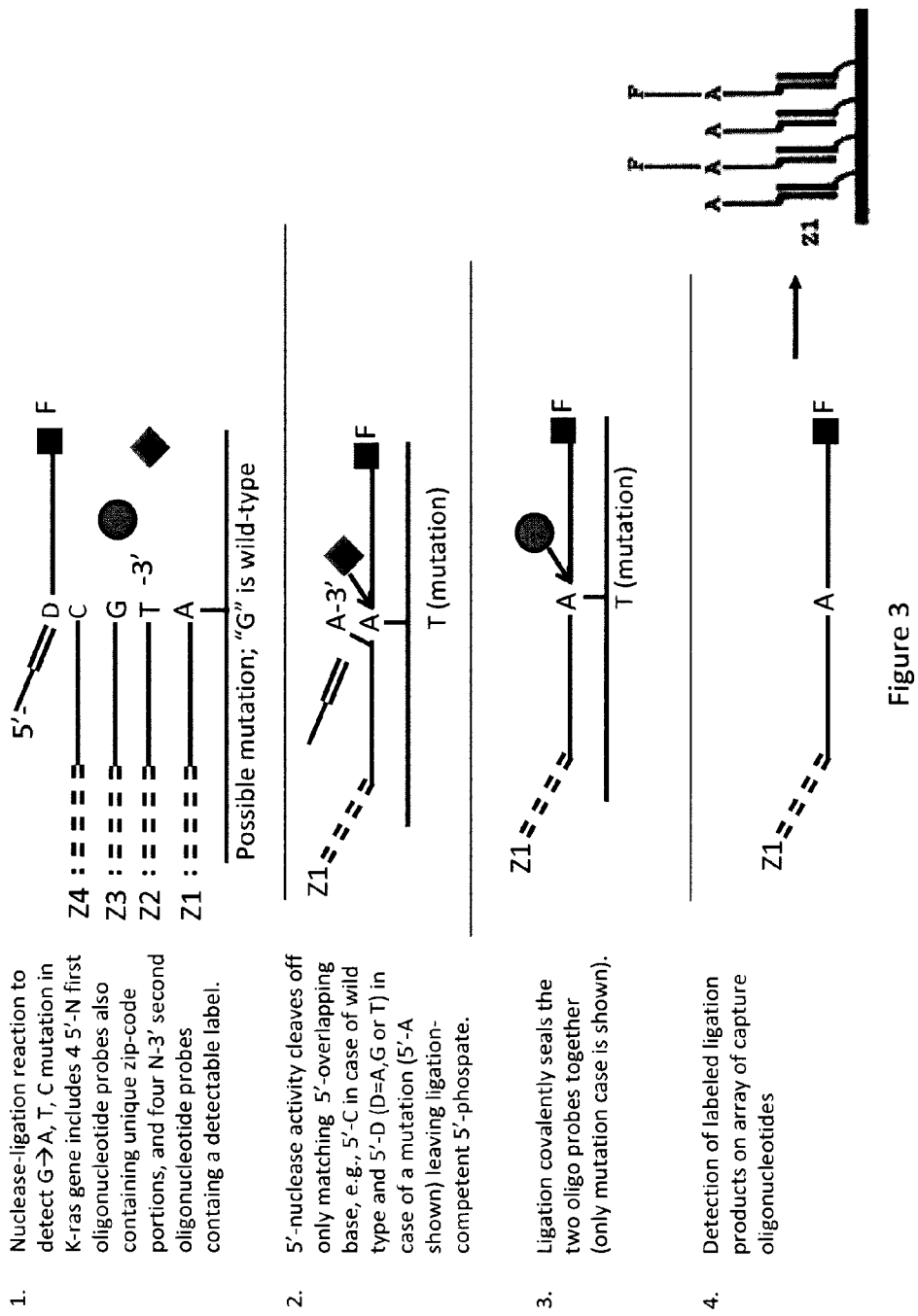
FIG. 3 shows the nuclease-ligation-zipcode array capture process of the present invention to detect multiple single-base mutations in a target nucleotide sequence

FIG. 3 is a flow diagram of the nuclease-ligation-zipcode capture process in accordance with the present invention to detect G→A, T, C mutation in the K-ras gene. The method, as depicted in this example, involves four 5'-N second oligonucleotide probes and four N-3' first oligonucleotide probes. Each first oligonucleotide probe comprises a different zip-code portion (i.e., Z1, Z2, Z3, or Z4) and each second oligonucleotide probe comprises a detectable label (F). As shown in step 2, 5'-nuclease activity (♦) cleaves off only matching 5'-overlapping base and additional flap, e.g., 5'-D (D=A, G or T) in case of a mutation (5'-A shown) leaving ligation-competent 5'-phosphate on the second oligonucleotide probe. Ligase (●) covalently seals the two oligonucleotide probes together (only mutation case is shown). In this example, the presence of a mutant T in the target nucleotide sequence causes the first oligonucleotide probe with the 3'A and the addressable array-specific portion Z1 to ligate to the oligonucleotide probe having a 5' overlapping identical A nucleotide after nuclease-mediated cleavage of the 5' overlapping identical A nucleotide. The presence of the T allele in the target nucleotide sequence is indicated by the fluorescent signal (F) detected at the address on the solid support having the capture oligonucleotide probe complementary to portion Z1 of the ligated product sequence. Appearance of the fluorescent signal (F) at the positions on the solid support comprising the capture oligonucleotide probes that are complementary to Z2, Z3, and Z4 zip-codes (which would be located at different positions on the solid support than each other and the complement of Z1) likewise indicates the presence of A, C, and G alleles in the target nucleotide sequence, respectively.

As indicated in FIG. 3, detection of the ligated product sequence containing a zip-code portion involves hybridization of the zip-code sequence to its complementary capture oligonucleotide. In one embodiment of the present invention, a collection of capture oligonucleotides is immobilized to a solid support, e.g., an array, beads, slides, discs, membranes, films, microtiter plates, and composites thereof. The solid support may comprise an array of positions with the collection of capture oligonucleotides being immobilized at the array of positions. Methods of forming capture oligonucleotide arrays on a solid support and their use for target nucleic acid capture is fully described in U.S. Pat. No. 6,852,487 and continuations and divisionals thereof all to Barany et al., which are hereby incorporated by reference in their entirety.

In accordance with this embodiment of the present invention, it may be preferable to perform an initial target nucleic acid amplification procedure prior to the nuclease-ligation reaction. This increases the quantity of the target nucleotide sequence in the sample prior employing the nuclease-ligation process. For example, the initial target nucleic acid amplification may be accomplished using the polymerase chain reaction process, self-sustained sequence replication, or Q-β replicase-mediated RNA amplification. The polymerase chain reaction process is the preferred amplification procedure and is fully described in H. Erlich, et. al., "Recent Advances in the Polymerase Chain Reaction," *Science* 252: 1643-50 (1991); M. Innis, et. al., *PCR Protocols: A Guide to Methods and Applications*, Academic Press: New York (1990); and R. Saiki, et. al., "Primer-directed Enzymatic Amplification of DNA with a Thermostable DNA Polymerase," *Science* 239: 487-91 (1988), which are hereby incorporated by reference. J. Guatelli, et. al., "Isothermal, in vitro Amplification of Nucleic Acids by a Multienzyme Reaction Modeled After Retroviral Replication," *Proc. Natl. Acad. Sci. USA* 87: 1874-78 (1990), which is hereby incorporated by reference, describes the self-sustained sequence replication process. The Q-β replicase-mediated RNA amplification is disclosed in F. Kramer, et. al., "Replicatable RNA Reporters," *Nature* 339: 401-02 (1989), which is hereby incorporated by reference.

In another embodiment of the present invention, the nuclease-ligation products are detected using next generation sequencing methods. In accordance with this embodiment, oligonucleotide probes of a probe set further comprise the appropriate sequencing tags or adaptors required for the Illumina® MiSeq™ or HiSeg™ (San Diego, Calif.) platform, the Life Technologies™ Ion Torrent™ (Life Technologies, Carlsbad, Calif.) platform, the Roche™ 454 platform, or other next generation sequencing platform (i.e., pyrosequencing, fluorescence-based sequencing-by-synthesis, fluorescence-based sequencing-by-ligation, ion-based sequencing-by-synthesis, and ion-based sequencing-by-ligation), which are all well known in the art. There is no need to have different tags for different chromosomes, as sequences themselves can be unambiguously mapped to one of the chromosomes in the human genome. Sequencing is particularly well suited for counting different single nucleotide polymorphism (SNP) alleles in a target nucleic acid molecule.

Figure 2:
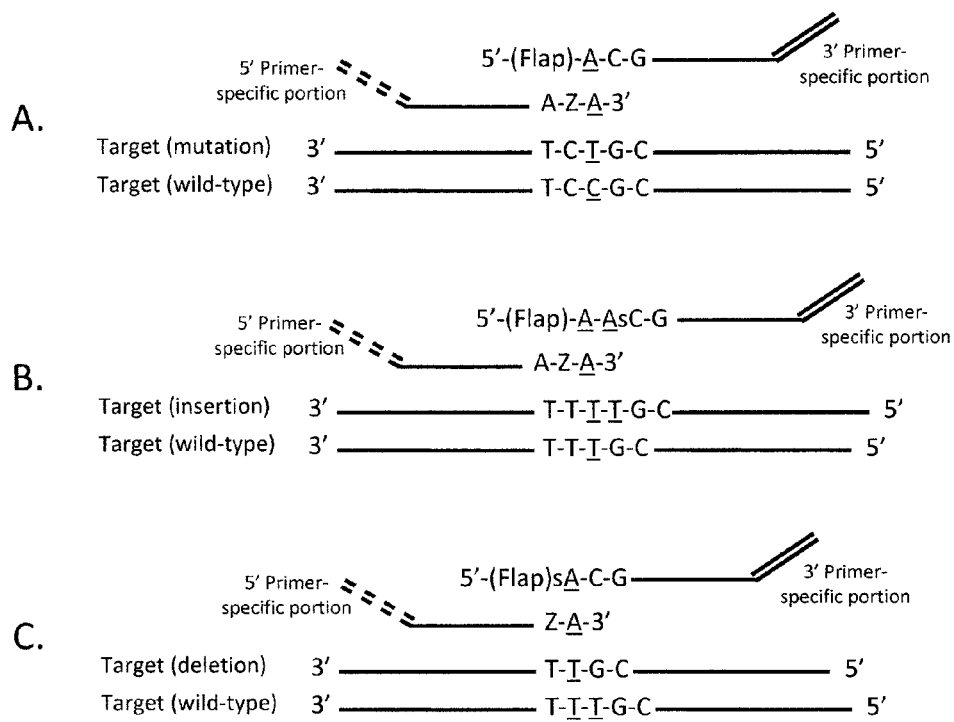
FIGS. 2A-2C show examples of oligonucleotide probe designs to detect mutations, insertions, and deletions by ligase detection reaction. "Z" denotes the base in the 2nd or 3rd (not shown) position from the 3' end of the first oligonucleotide probe and represents: dG, dA, Inosine, Nitroindole, Nitropyrrole or other nucleotide analogue. An additional probe design involves the inclusion of thiophosphates in the second oligonucleotide probe. The thiophosphate can be at the overlapping identical nucleotide base of the second oligonucleotide probe, or at a base 3' or 5' to the overlapping nucleotide base of the second oligonucleotide probe (FIGS. 2B and 2C). As described herein and depicted in this embodiment, the oligonucleotide probes of the prevent invention can also have upstream and downstream primer-specific portions which are useful for amplifying the ligation product in a subsequent polymerase chain reaction.

In another embodiment of the present invention detection of the nuclease-ligation products involves PCR amplification. In accordance with this embodiment, the first oligonucleotide probe of the probe set further comprises a 5' primer-specific portion and the second oligonucleotide probe in a probe set further comprises a 3' primer-specific portion as shown in FIGS. 1 and 2. The resulting ligation product comprises the 5' primer-specific portion, the target-specific portions, and the 3' primer-specific portion.

The primer-specific portions of the first and second oligonucleotide probes can be universal primer sequences allowing for subsequent universal amplification of all of the ligation products formed under a single set of conditions. This is particularly useful when detecting low abundance target nucleotide molecules. Accordingly, following ligation product formation, a universal PCR amplification is performed to proportionally amplify all ligation products in the sample. Following universal PCR, the extension products of the original ligation products are detected and quantified. Alternatively, the primer-specific portions of the first and second oligonucleotide probes can be specific for the target nucleotide sequence (i.e., allele-specific). In yet another embodiment, the oligonucleotide probes are designed to contain a set of universal primer-specific portions in combination with one or more target-specific primer-specific portions (i.e., allele-specific primer portions).

Following the nuclease-ligation reaction, the sample containing the ligation products is subject to a polymerase chain reaction. In the polymerase chain reaction, one or a plurality of oligonucleotide primer sets are provided. Each primer set has a first oligonucleotide primer containing the same sequence as the 5' primer-specific portion of the ligation product sequence and a second oligonucleotide primer complementary to the 3' primer-specific portion of the ligation product sequence. The nuclease-ligase reaction mixture is blended with the one or a plurality of oligonucleotide primer sets and the polymerase to form a polymerase chain reaction mixture.

The polymerase chain reaction mixture is subjected to one or more polymerase chain reaction cycles which include a denaturation treatment, a hybridization treatment, and an extension treatment. During the denaturation treatment, hybridized nucleic acid sequences are separated. The hybridization treatment causes primers to hybridize to their complementary primer-specific portions of the ligation product sequence. During the extension treatment, hybridized primers are extended to form extension products complementary to the sequences to which the primers are hybridized. In a first cycle of the polymerase chain reaction phase, the second oligonucleotide primer hybridizes to the 3' primer-specific portion of the ligation product sequence and is extended to form an extension product complementary to the ligation product sequence. In subsequent cycles, the first oligonucleotide primer hybridizes to the 5' primer-specific portion of the extension product complementary to the ligation product sequence and the second oligonucleotide primer hybridizes to the 3' downstream portion of the ligation product sequence.

In almost all cases, it is desirable to occlude unligated oligonucleotide probes from the sample containing ligated product sequences prior to PCR amplification to prevent unligated probe extension and/or amplification that may generate false positive signals. Several means for achieving this objective are described below.

Figures 4A, 4B:
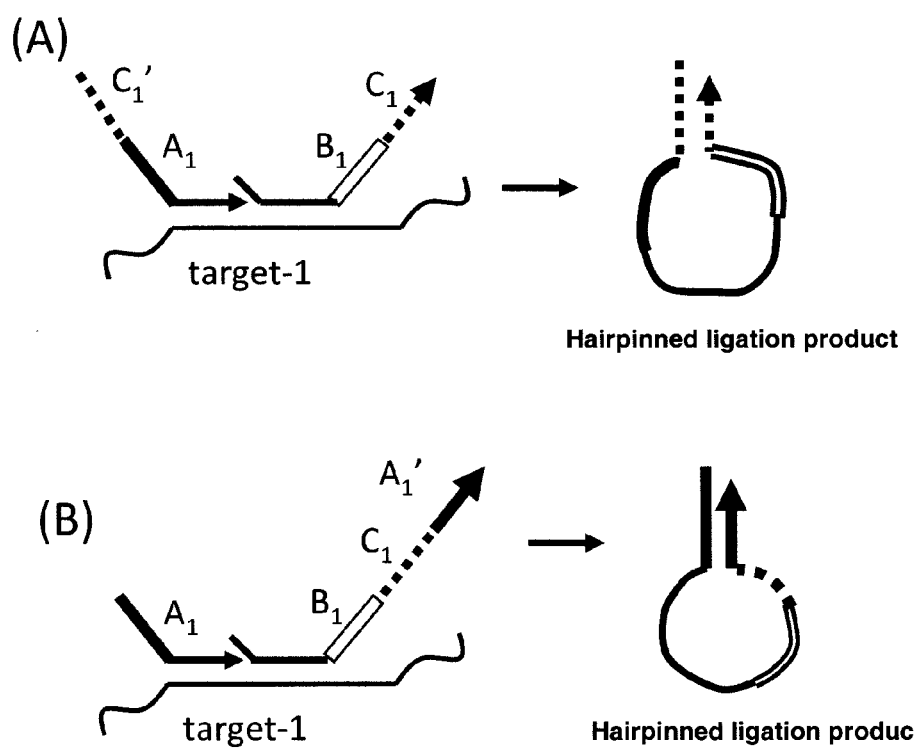
FIGS. 4A-4C are schematics showing various oligonucleotide probe designs that facilitate separation of ligation products from unligated oligonucleotide probes.

One approach involves removing unligated probe sequences from a sample following the ligation process by exonuclease digestion prior to amplification (L-H Guo and R. Wu, *Methods in Enzymology* 100:60-96 (1985), which is hereby incorporated by reference). To incorporate exonuclease digestion, the ligation products need to be protected from digestion. In one approach, the first and second oligonucleotide probes of a probe sets comprise complementary first and second tag portions, respectively. The first and second tag portions of an oligonucleotide probe set preferably, but not necessarily, differ in sequence from the tag portions of other oligonucleotide probe sets, i.e. they can be allele specific. FIG. 4A shows an example where the first oligonucleotide probe contains the tag portion C1' and the second oligonucleotide probe contains the tag portion C1, where C1' and C1 are complementary to each other. After ligation of the first and second oligonucleotide probes of a probe set, the first and second tag portions, i.e., C1' and C1, hybridize to form a hairpinned ligated product sequence that is resistant to exonuclease digestion ($A_1$ and $B_1$ in this schematic represent primer-specific portions for downstream polymerase chain reaction). Subsequent exonuclease digestion removes unligated probes. In addition, non-specifically ligated molecules, which bear mismatched tags and remain wholly or partially single-stranded and are also digested. Following exonuclease digestion, the hairpinned ligation products are denatured and PCR amplification is performed using oligonucleotide primer sets having a first primer that is complementary to the 3'primer specific portion of the ligation product (i.e., $B_1$) and a second primer that has the same nucleotide sequence as the 5' primer specific portion of the ligation product (i.e., $A_1$).

FIG. 4B shows an alternative oligonucleotide probe design where the second oligonucleotide probe contains a region ($A_1$') that is complementary to the 5' primer specific portion of the first oligonucleotide probe ($A_1$). After ligation of the first and second oligonucleotide probes of this probe set, $A_1$ and $A_1$' hybridize to form a hairpinned ligation product. Again, unligated oligonucleotide probes and non-specifically ligated molecules, which bear mismatched tags and remain wholly or partially single-stranded, and are subsequently digested using a single-strand specific exonuclease enzyme, e.g. ExoI. As noted above for FIG. 4A, following exonuclease digestion, the hairpinned ligation products are denatured, and oligonucleotides primers and a polymerase are added to amplify the denatured ligation products in the absence of any unligated probes.

In an alternative embodiment, the oligonucleotide probes of a probe set may comprise blocking moieties at their ends not involved in ligation. Suitable blocking moieties include a detectable label or a phosphorothioate group (Nikiforow, et al., "The Use of Phosphorothioate Primers and Exonuclease Hydrolysis for the Preparation of Single-stranded PCR Products and their Detection by Solid-phase Hybridization," *PCR Methods and Applications*, 3:p. 285-291 (1994), which is hereby incorporated by reference). After the ligation process, unligated probes are selectively destroyed by incubation of the reaction mixture with the exonuclease, while ligated probes are protected due to the elimination of free 3' ends which are required for initiation of the exonuclease reaction.

Figure 4C:
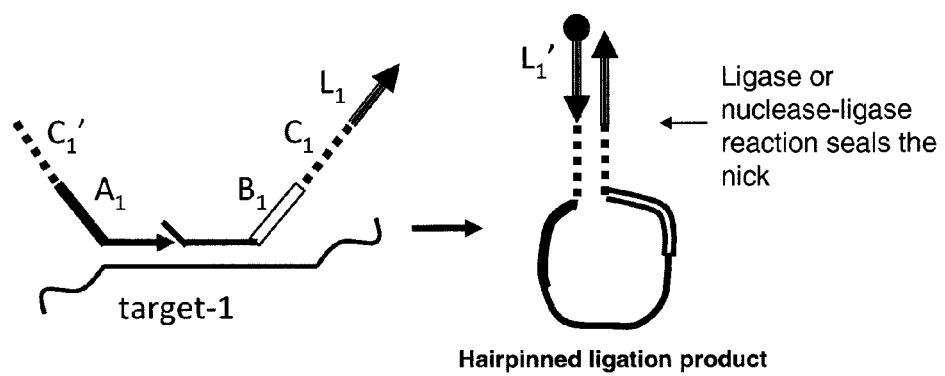

FIG. 4C shows another approach for separating ligation products from unligated oligonucleotide probes that relies on selection of ligation products. In this embodiment, the first and second oligonucleotide probes bear allele specific complementary tags, $C_1$ and $C_1$', and additionally, the second oligonucleotide probe has a universal tag $L_1$. After ligation, a hairpin forms upon hybridization of $C_1$ and $C_1'$, this hairpin having a protruding L1 at its end. A universal biotinylated (●) oligonucleotide ($L_1'$) is ligated to the hairpinned product in the same reaction permitting separation of biotin-bearing ligation products from unligated oligonucleotide probes by streptavidin selection. The oligonucleotide probes can also be made sufficiently long, e.g., by including so called spacers between tags (C1/C1) and the primer-specific portions of the oligonucleotides (A1/B1) so that ligation of the biotinylated oligonucleotide occurs while portions of the oligonucleotide probes are annealed to the target. Alternatively, one can increase the temperature to melt the ligated product off the target, and then lower the temperature to enable hairpin formation of the product and ligation of the biotinylated oligonucleotide to the hairpinned product. In either event, the separated ligation products are subsequently amplified in the presence of a polymerase and oligonucleotide primers as described above.

The key feature for the oligonucleotide probe designs shown in FIGS. 4A-4C to work is that the intramolecular hairpins are thermodynamically much more stable than bimolecular interactions between oligonucleotide probes. Temperature and buffers are selected so that a very small percentage of unligated oligonucleotide probes with complementary tags and will be annealed to each other, but close to 100% of ligated molecules will form a hairpin structure.

In another embodiment of the present invention, unligated oligonucleotide probes are removed using gel filtration (e.g., Sephadex) or a similar method to separate longer, higher molecular weight ligated products from shorter unligated oligonucleotide probes. Yet another approach for removing unligated probes prior to PCR amplification of ligated product sequences involves ligation product immobilization on a solid support (e.g., using zip-code capture as described supra) and washing away the unligated oligonucleotide probes.

Figure 5:
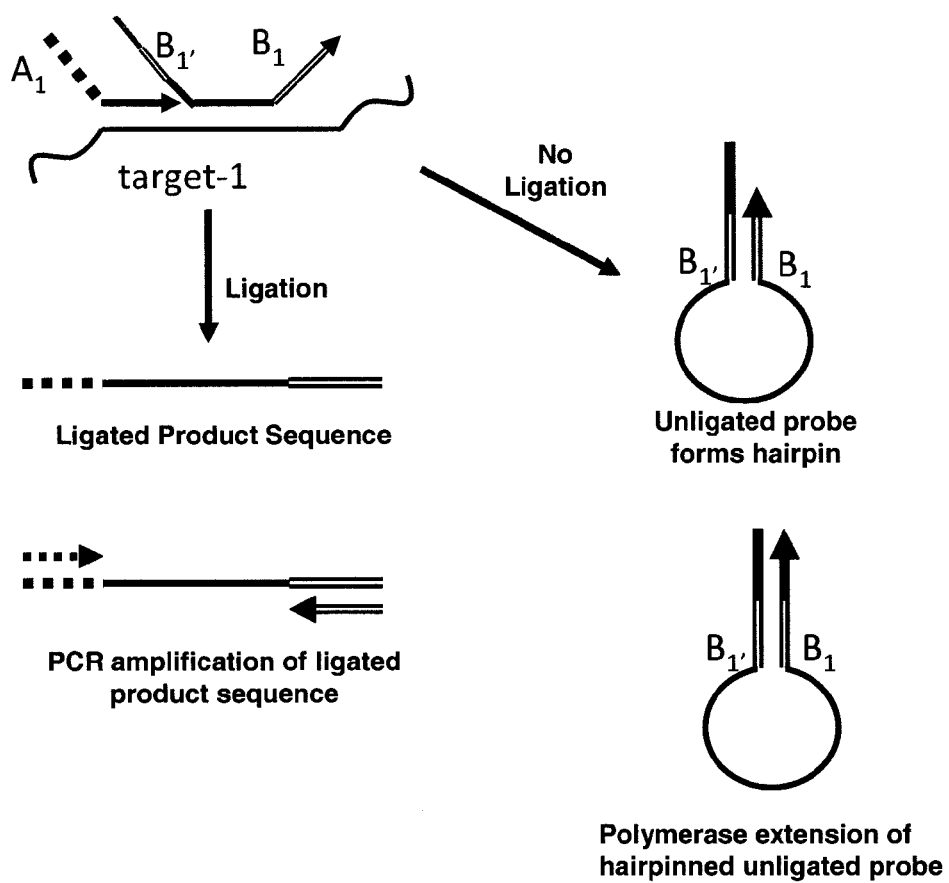
FIG. 5 is a schematic showing an oligonucleotide probe design that facilitates separation of unligated oligonucleotide probes from ligation products to occlude extension or amplification of the unligated oligonucleotide probe in the amplification phase following ligation. In this design, the second oligonucleotide probes have complementary tags $B_1$ and $B_1$'. During nuclease-ligation, complementary secondary oligonucleotide probes do not form significant hairpins because the annealing temperature is set too high to permit a stable intramolecular stem forming. Following nuclease-ligation, the temperature is decreased permitting unligated second oligonucleotide probes to form an intra-molecular annealing between $B_1$ and $B_1$'. The 3' end of unligated oligonucleotide $B_1$ extends forming a highly thermodynamically stable stem. Unligated oligonucleotides form panhandles that are no longer able to participate in PCR primer extension.

In yet another embodiment of the present invention, unligated oligonucleotide probes are occluded from subsequent extension and amplification by designing probes that are capable of forming stable hairpin structures in the absence of ligation. This embodiment is depicted in FIG. 5. In accordance with this embodiment, the second oligonucleotide probe further comprises a nucleotide flap that is 5' to the overlapping identical nucleotide at the junction, wherein at least a portion of the nucleotide flap ($B_1'$ in FIG. 5) is complementary to at least a portion of the 3' primer-specific portion of the second oligonucleotide probe ($B_1$ in FIG. 5). In the absence of ligation, complementary regions of the nucleotide flap ($B_1'$) and the 3' primer-specific portion ($B_1$) of unligated second oligonucleotide probes hybridize to each other to form hairpinned second oligonucleotide probes (FIG. 5, right-hand side). The 3' primer-specific portion ($B_1$) of the hairpinned second oligonucleotide probe is extended during the first PCR cycle to form an extended hairpinned second oligonucleotide probe that occludes binding of the second oligonucleotide primer to its complementary sequence. As shown in the left-hand side of FIG. 5, ligation products that are formed are subsequently amplified using PCR without interference from the unligated probes.

During the nuclease-ligation process the temperature is relatively high (50-70° C.) permitting the second oligonucleotide to participate in the nuclease-ligation reaction using thermostable enzymes with combined or separate 5' nuclease and ligase activities, e.g., Taq polymerase and Taq ligase, respectively, and inactivated (extension-blocked) dNTPs (TriLink). Once ligation is complete, the temperature increases to 95° C. inactivating dNTPs and/or polymerase.

Next, the temperature rapidly decreases, so that unligated second oligonucleotide probes form hairpins (FIG. 5, right-hand side). The 3' end of the hairpin structure is extended by polymerase, forming a longer and highly stable hairpin stem (FIG. 5, right-hand side) that prevents primers priming on unligated second oligonucleotide probes during PCR. The main advantage of this approach is that it enables a "closed tube" ligation PCR detection: sample DNA, nuclease-polymerase, ligase, oligonucleotide probes and primers, dNTPs and other reagents required for nuclease, ligation, and PCR can be preloaded in a well or droplet. The reaction switches from a nuclease-ligation to PCR amplification by heat activation of one or several reagents required for PCR.

Figure 6:
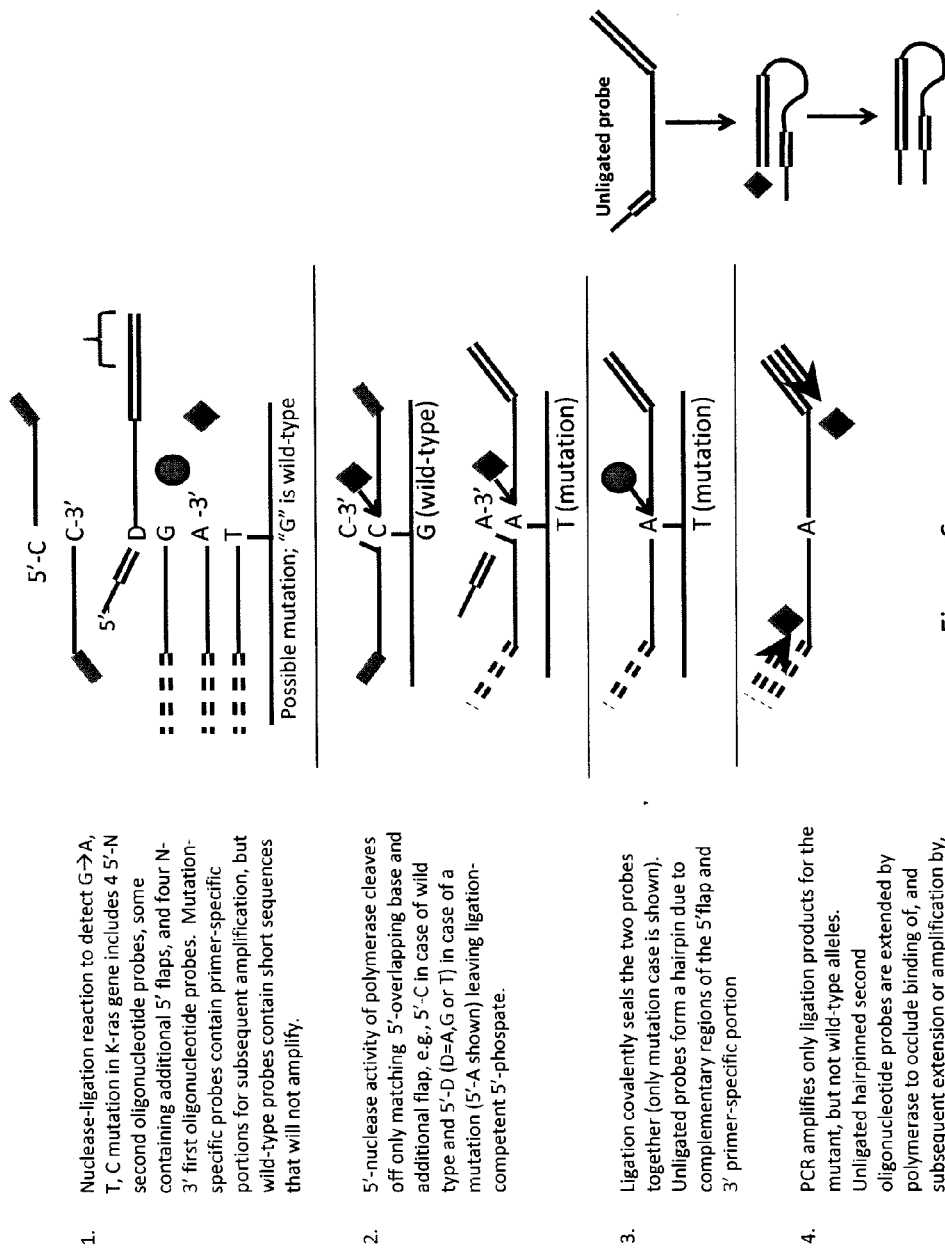
FIG. 6 shows nuclease-ligation-PCR process of the present invention to detect multiple single-base mutations in a target nucleotide sequence.

FIG. 6 depicts the nuclease-ligation-PCR process of the present invention to detect G→A, T, C mutation in K-ras gene. This reaction involves four 5'-N second oligonucleotide probes, some containing nucleotide flaps 5' to the overlapping identical nucleotide at the junction. At least a portion of the nucleotide flap on the second oligonucleotide probes is complementary to the 3' primer-specific portion of the probe to facilitate hairpin formation in the absence of ligation. The reaction also involves four N-3' first oligonucleotide probes. In this example, mutation-specific oligonucleotide probes contain 3' and 5' primer-specific portions for subsequent amplification, but wild-type specific oligonucleotide probes contain short sequences that will not amplify. As shown in step 2, 5'-nuclease activity (♦) cleaves off only matching 5'-overlapping base and additional flap, e.g., 5'-C in case of wild type and 5'-D (D=A, G or T) in case of a mutation (5'-A shown) leaving ligation-competent 5'-phosphate on the second oligonucleotide probe. Ligase (●) covalently seals the two oligonucleotide probes together (only mutation case is shown) and PCR amplifies only ligation products for the mutant, but not wild-type alleles. As shown on the right-hand side of FIG. 6, unligated second oligonucleotide probes that were not cleaved and ligated form hairpins that are extended by polymerase to occlude binding of, and subsequent extension or amplification by, the secondary primer.

K-ras mutations, which include 6 changes on codon 12 and 1 change on codon 13 that are all spaced together, are particularly difficult to detect. To achieve high fidelity discrimination, the mismatch between mutant oligonucleotide probe and wild-type sequence should at least be C:A for the last base, not G:T. Fidelity can further be enhanced if the base at the penultimate position is either a C:A or G:T mismatch. Additionally, an optional upstream probe for wild-type sequence can be included which has a mismatch at the third position from the 3' side. Further, by making a mismatch in the third position, mutant first oligonucleotide probes will now mismatch in the last 3 positions on the 3' side, and consequently cannot accidentally PCR amplify residual normal LDR ligation product. The second oligonucleotide probe for the wild-type sequence will contain the wild-type base on the critical base. This probe will also lack a primer-specific region, and therefore will not allow for any amplification.

Since the different probes will compete with each other in binding the (rare) mutant sequence, it is important to allow for all the probes to hybridize to the correct sequence. There will be four upstream and four downstream probes for the K-ras codon 12 $1^{st}$ position mutations, giving 16 different possible combinations. To avoid false ligation/false signal by mutant probes to normal sequence, but also allow for correct ligations to occur in the presence of the mutant sequence, a "mini-cycling" approach can be employed. In this approach, the temperature is oscillated between 60° C. for ligation (10 minutes) and 75° C. (1 minute) so unligated probes but not ligated products fall off the template.

To summarize the various levels of discrimination that can be employed in the nuclease-ligation-PCR process using two primers for detection of each mutation include: (i) use of 5'-3' nuclease activity of polymerase or Fen nuclease to cleave only second oligonucleotide probes having an overlapping identical nucleotide at the junction with the first oligonucleotide probe to liberate a 5' phosphate allowing ligation to occur; (ii) use of 3' ligation fidelity of thermostable ligase on first oligonucleotide probe; (iii) use of mismatch or nucleotide analogue in the $2^{nd}$ or $3^{rd}$ base from the 3' end of first oligonucleotide probe; (iv) use of oligonucleotide probes with wild-type sequence to suppress ligation of oligonucleotide probes designed to detect mutant nucleotide sequences on the wild-type nucleotide sequence; (v) use of mini-cycling conditions to improve yields of product when mutation is present; and (vi) use of nucleotide flap on the 5' end of second oligonucleotide probes that, in the absence of ligation, form hairpins by hybridizing to complementary regions in the 3' primer-specific portions at lower temperature. Hairpin extension forms products that are not bound by PCR primers and therefore extension or amplification of unligated oligonucleotide probes is avoided.

Figure 7:
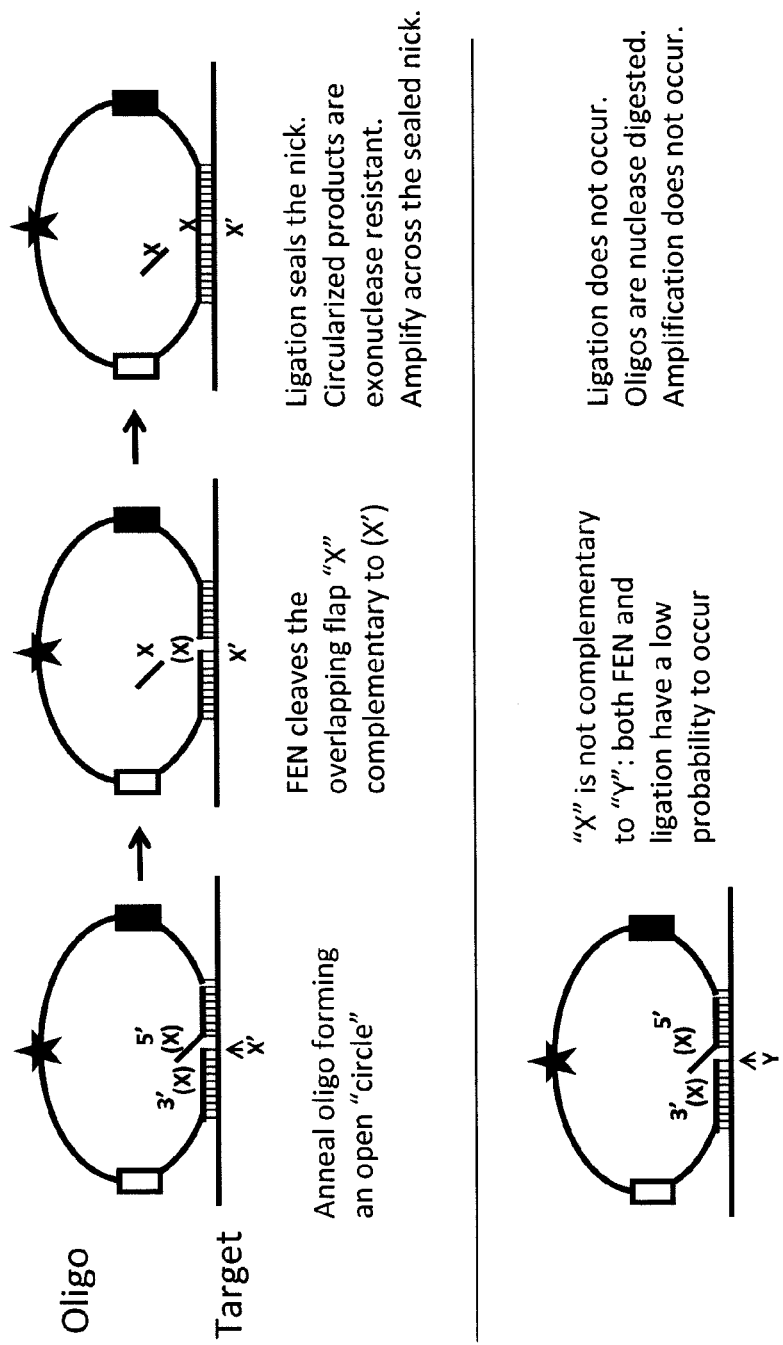
FIG. 7 shows FEN generated ligation substrate using coupled oligonucleotide probes (i.e., a circularizable probe) for multiplex LDR/PCR. A coupled oligonucleotide probe bearing a flap structure that matches the target SNP (arrow head) and the 3'OH terminating nucleotide produces a FEN cleavable substrate. The 3' OH of the circular oligonucleotide probe can ligate to FEN generated 5' phosphate generating a circular ligation product. Non-ligated uncircularized oligonucleotide probes can be digested using, e.g., exonucleases I, III, V, and 1. Optionally, the oligonucleotide probes can be internally cleaved at a scission domain (Star symbol), e.g., a dU tract targeted by UNG+heat=labile abasic phosphodiester stretch. Open and shaded rectangles of the circular probe represent universal PCR primer sites for PCR amplification of ligation product.

In an alternative embodiment of the present invention, the oligonucleotide probes of a probe set are tethered together to form a coupled probe as shown in FIG. 7. In accordance with this embodiment, the 5' end of the first oligonucleotide probe is coupled to the 3' end of the second oligonucleotide probe. Following hybridization of the target-specific portions of the couple probe to its target nucleic acid molecule, and nuclease cleavage of the 5' flap nucleotide, the coupled probe is ligated to form a circular ligated product sequence.

In accordance with this embodiment of the present invention, the discriminating base is the same base on the 3' end and the 5' end, or the last base before cleavage of a flap on the 5' end. The cycling conditions can be varied to determine the optimal time for efficient (i) 5' nuclease cleavage liberating a 5' phosphate when the downstream probe portion for a particular mutation has a perfect match hybridization, followed by (ii) ligation to the 3' end of the upstream probe portion, again provided there is a perfect match to the mutation base. At the same time, non-specific cleavage and ligation is minimized by reducing the time allowed for both reactions to occur before the temperature is raised to denature the primer from the incorrect template.

The coupled probes of the present invention can be designed to include all of the features described herein for the non-coupled probes, e.g., upstream/downstream primer regions, zip-code portions, UniTaq detection portions and primer portions, tag portions, etc. Additionally, the coupled probes can be designed to contain one or more of the following features. In one embodiment, the coupled probe contains a sequence or chemical link that blocks polymerase extension through that region, i.e., a polymerase blocker, thereby preventing replication of the whole circularized ligated product. In another embodiment, the coupled probes are designed to contain a sequence that is cleaved after ligation. Prior to that cleavage, unligated coupled probes (as well as input template DNA) are removed by exonuclease digestion. In another embodiment, the unligated coupled primers form hairpins at lower temperature and extend on themselves to form products that do not amplify (see FIG. 8). To facilitate hairpin formation, the coupled oligonucleotide probe comprises a segment that is complementary to the 3' target specific portion. In the absence of ligation, the 3' target specific portion of the coupled probed hybridizes to the complementary segment to form a hairpinned coupled oligonucleotide probe. Extending the 3'target-specific portion of the coupled hairpinned oligonucleotide probe during the first round of subsequent PCR forms an extended coupled hairpinned oligonucleotide probe that occludes binding of the second oligonucleotide primer to its complementary sequence. The advantage of this approach is that it removes unligated coupled probes from downstream amplification and detection processes without requiring any additional digestion (e.g., exonuclease digestion) steps.

Figure 8:
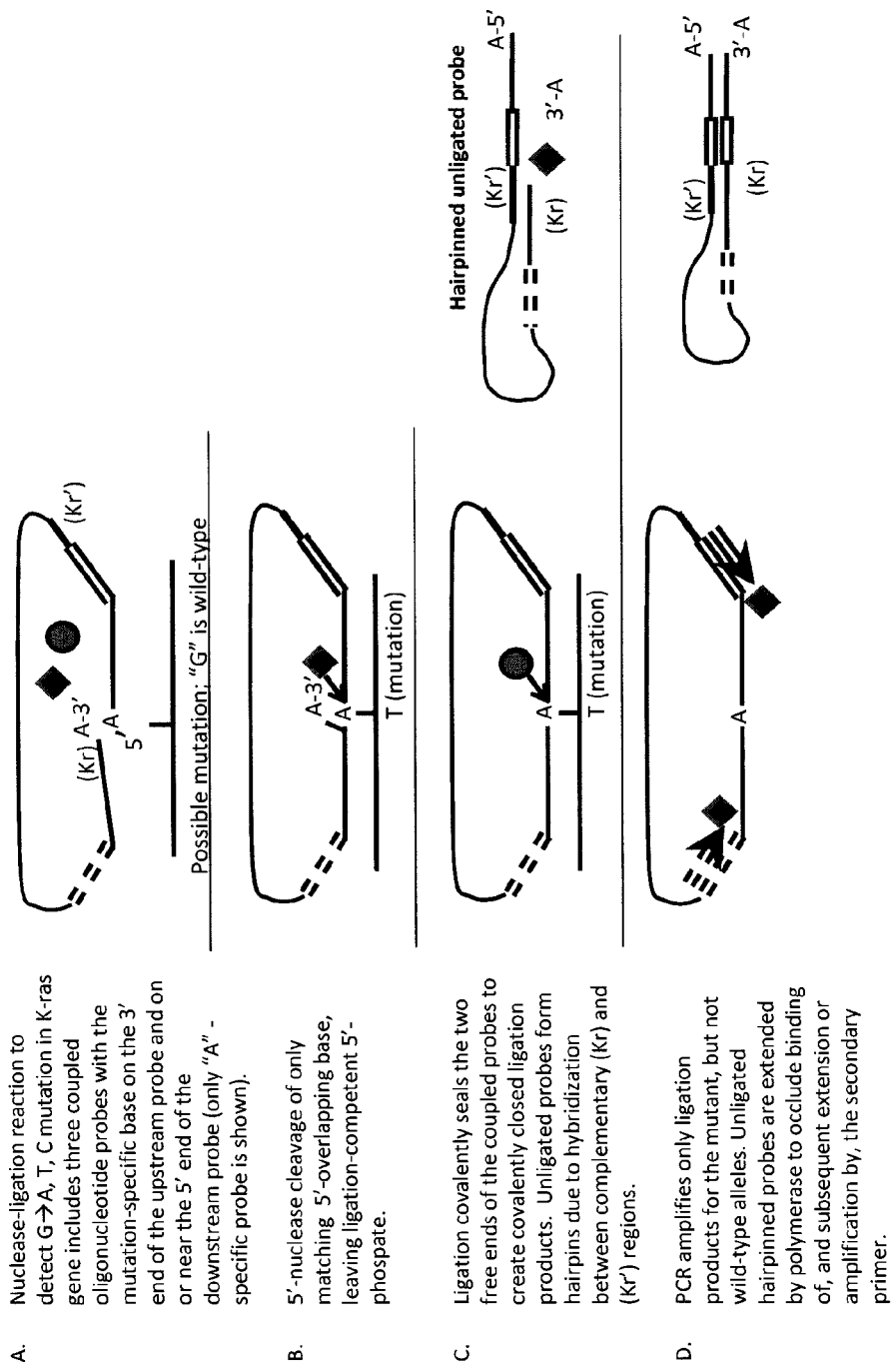
FIG. 8 shows an example of the nuclease-ligation-PCR process of the present invention utilizing coupled probes. In this example, only a probe to the mutant allele is shown, with the mutation-specific base on the 3' end of the upstream probe and on or near the 5' end of the downstream probe. FEN activity of a polymerase (♦) cleaves only a matching 5' overlapping base leaving a ligation competent 5'-phosphate, and a ligase (●) covalently seals the two free ends of the coupled oligonucleotide probes. PCR amplifies ligation products, in this case only mutant ligation products are produced (no wildtype ligation products are formed). The coupled probe also contains a segment (Kr') that is complementary to a region of the 3' target-specific portion (Kr). In the absence of ligation, the 3' target specific portion of the coupled probe hybridizes to the complementary segment (Kr') to form a hairpinned coupled oligonucleotide probe that is extended by polymerase to form a stable hairpin and thereby occluded from subsequent extension or amplification.

FIG. 8 shows the use of coupled probes in the nuclease-ligation-PCR process of the present invention to detect G→A, T, C mutation in K-ras gene. This approach utilizes three oligonucleotides containing two coupled probes with the mutation-specific base on the 3' end of the upstream probe and on or near the 5' end of the downstream probe (only "A"-specific oligonucleotide is shown). Mutation-specific oligonucleotides contain primer-specific portions for subsequent amplification. Only a matching 5'-overlapping base, e.g., in case of a mutation (5'-A shown), is cleaved by the 5'-nuclease activity leaving ligation-competent 5'-phospate. Cleavage may release only the single matching 5'-overlapping base (5'-A shown), or a flap containing that base at the liberated 3' end. Ligase (D) covalently seals the two free ends of the coupled oligonucleotide probes to create covalently closed circularized ligation products. PCR amplifies only ligation products for the mutant, but not wild-type alleles. As shown on the right-hand side of FIG. 8, unligated coupled probes form hairpins that are extended by polymerase to occlude binding of, and subsequent extension or amplification by, the secondary primer.

In summary, levels of discrimination that can be achieved using coupled probes include (i) use of 5'-3' nuclease activity of polymerase or Fen nuclease on downstream primer portion; (ii) use of 3' ligation fidelity of thermostable ligase on upstream primer portion; (iii) use of mismatch or nucleotide analogue in the $2^{nd}$ or $3^{rd}$ base from the 3' end of upstream primer portion; (iv) use of cycling conditions to improve specificity of generating ligation product only when mutation is present; (v) use of lower primer concentrations to minimize target-independent events; and (vi) use of sequences on the coupled primers, such that when they are not ligated, form hairpins at lower temperature and extend on themselves to form products that do not amplify.

Several means of detecting PCR amplified ligation products can be employed as described below.

In a first approach, one of the primers in an oligonucleotide primer set used for PCR amplification can further comprise a detectable label to create labeled primary extension products that can be detected and identified. This method of detection is suitable when the primer-specific portions of the ligation product are allele specific. U.S. Pat. Nos. 6,027,889, 6,797,470, 7,312,039, 7,320,865, 7332,285, 7,166,434, 7,429,453, 8,283,121 all to Barany, which are hereby incorporated by reference in their entirety, describe methods of detecting nucleic acid sequence difference using a coupled ligation detection and polymerase chain reactions.

Figures 9A, 9B, 9C:
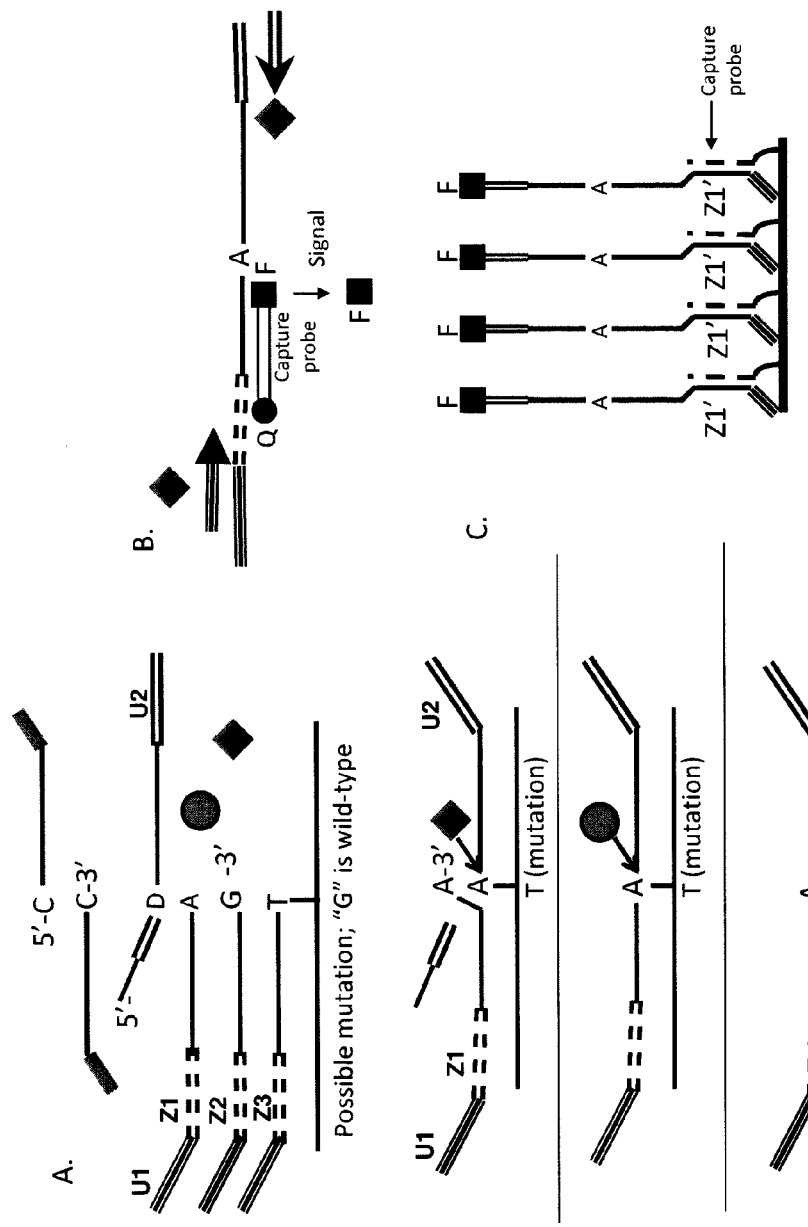
FIGS. 9A-9C show an example of the nuclease-ligation-PCR process of the present invention where detection of the resulting products is facilitated by a zipcode sequence.

In another approach, the first and/or second oligonucleotide probes in a probe set comprise a zip-code portion. As described above, zip-codes for different oligonucleotide probe sets have different nucleotide sequences (i.e., they are allele-specific) and hybridize to complementary capture oligonucleotides under uniform hybridization conditions. FIG. 9A depicts the nuclease-ligation-PCR process of the present invention to detect G→A, T, C mutation in K-ras gene. This reaction involves four 5'-N second oligonucleotide probes, some containing nucleotide flaps 5' to the overlapping identical nucleotide at the junction and an 3' primer-specific portion. To remove unligated oligonucleotide probes prior to PCR amplification, at least a portion of the nucleotide flap on the second oligonucleotide probes is complementary to the 3' primer-specific portion of the probe to facilitate hairpin formation in the absence of ligation. The reaction also involves four N-3' first oligonucleotide probes, each containing a different zip-code and a 5' primer-specific portion. In this example, mutation-specific oligonucleotide probes contain 3' and 5' primer-specific portions for subsequent amplification, but wild-type specific oligonucleotide probes contain short sequences that will not amplify. As shown in step 2, 5'-nuclease activity of the polymerase (♦) cleaves off only matching 5'-overlapping base and additional flap, e.g., 5'-C in case of wild type and 5'-D (D=A, G or T) in case of a mutation (5'-A shown) leaving ligation-competent 5'-phosphate on the second oligonucleotide probe. Ligase (●) covalently seals the two oligonucleotide probes together (only mutation case is shown), and PCR amplifies only ligation products for the mutant, but not wild-type alleles. Unligated second oligonucleotide probes that were not cleaved and ligated form hairpins that are extended by polymerase to occlude binding of, and subsequent extension or amplification by, the secondary primer.

Detection using the zipcode can be carried out using traditional Taqman™ detection as shown in FIG. 9B (see U.S. Pat. No. 6,270,967 to Whitcombe et al., and U.S. Pat. No. 7,601,821 to Anderson et al., which are hereby incorporated by reference in their entirety). For detection using Taqman assays, an optional first universal amplification reaction using universal PCR primers can be carried out to proportionately increase the ligation product in the sample (the universal PCR step is not shown in FIG. 9C). This is particularly suitable when detecting low abundance target nucleic acid sequences. After about 8-20 cycles of universal amplification, the sample would be diluted 10- to 100-fold and unique primers would be added that overlap with some or all of the unique zipcode sequence for each product. The Taqman probe would be for either the junction sequence of both zipcode and target DNA (as shown in FIG. 9C), or just the target DNA (without overlap of the unique primer in either case). The second primer can be universal (U2) or, for added specificity, it can be designed to include some genome-specific bases (without overlap to the Taqman probe). Signal is generated by 5' nuclease activity of polymerase when it extends the second primer. Primer extension cleaves the detectable label from the capture oligonucleotide releasing the detectable label from the quencher molecule, enabling detection.

Alternatively, for detection using universal (zipcode) arrays as shown in FIG. 9C, the second oligonucleotide primer (U2) would contain a reporter label, i.e. a fluorescent group, while the first oligonucleotide primer (U1) would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array as shown in FIG. 9C.

In addition, the above constructs can include unique sequence (ranging from 0 to 10 bases) internal to the Universal primers (Unique Ai, Unique Bi), represented as follows.

Univ.Primer U1—Unique Ai—Zipcode Zi—Target DNA—Unique Bi—Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the zipcode sequence.

Since each junction sequence between the zipcode identifier and target sequence is unique, the products of the initial universal amplification may also be identified and quantified using next-generation sequencing.

Another detection approach utilizing zipcodes involves having the zipcode portion split into two parts, which may be brought in proximity to each other using a short region of complementary sequence on both sides of the split parts. In particular, the first oligonucleotide probe would comprise a first portion of the zip-code and a first tag portion that is 3' to the first zip-code portion, and the second oligonucleotide probe would comprises a second portion of the zip-code and a second tag portion that is 5' to the second zip-code portion. The first and second tag portions of an oligonucleotide probe set are complementary to each other, and preferably between about 5 to 8 bases. This allows for transient hairpin formation at the short region when the two sections are on the same single strand of DNA, which is stabilized by hybridizing both halves of the zipcode sequence to a full length complementary zipcode sequence on an array, or alternatively as part of a Taqman assay.

Figure 10:
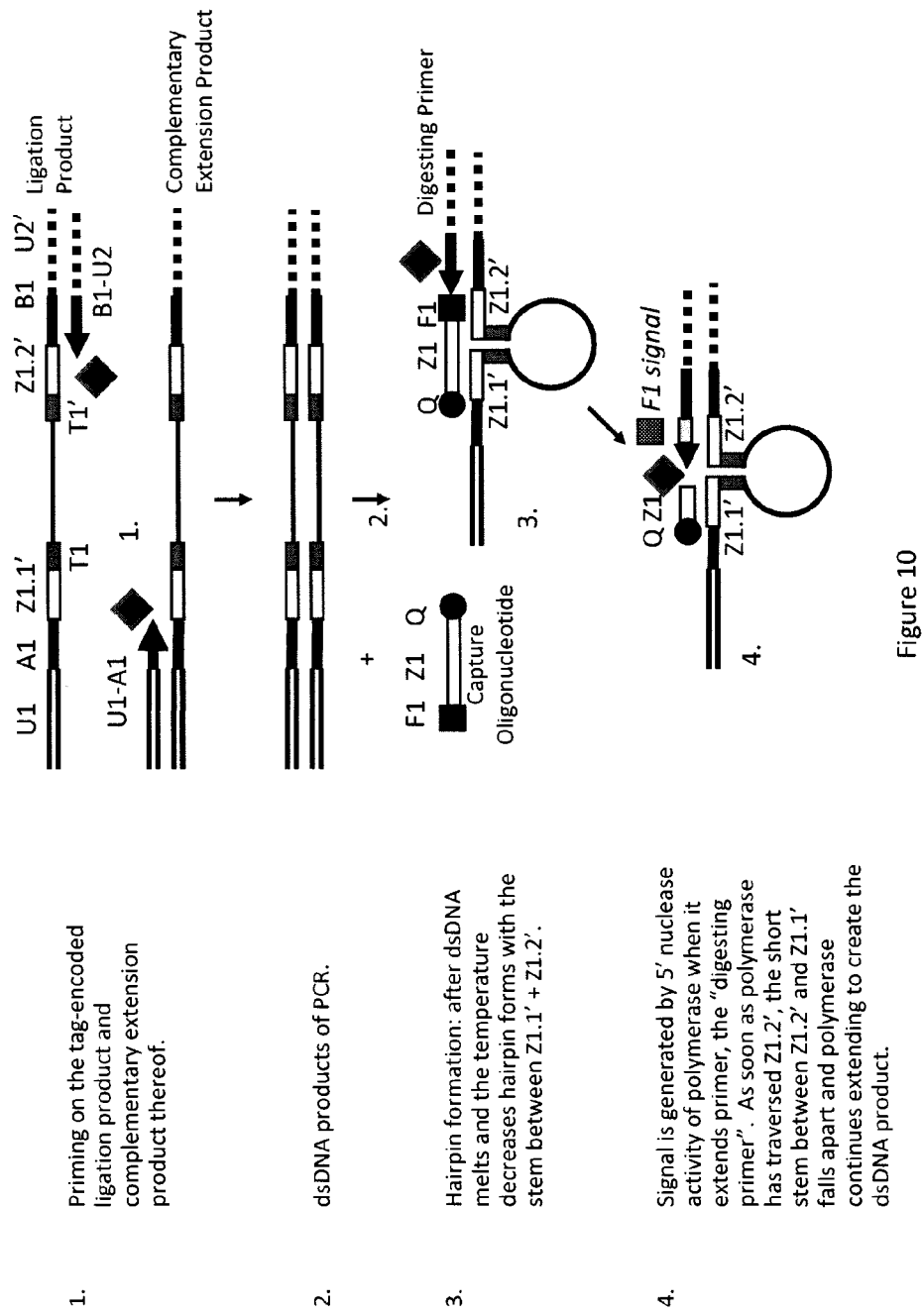
FIG. 10 shows an example of universal Taqman® split zip-code hairpin detection of products formed using the nuclease-ligation-PCR process of the present invention.

FIG. 10 shows an example of universal Taqman split zipcode hairpin detection. In this figure, and in accordance with the methods described above, a ligation product has already been formed using oligonucleotide probe sets (not shown) that comprise a first oligonucleotide probe having (i) a first 5'universal primer-specific portion (U1), (ii) a first short (1-10 bases) unique identifying sequence (A1), (iii) a first portion of a zip-code portion (Z1.1'), (iv) a first tag portion (T1) that is 3' to the first zip-code portion, and (v) a target-specific portion. The second oligonucleotide probe of the probe set has (i) a 3' universal primer-specific portion (U2'), (ii) a second short unique identifying sequence (B1), (iii) a second portion of a zip-code portion (Z1.2'), (iv) a second tag portion (T1') that is 5' to the second zip-code portion, and (v) a target-specific portion. As shown in FIG. 10, the A1 and B1 unique sequences serve to facilitate a target-specific PCR amplification of the ligation product sequence when the PCR primers that are utilized span the universal primer portion and the A1 and B1 portions, respectively. This target-specific PCR amplification can optionally be preceded by a universal PCR amplification reaction using primers that hybridize to the 5' and 3' universal primer-specific portions. A first universal amplification reaction is particularly suitable when detecting low abundance target nucleic acid sequences in a sample. Following the target-specific PCR amplification of the ligation products or extension products thereof (FIG. 10, Step 1), the double stranded DNA products are denatured (FIG. 10, Step 2). As the temperature decreases, the first and second tag portions (T1 and T1') transiently hybridize together, bringing the first portion of the zipcode sequence (Z1.1' from the first oligonucleotide probe) in proximity to the second zipcode sequence (Z1.2' from the second oligonucleotide probe). The transient hybridization is stabilized by the simultaneous hybridization of a labeled capture oligonucleotide (Z1) that is complementary to the adjacently positioned zipcode sequences (FIG. 10, Step 3). In one embodiment, the capture oligonucleotide has a quencher molecule (Q) and a detectable label (F) that are separated from each other, where the detectable label is quenched when in close proximity to the quencher molecule. Signal is generated by 5' nuclease activity of a polymerase as it extends a primer (i.e., the "digesting primer") that is bound to the universal primer-specific portion (U2), the unique B1 portion, or a combination thereof, and cleaves the hybridized capture oligonucleotide. Primer extension cleaves the detectable label from the capture oligonucleotide releasing the detectable label from the quencher molecule, enabling detection (FIG. 10, Step 4). As soon as polymerase has traversed Z1.2', the short stem between Z1.2' and Z1.1' falls apart and polymerase continues extending to create the dsDNA product. A wide variety detectable labels, i.e., fluorescent dyes are known in the art and commercially available, e.g., FAM, TET, JOE, VIC, HEX, CY3, TAMRA, TexasRed, CY5, ROX. Similarly, quencher molecules, e.g., MGB-NFQ, BHQ-[0123], ZEN quencher from IDT, are also well known to those skilled in the art.

A related aspect of the present invention is directed to a method for identifying a presence of one or more target nucleotide sequences in a sample. This method involves providing a sample potentially containing the one or more target nucleotide sequences and providing one or more oligonucleotide probe sets. Each probe set has (i) a first oligonucleotide probe comprising a 5' primer-specific portion, a first portion of a zip-code portion, a first tag portion that is 3' to the first zip-code portion, and a target-specific portion, and (ii) a second oligonucleotide probe comprising a 3' primer-specific portion, a second portion of the zip-code portion, a second tag portion that is 5' to the second zip-code portion, and a target-specific portion. The first and second zip-code portions of an oligonucleotide probe set, when adjacently positioned, form a full-length zip-code portion, and the first and second tag portions of an oligonucleotide probe set are complementary to each other. The sample and the one or more oligonucleotide probe sets are contacted under conditions effective for first and second oligonucleotide probes of a probe set to hybridize in a base specific manner to their corresponding target nucleotide sequences, if present in the sample, and first and second oligonucleotide probes of the one or more probe sets are ligated together to form ligated product sequences. This method further involves providing one or more oligonucleotide primer sets, each set comprising (a) a first oligonucleotide primer comprising the same nucleotide sequence as the 5' primer-specific portion of the ligated product sequence and (b) a second oligonucleotide primer comprising a nucleotide sequence that is complementary to the 3' primer-specific portion of the ligated product sequence. The ligated product sequences, the one or more oligonucleotide primer sets, and a DNA polymerase are blended to form a polymerase chain reaction mixture, and the polymerase chain reaction mixture is subjected to one or more polymerase chain reaction cycles thereby forming primary extension products. A collection of capture oligonucleotides that are complementary to a portion of the first zip-code portion and a portion of the second zip-code portion are provided. Each capture oligonucleotide of the collection for each different primary extension product has a different nucleotide sequence and comprises a quencher molecule and a detectable label separated from each other. The primary extension products and the collection of capture oligonucleotides are subjected to conditions effective for (i) the first and second tag portions of a particular primary extension product to hybridize to each other to form hairpinned extension products with adjacently positioned first and second zip-code portions and (ii) the capture oligonucleotides of the collection to hybridize to complementary adjacently positioned first and second zip-code portions of the hairpinned extension products. The quencher molecule or the detectable label is cleaved from hybridized capture oligonucleotides, and the detectable label separated from the quencher molecule is detected. The presence of the one or more target nucleotide sequences in the sample is identified based on this detection.

In accordance with this aspect of the present invention, the ligation reaction process can be a ligation reaction that is preceded by 5' nuclease cleavage of the second oligonucleotide probe, as described herein. Alternatively, ligation competent oligonucleotide probes can be provided and ligation does not need to be preceded by the 5' nuclease cleavage.

Figure 11:
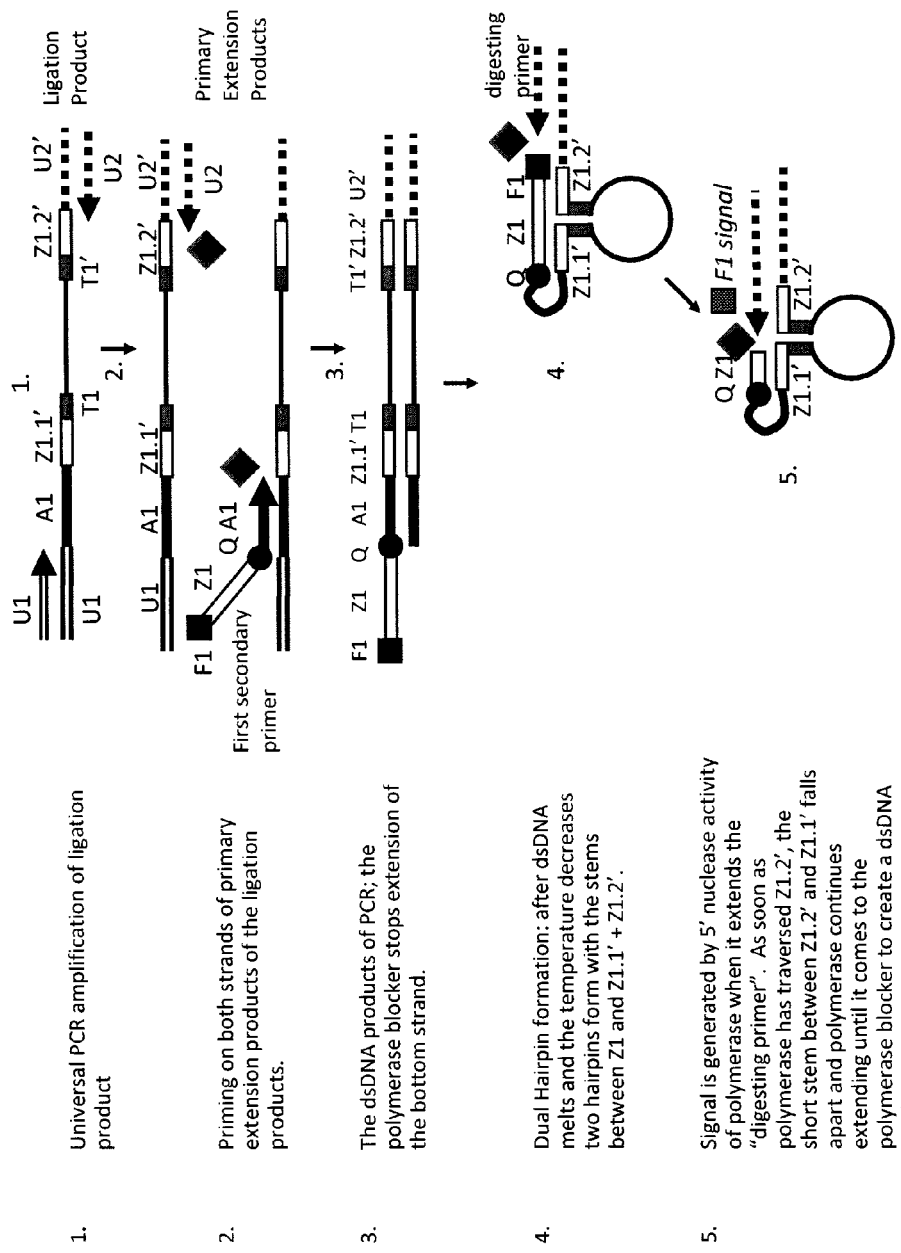
FIG. 11 shows an example of universal split zip-code hairpin detection of products formed using the nuclease-ligation-PCR process of the present invention.

FIG. 11 shows another example of universal split zipcode hairpin detection. In this figure, a ligation product has already been formed using oligonucleotide probe sets (not shown) that comprise a first oligonucleotide probe having (i) a first 5'universal primer-specific portion (U1), (ii) a second primer-specific portion (A1) that is a ligation product-specific primer portion, (iii) a first portion of a zip-code portion (Z1.1'), (iv) a first tag portion (T1) that is 3' to the first zip-code portion, and (v) a target-specific portion. The second oligonucleotide probe of the probe set has (i) a 3' universal primer-specific portion (U2'), (ii) a second portion of a zip-code portion (Z1.2'), (iii) a second tag portion (T1') that is 5' to the second zip-code portion, and (iv) a target-specific portion. In Step 1 of FIG. 11, the ligation product is optionally initially amplified using a universal oligonucleotide primer set, i.e., a first oligonucleotide primer (U1) having the same sequence as the 5' universal primer-specific portion of the ligation product, and a second oligonucleotide primer (U2) that is complementary to the 3' universal primer-specific portion of the ligation product. The primary extension products formed from the primary universal PCR step are subject to a secondary PCR step (FIG. 11, step 2) using a secondary primer set that includes a first secondary oligonucleotide primer having (a) a nucleotide sequence that is the same as the second primer-specific portion of the first oligonucleotide probe (A1), (b) a capture oligonucleotide portion (Z1) that is complementary to adjacently positioned first and second zip-code portions of an oligonucleotide probe set, (c) a quencher molecule (Q) and a detectable label (F) separated by said capture oligonucleotide portion. The second secondary oligonucleotide primer (U2) of the primer set has the same nucleotide sequence as the second primary oligonucleotide primer of the primary PCR (i.e., it is complementary to the 3' universal primer-specific portion of the ligation product). The quencher molecule of the first secondary primer can serve as a polymerase blocker to block polymerase extension of the bottom strand. Alternatively, a polymerase blocker such as HEG (hexethylene glycol), THF (tetrahydrofuran), Sp-18, or any other blocker known in the art that is sufficient to stop polymerase extension can be positioned proximal to the quencher moiety. The double stranded DNA products (shown in FIG. 11, Step 3) are denatured and the temperature decreased to allow dual hairpin formation with stems between Z1.1' and Z1.2' (stem formed by hybridization between T1 and T1') and between the capture oligonucleotide portion (Z1) and Z1.1'/Z1.2' (FIG. 11, Step 4). Signal is generated by 5' nuclease activity of polymerase when it extends a "digesting primer" complementary to the 5' universal primer-specific portion. Primer extension cleaves the detectable label (F) or the quencher molecule (Q) from the capture oligonucleotide releasing the detectable label (F) from the quencher molecule (Q), enabling detection (FIG. 11, Step 5). As soon as polymerase has traversed Z1.2', the short stem between Z1.2 and Z1.1' falls apart and polymerase continues extending until it comes to the polymerase blocker to create a dsDNA product similar to that in step 1, but lacking the fluorescent D1 signal.

Another aspect of the present invention is directed to a method for identifying a presence of and/or potential mutations within one or more target nucleotide sequences in a sample. This method involves providing a sample potentially containing the one or more target nucleotide sequences and providing one or more oligonucleotide probe sets. Each probe set has (i) a first oligonucleotide probe comprising a 5' primer-specific portion, a first portion of a zip-code portion, a first tag portion that is 3' to the first zip-code portion, and a target-specific portion, and (ii) a second oligonucleotide probe comprising a 3' primer-specific portion, a second portion of the zip-code portion, a second tag portion that is 5' to the second zip-code portion and a target-specific portion. The first and second zip-code portions of an oligonucleotide probe set, when adjacently positioned, form a full-length zip-code portion, and the first and second tag portions of an oligonucleotide probe set are complementary to each other. The sample and the one or more oligonucleotide probe sets are contacted under conditions effective for first and second oligonucleotide probes of a probe set to hybridize in a base specific manner to their corresponding target nucleotide sequences, if present in the sample, and the first and second oligonucleotide probes of the one or more probe sets are ligated together to form ligated product sequences. The method further involves providing one or more oligonucleotide primer sets, each set comprising (i) a first oligonucleotide primer having (a) a nucleotide sequence that is the same as the second primer-specific portion of the first oligonucleotide probe, (b) a capture oligonucleotide portion that is complementary to adjacently positioned first and second zip-code portions of an oligonucleotide probe set, (c) a quencher molecule and a detectable label separated by said capture oligonucleotide portion, (ii) a second oligonucleotide primer comprising a nucleotide sequence that is complementary to the 3' primer-specific portion of the ligated product sequence. The ligated product sequences, the one or more oligonucleotide primer sets, and a DNA polymerase are blended to form a polymerase chain reaction mixture and the polymerase chain reaction mixture is subjected to one or more polymerase chain reaction cycles thereby forming primary extension products. The primary extension products are subject to conditions effective for the first and second tag portions of a particular primary extension product to hybridize to each other to form hairpinned primary extension products with adjacently positioned first and second zip-code portions and (ii) the capture oligonucleotide portion of a particular hairpinned primary extension product to hybridize to complementary adjacently positioned first and second zip-code portions of the hairpinned extension product. The quencher molecule or the detectable label of the hairpinned primary extension products is cleaved, and the detectable label separated from the quencher molecule is detected. The presence of the one or more target nucleotide sequences in the sample is identified based on this detection In accordance with this aspect of the present invention, the ligation reaction process can be ligation reaction that is proceed by 5' nuclease cleavage of the second oligonucleotide probe as described herein. Alternatively, ligation competent oligonucleotide probes can be provided and ligation does not need to be preceded by the 5' nuclease cleavage.

An alternative approach to utilizing the zipcode/capture oligonucleotide sequences for detection involves the UniTaq approach. The UniTaq system is fully described in U.S. Patent Application Publication No. 2011/0212846 to Spier, which is hereby incorporated by reference in its entirety. The UniTaq system involves the use of two to three short (1-10 nucleotides) unique "tag" sequences, where at least one of the unique tag sequences (Ai) is present in the first oligonucleotide probe, and the second and third unique tag portions (Bi and Ci) are in the second oligonucleotide probe sequence. Upon ligation of oligonucleotide probes in a probe set, the resulting ligation product will contain the Ai sequence—target specific sequences—Bi sequence—Ci sequence. The essence of the UniTaq approach is that both oligonucleotide probes of a ligation probe set need to be correct in order to get a positive signal, which allows for highly multiplexed nucleic acid detection. For example, and as described herein, this is achieved by requiring hybridization of two parts, i.e., two of the tags, to each other.

In one embodiment of the present invention, the UniTaq tag portions of an oligonucleotide probe set is "allele-specific" and used to identify and distinguish individual ligated product sequences in a sample. In accordance with this embodiment, the UniTaq portions for each different ligated product sequence are different. This embodiment is particularly useful for detecting and distinguishing different allele mutations. In an alternative embodiment, where the goal is to simply detect the presence of a mutation in a gene or chromosome copy number, but the identity of the mutation or chromosomal region is not critical, the same UniTaq tag portions can be used to detect different ligation products. In either embodiment, incorporation of the UniTaq tags portions into one of the oligonucleotide probes of a probe set allows for highly multiplexed detection of various target sequences simultaneously.

Figures 12A, 12B:
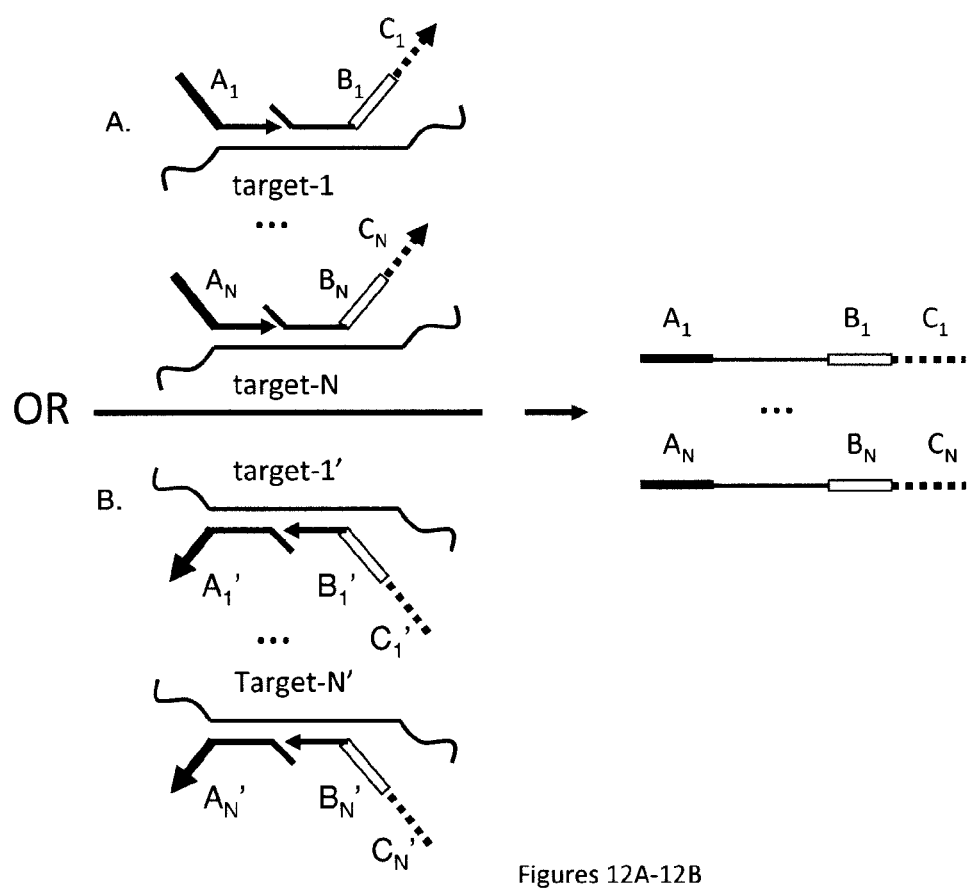
FIGS. 12A-12B show incorporation of UniTaq detection sequences into the nuclease-ligation proves and resulting products, and their utility for multiplex detection.

FIGS. 12A and 12B are schematics showing the incorporation of different Unitaq tag sets, e.g., Ai and Bi-Ci, i=1–N into oligonucleotide ligation probes and the resulting products. As shown in FIGS. 12A and 12B, the oligonucleotide probe sets can be designed to be complementary to the Watson or Crick strand of the genomic DNA.

Figures 13A, 13B, 13C:
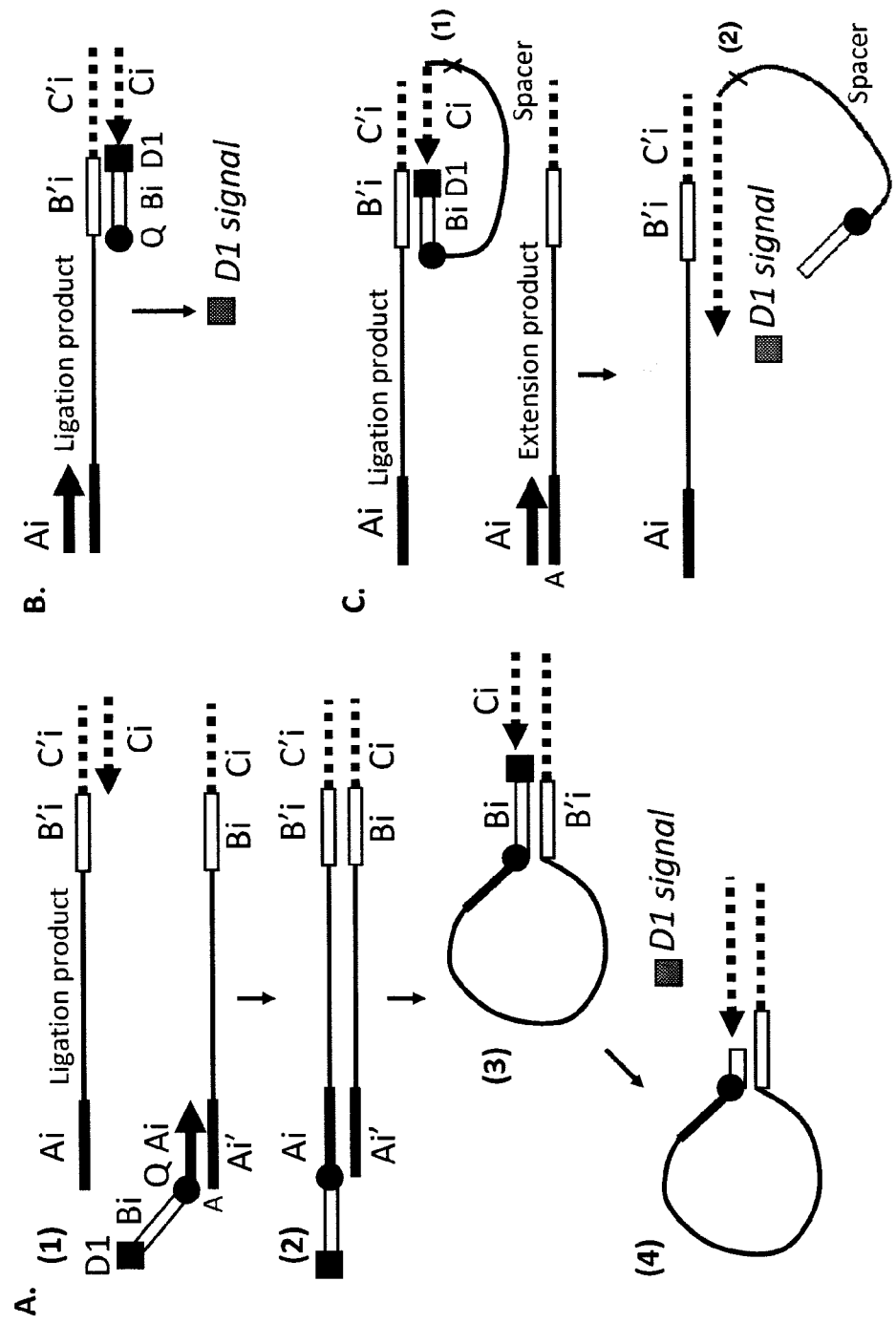
FIGS. 13A-13C show three examples for PCR detection of nuclease-ligase products of the present invention using (a) UniTaq mediate hairpin formation, (b) UniTaq 5'nuclease (AKA TaqMan) probes, and (c) UniTaq circle detection.

FIGS. 13A-13C show various ways in which the UniTaq tag system can be incorporated into the nuclease-ligation-PCR process of the present invention. In the first approach, shown in FIG. 13A, the ligation product containing Ai (a first primer-specific portion), B'i (a UniTaq detection portion), and C'i (a second primer-specific portion) is primed on both strands using a first oligonucleotide primer having the same nucleotide sequence as Ai, and a second oligonucleotide primer that is complementary to C'i (i.e., Ci). The first oligonucleotide primer also includes a UniTaq detection probe (Bi) that has a detectable label D1 on one end and a quencher molecule (Q) on the other end (D1-Bi-Q-Ai). Optionally positioned proximal to the quencher is a polymerase blocking unit, e.g., HEG, THF, Sp-18, or any other blocker known in the art that is sufficient to stop polymerase extension. A polymerase blocker may not be required if the 5'-tail that folds into a stem has one or more bases at the 5' end that are not complementary to the middle universal tag sequence, so that the hairpin formed by the opposite strand of DNA (with the 3'-end at the end of the stem) is not extendable during PCR. One can also design a small hairpin into the 5' portion of the primer 100, so that the dye and the quencher are brought closer together, similar to "Sunrise" primers and probes to improve quenching and decrease background fluorescence. For example, see U.S. Pat. Nos. 5,866,336 and 6,270,967, which are hereby incorporated by reference in their entirety.

PCR amplification results in double stranded product (FIG. 13A, step 2). In this example, a polymerase blocking unit prevents a polymerase from copying the 5' portion (Bi) of the first universal primer, such that the bottom strand of product cannot form a hairpin when it becomes single-stranded. Formation of such a hairpin would result in the 3' end of the stem annealing to the amplicon such that polymerase extension of this 3' end would terminate the PCR reaction.

The double stranded PCR products are melted (e.g., by raising the temperature to approximately 95° C. to separate the upper strand from the lower strand, and when the temperature is subsequently decreased, the upper strand of product forms a hairpin having a stem between 5' portion (Bi) of the first oligonucleotide primer and portion B'i at the opposite end of the strand (FIG. 13A, step 3). Also during this step, the second oligonucleotide primer anneals to the 5'-primer specific portion (C'i). Intra-molecular hairpin formation occurs rapidly and is driven by thermodynamics: the free energy is determined by stem length, GC-content and loop length. It is important that the melting temperature (Tm) of the hairpin be significantly higher (e.g., approximately 10° C. or higher) than the Tm of the second oligonucleotide primer. This way, when the temperature is decreased, nearly 100% of the molecules will form the hairpin before the second universal primer anneals and is extended. Upon extension of the second universal primer in step 4, 5' nuclease activity of the polymerase cleaves the detectable label D1 or the quencher molecule from the 5' end of the amplicon, thereby increasing the distance between the label and the quencher or FRET dye and permitting detection of the label. A wide variety fluorescent dyes are known in the art and commercially available, e.g., FAM, TET, JOE, VIC, HEX, CY3, TAMRA, TexasRed, CY5, ROX. Similarly, suitable quencher molecules, e.g., MGB-NFQ, BHQ-[0123], ZEN quencher from IDT, are well known to those skilled in the art.

In the approach shown in FIG. 13B, a traditional Taqman™ assay is used to detect the ligation product. This method involves providing a UniTaq detection probe (Bi) that is complementary to the UniTaq detection portion (B'i). The UniTaq detection probe comprises a quencher molecule (Q) and a detectable label (D1) that are separated from each other. The UniTaq detection probe hybridizes to its complementary UniTaq detection portion on the ligation product at the same time the second oligonucleotide primer (Ci) hybridizes to the 5' C'i primer-specific portion of the ligation product during PCR amplification. Extension of the second oligonucleotide primer generates a signal by 5' exonuclease cleavage of D1 and separation of D1 from the quencher.

A further example detection format involving the formation of a universal circle is schematically illustrated in FIG. 13C. As above, the ligation product in FIG. 13C contains Ai (a first primer-specific portion), target-specific portions, B'i (a UniTaq detection portion), and C'i (a second primer-specific portion). The ligation product is amplified using a first oligonucleotide primer (Ai) that has the same nucleotide sequence as the Ai primer specific portion of the ligation product, and a second oligonucleotide primer that includes (i) primer portion (Ci) that is complementary to the 5' C'i primer specific portion of the ligation product, (ii) a spacer region containing a polymerase blocker (x), (iii) a quencher molecule (Q), (iv) a UniTaq detection probe (Bi), and (v) a detectable label (D1) that is quenched when in close proximity to the quencher molecule. During PCR, the primer portion of the second oligonucleotide primer (Ci) anneals to primer-specific portion of the ligation product while the UniTaq detection probe (Bi) hybridizes to its complementary UniTaq detection portion of the ligation product (FIG. 13C, Step 1). In this example, extension of the second oligonucleotide primer (FIG. 13, Step 2) cleaves the hybridized UniTaq detection probe (Bi) thereby releasing the detectable label. The release of the detectable label from the quencher molecule generates a detectable signal.

Figure 14:
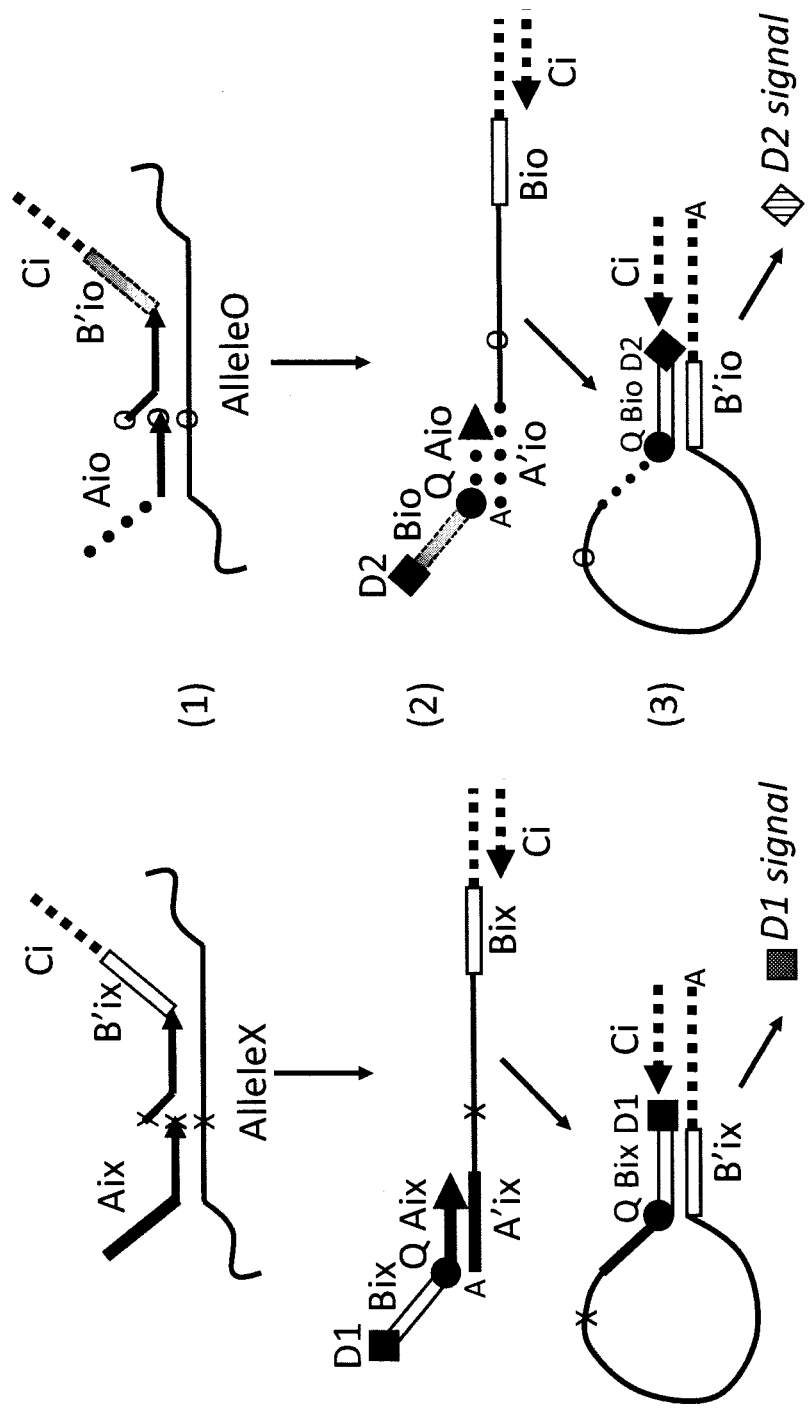
FIG. 14 show detection of two alleles "X" and "O", e.g., for a SNP is shown.

FIG. 14 shows example of detection for two alleles using the same process as depicted in FIG. 13A. Two alleles "X" and "O" are shown. Unlike regular LDR reactions, both oligonucleotide probes of a probe set are allele-specific. In other words, the probe set comprising a first oligonucleotide probe having a 5'primer specific portion (Aix) and a target specific portion, and a second oligonucleotide probe having a 3' primer specific portion (Ci), the UniTaq detection portion (Bix), and a target-specific portion is specific for detection of Allele X. Likewise, the probe set comprising a first oligonucleotide probe having a 5' primer specific portion (Aio) and a target specific portion, and the second oligonucleotide probe having a 3' primer specific portion (Ci), the UniTaq detection portion (Bio), and a target-specific portion is specific for detection of Allele O. Step 1 in FIG. 14 shows the nuclease-ligation process of the present invention. This oligonucleotide probe design format increases detection specificity: the 5'-FLAP base in the second oligonucleotide probe is cleaved only if the 5' base matches the allele and both oligonucleotide probes are ligated only if the 3' most base in the first oligonucleotide probe matches the allele. This method is especially advantageous to detect mutation detection, e.g., to detect rare somatic mutations in vast excess of wild-type molecules. Allele and mutation specific nuclease-ligase reactions can be performed at a temperature similar or higher than ligation probe $T_m$, so that mismatch oligonucleotides can melt off the template and allow new oligonucleotides to anneal. In case of mutation detection, one can use only oligonucleotide probes specific for the mutations and not the normal alleles. Steps 2 and 3 of FIG. 14 show the same process depicted in FIG. 13A, where the ligation product is amplified using a primer set having a first oligonucleotide primer that contain the UniTaq detection probe portion (Bix or Bio) containing a quencher molecule (Q) and a detectable label (D1 or D2) (Step 2). The resulting extension product forms a hairpin as a result of hybridization between the UniTaq detection probe portions (Bix or Bio) and complementary UniTaq detection portions (B'ix and B'io, respectively) (Step 3). A detectable signal is generated by 5' nuclease activity of a polymerase that cleaves the detectable label (D1 or D2) from the UniTaq detection probe portion (Bix or Bio) of the hairpinned product as it extends a hybridized primer (Ci) (Step 3).

Figure 15:
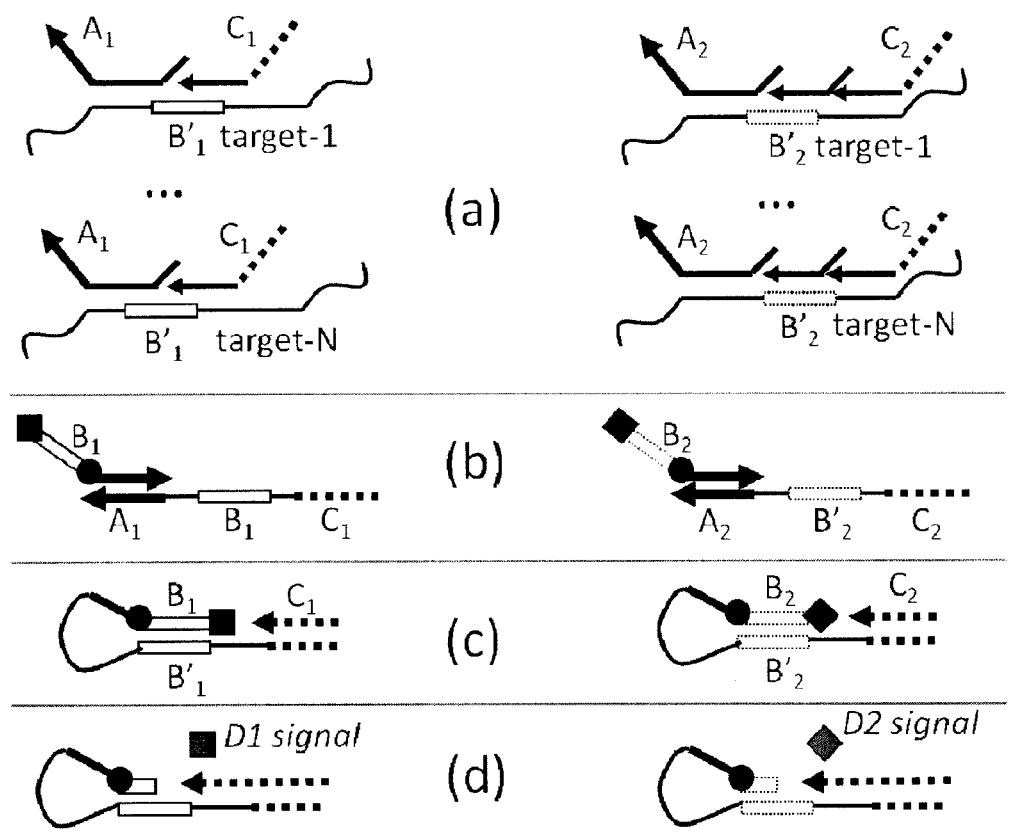
FIGS. 15A-15D show the detection of two target sets, e.g., for fetal aneuploidy for T21 as an example.

FIG. 15 shows an example of using universal naturally occurring "tags" for detection. This method can be used when there is sufficient freedom to pick detection targets and there is a need to increase detection sensitivity and robustness. Fetal aneuploidy detection of Down's syndrome allows to picking multiple loci (N in FIG. 15A) on chromosome 21 that all have the same universal sequence B1, e.g., an 8-mer. One can optionally use the same universal 8-mer middle oligonucleotide for all targets. In this case, one can use hybridization stabilizing modified bases in this universal middle oligonucleotide, e.g., LNA. The ligation oligonucleotide probes are designed to ligate at the ligation points close to the middle of the universal tags. Alternatively, ligation oligonucleotides can be designed so that universal B1 tags occur anywhere in the ligation products.

FIG. 15A on the right shows how a double ligation design can be used; in this case a different universal tag B2 is present in all N control targets. Universal detection using dual-labeled primers will detect all targets with B1 tags in dye D1 and all targets with B2 tags in dye2. This approach of using the same universal sequence for detecting a first chromosome (i.e. chromosome 21) and a different universal sequence for detecting a second chromosome (i.e. control chromosome 2) may be used for non-invasive prenatal diagnosis. The individual ligation products are "counted" using digital PCR (dPCR). In case of dPCR, the counts of wells with D1 and D2 signal can be used to detect fetal aneuploidy.

Another aspect of the present invention is directed to a method for identifying a presence of one or more target nucleotide sequences in a sample. This method involves providing a sample potentially containing the one or more target nucleotide sequences and providing one or more oligonucleotide probe sets. Each set comprises (a) a first oligonucleotide probe having a target-specific portion, and (b) a second oligonucleotide probe having 5' non-target specific flap portion and a target-specific portion containing one or more thiophosphate-modified nucleotide bases, wherein the first and second oligonucleotide probes of a probe set are configured to hybridize on the target nucleotide sequence. The sample and the one or more oligonucleotide probe sets are contacted under conditions effective for first and second oligonucleotide probes of a probe set to hybridize in a base specific manner to their corresponding target nucleotide sequences, if present in the sample. The 5' non-target specific flap portion of the second oligonucleotide probe is cleaved with an enzyme having 5' nuclease activity, thereby liberating a 5' phosphate at a first nucleotide base of the target-specific portion of the second oligonucleotide, and the first and second oligonucleotide probes of the one or more oligonucleotide probe sets are ligated together to form ligated product sequences containing the target-specific portions with the one or more thiophosphate-modified nucleotide bases. The method further comprises detecting ligated product sequences in the sample and identifying the presence of the one or more target nucleotide sequences in the sample based on said detecting.

In accordance with this aspect of the present invention, at least one of the one or more thiophosphate-modified nucleotide bases of the second oligonucleotide probe is adjacent to the first target-specific nucleotide base.

Figure 16:
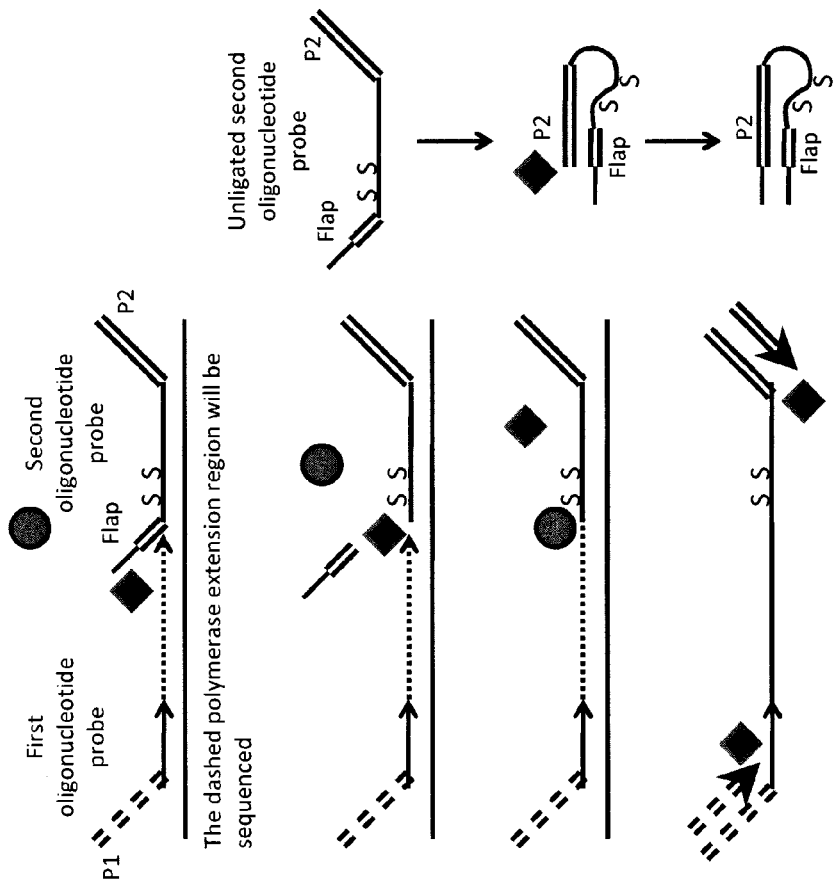
FIG. 16 shows detection of unknown mutations by primer extension, single base strand displacement, 5'-nuclease cleavage to generate 5'-phosphate, ligation, and PCR amplification. The second oligonucleotide probe contains one or more thiophosphate-modified nucleotides ("s") that are resistant to 5' nuclease cleavage.

In accordance with this aspect of the present invention, the oligonucleotide probes of a probe set may comprise target-specific portions that are in close proximity to each other on a target nucleic acid molecule and are configured to hybridize adjacent to one another on the target nucleotide sequence with a junction between them, as shown in FIG. 1. Alternatively, and as shown in FIG. 16, the oligonucleotide probes of a probe set may comprise target-specific portions that are not adjacent to each other. In accordance with this embodiment, the first oligonucleotide probe is extended with a polymerase to form a junction with the second oligonucleotide probe prior to cleaving the 5' non-target specific flap portion (flap) of the second oligonucleotide probe, i.e., gap-ligation reaction (Jou et al., "Deletion Detection in Dystrophia Gene by Multiplex Gap Ligase Chain Reaction and Immunochromatographic Strip Technology," *Human Mutation* 5:86-93 (1995), which is hereby incorporated by reference in its entirety). Cleavage occurs if the target specific portion of the second oligonucleotide probe has an overlapping identical nucleotide at the junction with the extended first oligonucleotide probe. Further 5' nuclease activity is halted by the thiophosphate-modified nucleotides ("S") of the second oligonucleotide probe. Following cleavage by the 5' nuclease activity of the polymerase (♦), the extended first oligonucleotide probe is ligated to the second oligonucleotide probe by a ligase (●). In the embodiment depicted in FIG. 16, the first oligonucleotide probe further comprise a 5' primer-specific portion (P1) and the second oligonucleotide probe comprises a 3' primer-specific portion (P2). Accordingly, following ligation, the ligated product is subsequently PCR amplified and/or subject to sequencing. Unligated second oligonucleotide probe sequences can be occluded from interfering with PCR amplification of the ligation products by designing the 5' flap portion of the oligonucleotide probe to be complementary to a portion of the 3' primer-specific portion. As shown in FIG. 16 (right-hand side), unligated oligonucleotide probes form a hairpin as a result of hybridization between the 5'flap portion and its complementary region in the 3' primer-specific portion. Extension of the 3' primer-specific portion of the hairpinned oligonucleotide probe forms a stable hairpin that will not be bound by a PCR oligonucleotide primer.

The various means for detecting the ligated product sequence are described supra, e.g., detection based on labeled ligation probes, next generation sequencing, PCR amplification and detection of labeled extension products containing zip-code portions and/or UniTaq detection portions. As described above, it is preferable to occlude unligated oligonucleotide probes from the sample comprising ligated product sequences prior to carrying out any subsequent amplification-based assays to prevent unligated probe extension or amplification. 5' nucleotide flap of the second oligonucleotide probe is complementary to at least a portion of the 3' primer-specific portion of the second oligonucleotide probe, and wherein, in the absence of ligation, complementary regions of the 5' nucleotide flap and the 3' primer-specific portion of an unligated second oligonucleotide probe hybridize to each other to form a hairpinned second oligonucleotide probe.

The challenge to develop reliable diagnostic and screening tests for both categories is to distinguish those markers emanating from the tumor or fetus that are indicative of disease (i.e. early cancer) vs. presence of the same markers emanating from normal tissue. There is also a need to balance the number of markers examined and the cost of the test, with the specificity and sensitivity of the assay. This is a challenge that needs to address the biological variation in diseases such as cancer. In many cases the assay should serve as a screening tool, requiring the availability of secondary diagnostic follow-up (i.e. colonoscopy, amniocentesis).

Compounding the biological problem is the need to reliably detect nucleic acid sequence mutations or reliably quantify DNA or RNA copy number from either a very small number of initial cells (i.e. from CTCs), or when the cancer or fetus-specific signal is in the presence of a majority of nucleic acid emanating from normal cells.

Finally, there is the technical challenge to distinguish true signal resulting from detecting the desired disease-specific nucleic acid differences, vs. false signal generated from normal nucleic acids present in the sample, vs. false signal generated in the absence of the disease-specific nucleic acid differences.

The methods of the present invention described herein provide solutions to these challenges. These solutions share some common themes highlighted below.

The first theme is multiplexing. PCR works best when primer concentration is relatively high, from 50 nM to 500 nM, limiting multiplexing. Further, the more PCR primer pairs added, the chances of amplifying incorrect products or creating primer-dimers increase exponentially. In contrast, for LDR probes, low concentrations on the order of 4 nM to 20 nM are used, and probe-dimers are limited by the requirement for adjacent hybridization on the target to allow for a ligation event. Use of low concentrations of gene-specific PCR primers or LDR probes with universal primer sequence "tails" allows for subsequent addition of higher concentrations of universal primers to achieve proportional amplification of the initial PCR or LDR products.

The second theme is fluctuations in signal due to low input target nucleic acids. Often, the target nucleic acid originated from a few cells, either captured as CTCs, or from tumor cells that underwent apoptosis and released their DNA as small fragments (200 bp) in the serum. Under such conditions, it is preferable to perform some level of proportional amplification to avoid missing the signal altogether or reporting inaccurate copy number due to fluctuations when distributing small numbers of starting molecules into individual wells (for real-time, or digital PCR quantification). As long as these initial universal amplifications are kept at a reasonable level (approximately 8 to 20 cycles), the risk of carryover contamination during opening of the tube and distributing amplicons for subsequent detection/quantification (using real-time, or droplet PCR) is minimized. If needed, carryover signal may be eliminated by standard uracil incorporation during the universal amplification step, and using UNG and AP endonuclease in the pre-amplification workup procedure.

The third theme is target-independent signal. This would arise from either polymerase or ligase reactions that occur in the absence of the correct target. Some of this signal may be minimized by judicious primer design. For ligation reactions, the 5'→3' nuclease activity of polymerase may be used to liberate the 5' phosphate of the downstream ligation primer (only when hybridized to the target), so it is suitable for ligation. Further specificity for distinguishing presence of a low-level mutation may be achieved by (i) using upstream LDR primers containing a mismatch in the $2^{nd}$ or $3^{rd}$ position from the 3'OH, and (ii) LDR primers to wild-type sequence that ligate but do not undergo additional amplification.

The fourth theme is either suppressed (reduced) amplification or incorrect (false) amplification due to unused primers in the reaction. One approach to eliminate such unused primers is to capture genomic DNA on a solid support, allow ligation primers to hybridize and ligate, and then remove primers or products that are not hybridized to the genomic DNA on a solid support. Another approach is to have the 3' end of downstream ligation primers hybridize to a portion of their own 5' end, to a sequence that is missing from the primer if it has undergone a successful nuclease cleavage and subsequent ligation step. Those primers that were not cleaved are self-extended to form longer hairpin loops that do not undergo further amplification. Still another approach is to use universal primer tails on either PCR or LDR genomic primers, which are slightly shorter than Universal primers. This allows initial universal amplification at a lower cycling temperature (i.e. 55° C. annealing) followed by higher cycling temperature (i.e. 65° C. annealing) such that the universal primers bind preferentially to the desired product (compared to composite PCR or LDR primers binding to incorrect products).

The methods of the present invention described herein are capable of detecting and quantifying one or more low abundance target nucleic acid molecules that have one or more nucleotide base insertions, deletions, translocations, mutations, and/or damaged nucleotide bases. As used herein "low abundance target nucleic acid molecule" refers to a target nucleic acid molecule that is present at levels as low as 1% to 0.01% of the sample. In other words, a low abundance nucleic acid molecule with one or more nucleotide base insertions, deletions, translocations, mutations and/or damaged nucleotide bases can be distinguished from a 100 to 10,000-fold excess of nucleic acid molecules in the sample having a similar nucleotide sequence as the low abundance nucleic acid molecules but without the one or more nucleotide base insertions, deletions, translocations, mutations, and/or damaged bases total nucleic acid sample using the methods of the present invention. In some embodiments of the present invention, the copy number of one or more low abundance target nucleotide sequences are quantified relative to the copy number from an excess of nucleic acid molecules in the sample having a similar nucleotide sequence as the low abundance nucleic acid molecules. In other embodiment of the present invention, the one or more target nucleotide sequences are quantified relative to other nucleotide sequences in the sample. In other embodiments of the present invention, the relative copy number of one or more target nucleotide sequences are quantified.

The low abundance target nucleic acid molecules to be detected can be present in any biological sample, including, without limitation, tissue, cells, serum, blood, plasma, amniotic fluid, sputum, urine, bodily fluids, bodily secretions, bodily excretions, cell-free circulating nucleic acids, cell-free circulating fetal nucleic acids in pregnant woman, circulating tumor cells, tumor, tumor biopsy, and exosomes.

With regard to early cancer detection, as described in the Prophetic Example herein, the methods of the present invention are suitable for detecting both repeat mutations in known genes (e.g., Braf, K-ras), and uncommon mutations in known genes (e.g., p53) when present at 1% to 0.01% of the sample. The methods of the present invention can also achieve accurate quantification of tumor-specific mRNA isolated from exosomes (e.g. a dozen expression markers that differentiate colon tumor tissue from matched normal mucosa), and tumor-specific miRNA isolated from exosomes or Argonaut proteins (e.g. a dozen microRNA markers that differentiate colon tumor tissue from matched normal mucosa). The methods of the present invention also afford accurate quantification of tumor-specific copy changes in DNA isolated from circulating tumor cells (e.g. a dozen copy changes that differentiate colon tumor tissue from matched normal mucosa), and the detection of mutations in DNA isolated from circulating tumor cells. (e.g. K-ras, B-raf, AKT, p53, BRCA1 genes).

The present invention is also capable of accurately quantifying (i) tumor-specific mRNA isolated from exosomes or circulating tumor cells, (ii) tumor-specific miRNA isolated from exosomes or Argonaut proteins, and (iii) tumor-specific copy changes in DNA isolated from circulating tumor cells that can predict outcome or guide treatment. The present invention can also detect mutations in DNA isolated from circulating tumor cells, e.g. K-ras, B-raf, AKT, p53, BRCA1 or other genes, that predict outcome or guide treatment.

With regard to prenatal diagnostics, the methods of the present invention are capable of detecting aneuploidy through counting copy number (e.g., Trisomy 21), inherited diseases containing common mutations in known genes (e.g. Sickle Cell Anemia, Cystic Fibrosis), inherited diseases containing uncommon mutations in known genes (e.g. familial adenomatous polyposis), inherited diseases arising from known or sporadic copy number loss or gain in known gene (e.g. Duchenne's muscular dystrophy), and paternity testing.

Another aspect of the present invention is directed to a kit for identifying a presence of one or more target nucleotide sequences in a sample. The kit contains an enzyme having 5' nuclease activity, a ligase, and one or more oligonucleotide probe sets. The oligonucleotide probe sets each have (a) a first oligonucleotide probe having a target-specific portion, and (b) a second oligonucleotide probe having a target specific portion, wherein the first and second oligonucleotide probes of a probe set are configured to hybridize adjacent to one another on the target nucleotide sequence with a junction between the first and second oligonucleotide probes, and where, in a probe set, the target specific portion of the second oligonucleotide probe has an overlapping identical nucleotide at the junction with the first oligonucleotide probe.

Another aspect of the present invention is directed to a kit for identifying a presence of one or more target nucleotide sequences in a sample. This kit contains an enzyme having 5' nuclease activity, a ligase, and one or more oligonucleotide probe sets. The oligonucleotide probe sets each have (a) a first oligonucleotide probe having a target-specific portion, and (b) a second oligonucleotide probe having 5' non-target specific flap portion and a target-specific portion containing one or more thiophosphate-modified nucleotide bases, where the first and second oligonucleotide probes of a probe set are configured to hybridize on the target nucleotide sequence.

PROPHETIC EXAMPLES

The following examples are provided to illustrate prophetic embodiments of the present invention but they are by no means intended to limit its scope Prophetic Example 1

Detection of Highly Sensitivity Mutation Marker (Present at 1% to 0.01%); Repeat Mutations in Known Genes Mutational changes in oncogenes are usually in discrete regions or positions and can often drive tumor progression. A list of these genes and their mutations may be found in public databases such as the Sanger Genome Center "COSMIC" database. Presence of such mutations in serum is a strong indicator of some tumor tissue in the body. Traditionally such mutations have been identified using allele-specific PCR amplification. This approach is susceptible to an initial false-amplification, followed by amplification of the false product. Others have used digital PCR to try to quantify mutant DNA in the serum.

Overview of approach: This approach depends on the fidelity of two enzymes: (i) the polymerase 5'→3' nuclease or flap cleavage enzyme in discriminating a match from mismatch on the 5' side of the downstream primer, and (ii) the ligase in discriminating a match from mismatch on the 3' side of the upstream probe. The later is enhanced further by using an intentional mismatch or nucleotide analogue in the $2^{nd}$ or $3^{rd}$ base from the 3' end that slightly destabilizes hybridization of the 3' end if it is perfectly matched at the 3' end, but significantly destabilizes hybridization of the 3' end if it is mis-matched at the 3' end. Finally, kinetic approaches, such as altering the cycling times and conditions can enhance the discrimination between wild-type and mutant template. Once a ligation event has taken place, those products will be amplified in a subsequent PCR amplification step, and thus this is the key discriminatory step.

The most difficult case is for K-ras mutations, where six changes on codon 12 and one change on codon 13 are all spaced together. In general, for highest fidelity, the mismatch between mutant primer and wild-type sequence should at least be C:A for the last base, not G:T. Thus, one needs to run both upper and lower strand primers, or two initial ligation tubes per reaction anyway. However, more than one mutation may be given the same UniTaq sequence or other detectable portion (zip-code, detectable label), since the aim is to find a mutation and not necessarily distinguish different mutations from each other.

The second issue is that the highest fidelity for ligation is achieved if the base at the penultimate position is either a C:A or G:T mismatch. This may reduce yields, but it improves fidelity.

A third issue is to also include an optional upstream probe for wild-type sequence, which has a mismatch at the third position from the 3' side. However, the upstream region will lack the UniTaq and Universal primer region, and, therefore, will not allow for any amplification. Further, by making a mismatch in the third position, mutant LDR probe will now mismatch in the last 3 positions on the 3' side, and consequently cannot accidentally PCR amplify residual normal LDR ligation product. The downstream probe for the wild-type sequence will contain the wild-type base on the critical base. This primer will also lack the UniTaq and Universal primer region, and therefore will not allow for any amplification.

Since the different primers will compete with each other in binding the (rare) mutant sequence, it is important to allow for all the probe to hybridize to the correct sequence. There will be 4 upstream and 4 downstream probe for the K-ras codon 12 $1^{st}$ position mutations, giving 16 different possible combinations. The goal is to avoid false ligation/false signal of mutant probe to normal sequence (hence the normal probe lacking UniTaq and Universal primer tails that will not amplify), but also have correct ligations occur in the presence of the mutant sequence. Thus, "mini-cycling" can be incorporated where the temperature is oscillated between 60° C. for ligation (10 minutes) and 75° C. (1 minute) so unligated probes but not ligated products fall off the template.

To summarize the levels of discrimination of the above approach using two probe for detection of each mutation:
1. Use of 5'-3' nuclease activity of polymerase or Fen nuclease on downstream probe.
2. Use of 3' ligation fidelity of thermostable ligase on upstream probe.
3. Use of mismatch or nucleotide analogue in the $2^{nd}$ or $3^{rd}$ base from the 3' end of upstream probe.
4. Use of probe with wild-type sequence to suppress ligation of mutant probe on wild-type DNA.
5. Use of mini-cycling conditions to improve yields of product when mutation is present.
6. Use of sequences on the 5' end of downstream oligonucleotide probe, such that when they are not cleaved, form hairpins at lower temperature and extend on themselves to form products that do not amplify.

An alternative approach (see below), using tethered or coupled matched upstream and downstream primers is also possible. Here, the discriminating base is the same base on the 3' end and the 5' end, or the last base before cleavage of a flap on the 5' end. The cycling conditions can be varied to determine the optimal time for efficient (i) polymerase 5'→3' nuclease cleavage liberating a 5' phosphate when downstream probe for a particular mutation has a perfect match hybridization, followed by (ii) ligation to the 3' end of the upstream probe, again provided there is a perfect match to the mutation base. At the same time, polymerase 5'→3' nuclease cleavage of the downstream probe if there is an incorrect base (i.e. a mismatch), followed by ligase incorrectly ligating an upstream probe (also with a mismatch) can be minimized by reducing the time allowed for both reactions to occur before the temperature is raised to denature the probe from the incorrect template.

There are two variations of coupled probes to consider. In the first variation, (shown in FIG. 8), the coupled primers are designed to (i) contain a sequence that blocks polymerase replication around the ligated product, and (ii) unligated coupled probe form hairpins at lower temperature and extend on themselves to form products that do not amplify.

To summarize the levels of discrimination of the first variation using coupled oligonucleotide probe for detection of each mutation:
1. Use of 5'→3' nuclease activity of polymerase or Fen nuclease on downstream probe portion.
2. Use of 3' ligation fidelity of thermostable ligase on upstream probe portion.
3. Use of mismatch or nucleotide analogue in the $2^{nd}$ or $3^{rd}$ base from the 3' end of upstream probe portion.
4. Use of cycling conditions to improve specificity of generating ligation product only when mutation is present.
5. Use of lower probe concentrations to minimize target-independent events.
6. Use of sequences on the coupled probe, such that when they are not ligated, form hairpins at lower temperature and extend on themselves to form products that do not amplify.

In a second variation, the coupled probes are designed to contain a sequence (e.g., dU tract targeted by UNG) that may be cleaved after the ligation step as shown in FIG. 7. Prior to that cleavage, unligated coupled primers (as well as input template DNA) are removed by exonuclease digestion.

To summarize the levels of discrimination of the first variation using coupled primers for detection of each mutation:
1. Use of 5'-3' nuclease activity of polymerase or Fen nuclease on downstream probe portion.
2. Use of 3' ligation fidelity of thermostable ligase on upstream probe portion.
3. Use of mismatch or nucleotide analogue in the $2^{nd}$ or $3^{rd}$ base from the 3' end of upstream probe portion.
4. Use of cycling conditions to improve specificity of generating ligation product only when mutation is present.
5. Use of lower primer concentrations to minimize target-independent events.
6. Use of exonucleases to destroy unligated probes and target.

As a control for the total amount of DNA present, one can choose a nearby target region. The upstream oligonucleotide that is ligated to the downstream is a mixture of two oligonucleotides: (i) An oligonucleotide present at 1 in 100 with the correct UniTaq specific sequence, and (ii) an oligonucleotide present at 99 in 100 with a sequence that has about 8-10 bases complementary to its 3' end. The ligation product containing the UniTaq sequences amplifies and will give a signal equivalent to 1 in 100 of the original template. The majority ligation product lacks the universal sequence on the 5' end, and does not amplify exponentially. Unligated upstream primer will form a hairpin back on itself, and extend its own 3' sequence on itself, taking it out of contention for becoming part of another PCR amplicon.

As a control for the total amount of DNA present, this approach may also be used with coupled probes, again on a nearby target region. One uses a mixture of two oligonucleotides: (i) An oligonucleotide present at 1 in 100 with the correct UniTaq and/or other tag sequence, and (ii) an oligonucleotide present at 99 in 100 with a sequence that either lacks or has incorrect tag sequences. The ligation product containing the UniTaq and/or tag sequences amplifies and will give a signal equivalent to 1 in 100 of the original template. The majority of ligation product either lacks or has incorrect tag sequences, and does not amplify exponentially.

Detailed Protocol: Highly Sensitive Detection of Mutation Marker (when Present at 1% to 0.01%), Repeat Mutations in Known Genes (See FIG. 6)

Step 1: Denature genomic DNA from serum (94° C. 1 minute) in the presence of first oligonucleotide probes ("upstream probes" containing 5' Universal Primer U1, followed by UniTaq Ai, followed by target-specific sequence with a C:A or G:T mismatch at the penultimate base, and the mutation base at the 3' end), second oligonucleotide probes ("downstream probes" containing 5' of 20 base extra overhang, where 8-10 bases are complementary to 3' end of Univ.Primer U2' sequence, followed by target-specific sequence—UniTaq Bi'—Univ.Primer U2'), Taq polymerase, and thermostable ligase (preferably from strain AK16D). Perform one or more ligation detection reactions, where the annealing temperature cycles one or more times between 60° C. for ligation (10 minutes) and 75° C. (1 minute). This will allow for ligation events to occur if mutant DNA is present.

Step 2: Add hot start dNTP's Universal Primer U1, Universal Primer U2. Incubate at 55° C. (activates dNTPs) to allow unligated downstream probes to self-hairpin to the 8-10 bases that are complementary to 3' end, which extends to create longer hairpins that render these downstream probes refractory to further amplification. Then, allow PCR amplification to proceed for 8-20 cycles. Ideally, the universal primer tails U1 and U2 on the LDR compound probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR probes binding to incorrect products). Further the universal primers U1 and U2 contain a short sequence in common (i.e. 6-10 bases) to avoid primer dimer formation. These conditions amplify fragments of the sequence:

Univ.Primer U1-UniTaq Ai—Upstream Target-Mutation-Downstream Target—UniTaq Bi'—Univ.Primer U2'

Step 3: Open tube, dilute 10- to 100-fold and distribute aliquots to Taqman wells, each well containing the following primers: Universal Primer U2 and UniTaq specific primers of the format F1-UniTaq Bi—Q—UniTaq Ai. (where F1 is a fluorescent dye that is quenched by Quencher Q). Under these conditions, the following product will form:

F1-UniTaq Bi—Q-UniTaq Ai—Upstream Target-Mutation-Downstream Target—UniTaq Bi'—Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

Highly sensitive mutation detection may be performed using Zipcode array, Zipcode Taqman or traditional Taqman detection as described supra. Briefly, this approach would use upstream first oligonucleotide probes (5' Universal Primer U1, followed by Zipcode Zi, followed by target-specific sequence with a C:A or G:T mismatch at the penultimate base, and the mutation base at the 3' end), and downstream second oligonucleotide probes (5' of 20 base extra overhang, where 8-10 bases are complementary to 3' end of Univ.Primer U2' sequence, followed by target-specific sequence—Univ.Primer U2'). After universal PCR amplification, these conditions amplify fragments of the sequence:

Univ.Primer U1—Zipcode Zi—Upstream Target-Mutation-Downstream Target—Univ.Primer U2'

For detection using universal arrays containing capture oligonucleotides, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array containing capture oligonucleotides.

In an alternative approach, highly sensitive mutation detection may be performed using split Zipcode sequences. This approach would use upstream first oligonucleotide probes (5' Universal Primer U1, a first half zipcode sequence Ai and a short sequence Ci, followed by target-specific sequence with a C:A or G:T mismatch at the penultimate base, and the mutation base at the 3' end), and downstream second oligonucleotide probes (5' of 20 base extra overhang, where 8-10 bases are complementary to 3' end of Univ.Primer U2' sequence, followed by target-specific sequence—the complement of the short sequence Ci', a second half zipcode sequence Ai—Univ.Primer U2'). After universal PCR amplification, these conditions amplify fragments of the sequence:

Univ.Primer U1—1$^{st}$ ½ Zipcode Zi—Short Ci—Upstream Target-Mutation-Downstream Target—Short Ci'—2$^{nd}$ ½ Zipcode Zi—Univ.Primer U2'

When the Short Ci transiently hybridizes to Short Ci', the 1$^{st}$ ½ Zipcode Zi sequence is brought in proximity to the 2$^{nd}$ ½ Zipcode Zi, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1—Unique Ai—1$^{st}$ ½ Zipcode Zi—Short Ci—Upstream Target-Mutation-Downstream Target—Short Ci'—2$^{nd}$ ½ Zipcode Zi—Unique Bi—Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full length zipcode sequence.

Since each junction sequence between the target sequences is unique, the products of the initial universal amplification may also be identified and quantified using next-generation sequencing. (Sequencing can identify target-independent ligation of incorrect fragments, but not for misligation of mutant ligation probe on normal target. However, use of non-amplifying upstream ligation probe for wild-type sequence should significantly minimize such incorrect ligations).

An alternative approach to this problem is to forego using probes to the wild-type sequence, but instead use ligation probe that are coupled to each other through their non-ligating ends. This allows use of lower primer concentrations. Further, it provides a simple way to remove both upstream and downstream unligated primers from undergoing post-ligation reactions.

Detailed Protocol for Highly Sensitive Detection of Mutation Marker (when Present at 1% to 0.01%), Repeat Mutations in Known Genes Using Coupled Probes (See FIG. 8):

Step 1: Denature genomic DNA from serum (94° C. 1 minute) in the presence of coupled oligonucleotide probes, comprising of upstream LDR primer portions (5' Univ.Primer U1—UniTaq Ai, followed by target-specific sequence with a C:A or G:T mismatch at the penultimate base, and the mutation base at the 3' end), coupled to the matched downstream LDR primer portions (5' same mutation base or flap containing same mutation base followed by target-specific sequence—UniTaq Bi'—Univ.Primer U2'—and 8-10 bases target specific sequence complementary to the free 3' end of the upstream primer sequence portion), Taq polymerase, and thermostable ligase (preferably from strain AK16D). In this variation, the coupled probe can contain additional bases or just spacer, but should contain a region that polymerase does not copy through. Perform one or more ligation reactions that have been optimized for perfect match polymerase cleavage/ligation compared to mismatch polymerase cleavage/ligation. This will allow for ligation events to occur if mutant DNA is present.

Step 2: Add hot start dNTP's Universal Primer U1, and Universal Primer U2. Incubate at 55° C. (activates dNTPs) to allow unligated coupled probes to self-hairpin to the 8-10 bases that are complementary to 3' end, which extends to create longer hairpins that render these coupled primers refractory to further amplification. Then, allow PCR amplification to proceed for 8-20 cycles. Ideally, the universal primer tails U1 and U2 on the bridge primers are slightly shorter than Universal primers U1 and U2. Further the universal primers U1 and U2 contain a short sequence in common (i.e. 6-10 bases) to avoid primer dimer formation. In an optional variation to minimize target independent amplifications, the bridge PCR primers contain a uracil base and a blocked 3' end, which is liberated by an RNase-H that cleaves the uracil base when the primer is hybridized to its target. These conditions generate universal amplification products of the sequence:

Univ.Primer U1-UniTaq Ai—Upstream Target-Mutation-Downstream Target—UniTaq Bi'—Univ.Primer U2'

Step 3: Open tube, dilute 10- to 100-fold and distribute aliquots to Taqman wells, each well containing the following primers: Universal Primer U2 and UniTaq specific primers of the format F1-UniTaq Bi—Q—UniTaq Ai (where F1 is a fluorescent dye that is quenched by Quencher Q). Under these conditions, the following secondary extension products will form:

F1-UniTaq Bi—Q-UniTaq Ai—Upstream Target-Mutation-Downstream Target—UniTaq Bi'—Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

In a variation of the above, the matched downstream LDR primer portions, i.e. 5' same mutation base or flap containing same mutation base followed by target-specific sequence—UniTaq B1'—do not include 8-10 bases of target specific sequence complementary to the free 3' end of the upstream primer sequence portion. Instead, the coupled probe contains an internal sequence that does not inhibit exonuclease digestion, but may be cleaved after an exonuclease digestion step, and prior to a polymerase amplification step. An example of such a sequence is use of a uracil base, which may be subsequently cleaved with uracil DNA glycosylase. In this example, after the ligation step, both Exonuclease I and Exonuclease III are added to digest all unligated coupled probes, as well as all input target DNA. After heat-killing the exonucleases, uracil DNA glycosylase is added to linearize the ligated probes for subsequent PCR amplification.

In both of the above variations, the coupled probes may be synthesized without one or both Univ.Primer U1 and/or Univ.Primer U2' sequences, or portions thereof, thus requiring the need for one or two bridge primers (Universal Primer U1-UniTaq Ai and Universal Primer U2-UniTaq Bi) during the universal PCR amplification step.

A summary of potential primer designs to detect mutations, insertions, and deletions is shown in FIG. 2. For single-base mutations, the "Z" base in the $2^{nd}$ or $3^{rd}$ (not shown) position from the 3' end represents: dG, dA, Inosine, Nitroindole, Nitropyrrole or other nucleotide analogue, and by destabilizing the 3' end will reduce inappropriate misligations when mutant probes are hybridized to wild-type target (FIG. 2A). For insertions or deletions, use of a matched base or nucleotide analogue in the $2^{nd}$ or $3^{rd}$ position that improves stability (such as 2-amino-dA or 5-propynyl-dC) may improve discrimination of such frame-shift mutations from wild-type sequences. For insertions, use of one or more thiophosphate groups downstream from the desired scissile phosphate bond of the downstream probe will prevent inappropriate cleavage by the 5'-3' exonuclease activity of polymerase when the probes are hybridized to wild-type DNA, and thus reduce false-positive ligation on wild-type target (FIG. 2B). Likewise, for deletions, use of one or more thiophosphate groups upstream from the desired scissile phosphate bond of the downstream probe will prevent inappropriate cleavage by the 5'-3' exonuclease activity of polymerase when the probes are hybridized to wild-type DNA, and thus reduce false-positive ligation on wild-type target (FIG. 2C). The tags from the upstream and downstream probes may also be coupled through their non-ligating ends, as shown in FIG. 8.

Fluorescent Labeling:

Consider an instrument that can detect 5 fluorescent signals, F1, F2, F3, F4, and F5 respectively. As an example, in the case of colon cancer, the highest frequency mutations will be found for K-ras, p53, APC and BRAF. Mutations in these four genes could be detected with a single fluorescent signal; F1, F2, F3, F4. If the scale is 1000 FU, then primer would be added using ratios of labeled and unlabeled UniTaq primers, such that amplification of LDR products on mutant target of these genes yields about 300 FU at the plateau. For the controls, the F5 would be calibrated to give a signal of 100 FU for the 1:1,000 dilution quantification control, and an additional 300 FU for ligation of mutant probe on wild-type control (should give no or low background signal).

For the other genes commonly mutated in colon cancer as shown below, (or even lower abundance mutations in the p53 gene,) the following coding system may be used: Two fluorescent signals in equimolar amount at the 5' end of the same UniTaq, with unlabeled primer titrated in, such that both fluorescent signals plateau at 100 FU. If fluorescent signals are F1, F2, F3, F4, then that gives the ability to detect mutations in 4 genes using a single fluorescent signal, and in mutations in 6 genes using combinations of fluorescent signal:

Gene 1=F1 (300 FU) (p53, Hot Spots)
Gene 2=F2 (300 FU) (KRAS)
Gene 3=F3 (300 FU) (APC)
Gene 4=F4 (300 FU) (BRAF)
Gene 5=F1 (100 FU), F2 (100 FU) (PIK3CA)
Gene 6=F1 (100 FU), F3 (100 FU) (FBXW7)
Gene 7=F1 (100 FU), F4 (100 FU) (SMAD4)
Gene 8=F2 (100 FU), F3 (100 FU) (p53, additional)
Gene 9=F2 (100 FU), F4 (100 FU) (CTNNB1)
Gene 10=F3 (100 FU), F4 (100 FU) (NRAS)

Suppose there is a second mutation, combined with a mutation in one of the top genes. This is easy to distinguish, since the top gene will always give more signal, independent if it is overlapping with the other fluorescent signals or not. For example, if the fluorescent signal is F1 100 FU, and F2 400 FU, that would correspond to mutations in Gene 2 and Gene 5.

If there are two mutations from the less commonly mutated genes (Gene 5-Gene 10) then the results will appear either as an overlap in fluorescent signals, i.e. F1 200 FU, F2 100 FU, F4 100 FU, or all 4 fluorescent signals. If the fluorescent signals are in the ratio of 2:1:1, then it's rather straightforward to figure out the 2 mutations: in the above example, F1 200 FU, F2 100 FU, F4 100 FU, would correspond to mutations in Gene 5 and Gene 7.

For all 4 fluorescent signals, it is highly unlikely that the concentration of the mutations is exactly identical, i.e. all 4 fluorescent signals will start appearing at the same time or yield the same Ct. If two fluorescent signals are linked to each other in terms of detecting the mutation, then their kinetics should be the same. For example, if F1 100 FU and F2 100 FU had a Ct of 31 and F3 100 FU and F4 100 FU had a Ct of 31.8, then that pattern would correspond to mutations in Gene 5 and Gene 10.

Finally, appearance of 3 or 4 fluorescent signals indicates that at least two genes contain mutations, suggesting it is highly likely that the cDNA reflects evidence of a tumor or cancer, independent of the nature of the mutations.

In an alternative approach, highly sensitive mutation detection may be performed using Zipcode array, Zipcode Taqman or traditional Taqman detection. This approach would use upstream first oligonucleotide ligation probes (5' Zipcode Zi, followed by target-specific sequence with a C:A or G:T mismatch at the penultimate base, and the mutation base at the 3' end), coupled to the matched downstream second oligonucleotide ligation probes (5' same mutation base followed by target-specific sequence—Univ.Primer U2'—and 8-10 bases target specific sequence complementary to the free 3' end of the upstream primer sequence). After universal PCR amplification, the following amplification products are formed:

Univ.Primer U1—Zipcode Zi—Upstream Target-Mutation-Downstream Target—Univ.Primer U2'

For detection using universal (zipcode) arrays comprising a collection of capture oligonucleotides, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

In an alternative approach, how highly sensitive mutation detection may be performed using split Zipcode sequences. This approach would use upstream first oligonucleotide probes (5' Universal Primer U1, a first half zipcode sequence Ai and a short sequence Ci, followed by target-specific sequence with a C:A or G:T mismatch at the penultimate base, and the mutation base at the 3' end), coupled to the matched downstream second oligonucleotide probes (5' same mutation base followed by target-specific sequence— the complement of the short sequence Ci', a second half zipcode sequence Ai—Univ.Primer U2'—and 8-10 bases target specific sequence complementary to the free 3' end of the upstream primer sequence). After universal PCR amplification, the amplification product would have the sequence:

Univ.Primer U1—$1^{st}$ ½ Zipcode Zi—Short Ci—Upstream Target-Mutation-Downstream Target—Short Ci'—$2^{nd}$½ Zipcode Zi—Univ.Primer U2'

When the Short Ci transiently hybridizes to Short Ci', the $1^{st}$ ½ Zipcode Zi sequence is brought in proximity to the $2^{nd}$ ½ Zipcode Zi, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1—Unique Ai—$1^{st}$ ½ Zipcode Zi—Short Ci—Upstream Target-Mutation-Downstream Target— Short Ci'—$2^{nd}$ ½ Zipcode Zi—Unique Bi—Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full length zipcode sequence.

Prophetic Example 2

High Sensitivity Mutation Marker (Present at 1% to 0.01%); Uncommon Mutations in Known Genes Mutational changes in tumor suppressor genes such as p53 and APC are too numerous to cover using allele-specific PCR approaches. Thus, the approach has shifted to deep sequencing across all exons of the protein. When input DNA is limiting, it is important to achieve equal amplification of different regions to assure the same general depth of coverage.

Overview of Approach:

The idea is to faithfully make a copy of all exons that are present and do a limited equal amplification of all prior to sequencing. While others use tricks like cold-PCR to enrich for wild-type fragments, such an approach is vulnerable to SNPs within the genes of interest. Further, such enrichment approaches are unlikely to amplify fragments equally, leaving the task of deep sequencing anyway.

To copy all exons, an upstream ligation probe is paired with a downstream ligation probe that is about 100 to 160 bp downstream, depending on the quality of the DNA being evaluated. If the DNA is from serum, where the average size of tumor derived DNA is about 160 bases, the smaller size amplicon is used, with an overlapping tiling strategy used for alternating tubes.

The challenge here is to avoid having polymerase extend the upstream primer in such a way that it destroys the downstream probe without a ligation step. This is accomplished by incorporating thiophosphate linkages in the $2^{rd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream probe), the target bases at the ligation junction would preferentially be AT rich on the 3' side, and GC rich on the 5' side.

An alternative approach is to use a downstream ligation probe containing an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the probe is bound to the target. The endonuclease also cleaves single-stranded probe, but with lower efficiency, and thus probe hybridized to template would be the preferred substrate. When using thermostable EndoIII, the PCR polymerase used would lack the 5'→3' exonuclease activity.

Detailed Protocol for Highly Sensitive Detection of Mutation Marker (Present at 1% to 0.01%); Uncommon Mutations in Known Genes (FIG. 14):

Step 1: Denature genomic DNA from serum (94° C., 5 minutes to activate Hot start Taq polymerase) in the presence of upstream first oligonucleotide probe (5' Universal Primer U1, followed by target-specific sequence at the 3' end), downstream second oligonucleotide probe (5' of 20 base extra overhang, where 8-10 bases are complementary to 3' end of Univ.Primer U2' sequence, followed by target-specific sequence—Univ.Primer U2'), Hot start Taq polymerase, dNTPs and thermostable ligase (preferably from strain AK16D). The downstream probe is longer and has a higher Tm value than the upstream probe, such that when cooling from 94° C. one pauses at 70° C. to allow the downstream probe to anneal first, then when the reaction is cooled to 65° C. or 60° C., allowing the upstream probe to hybridize and polymerase to make a copy of the DNA between the two probes, clip the 5' tail from the downstream probe, and then thermostable ligase seals the nick. The downstream probe has thiophosphate linkages in the $2^{nd}$ and $3^{rd}$ position from the 5' phosphate end, (which will be liberated by the 5'→3' nuclease activity of the polymerase) such that the polymerase does not digest the downstream probe but rather falls off to allow a ligation step.

Step 2: Add Universal Primer U1, Universal Primer U2. Incubate at 55° C. to allow unligated downstream probe to self-hairpin to the 8-10 bases that are complementary to 3' end, which extends to create longer hairpins that render these downstream probes refractory to further amplification. Then, allow PCR amplification to proceed for 8-20 cycles. Ideally, the universal primer tails U1 and U2 on the ligation composite probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite ligation probes binding to incorrect products). Further the universal primers U1 and U2 contain a short sequence in common (i.e. 6-10 bases) to avoid primer dimer formation. Then, allow amplification to proceed for 8-20 cycles. These universal PCR conditions amplify fragments of the sequence:

Univ.Primer U1—about 100-160 bases Target—(Possibly Containing Mutation)—Univ.Primer U2'

Step 3: The presence of mutation in the gene can then be identified using next generation sequencing technology.

When dealing with low numbers of input DNA molecules containing a mutation in the presence of an excess of wild-type DNA, there is the potential for polymerase error. Consequently it will be necessary to confirm presence of the mutation on both strands in multiple reads.

An alternative Step 1 would use thermostable polymerase lacking the 5'→3' exonuclease activity (preferably containing the 3'→5' proofreading activity) in the presence of upstream ligation probes (5' Universal Primer U1, followed by target-specific sequence at the 3' end, with thiophosphate linkages in the $1^{st}$ and $2^{nd}$ positions from the 3' end to avoid digesting probe when using polymerase with 3'→5' proofreading activity), downstream ligation probe (5' of 20 base extra overhang, where 8-10 bases are complementary to 3' end of Univ.Primer U2' sequence, an apurinic sites, followed by target-specific sequence—Univ.Primer U2'), dNTPs, thermostable EndoIII (preferably Tma EndoIII), and thermostable ligase (preferably from strain AK16D). The downstream probe is longer and has a higher Tm value than the upstream probe, such that when cooling from 94° C. one pauses at 70° C. to allow the downstream probe to anneal first and be clipped with the EndoIII to liberate the 5' end, then when the reaction is cooled to 65° C. or 60° C., allowing the upstream probe to hybridize and polymerase to make a copy of the DNA between the two primers, and then thermostable ligase seals the nick.

Prophetic Example 3

Accurate Quantification of Tumor-Specific mRNA Isolated from Exosomes

In the past few years, several groups have captured tumor-specific exosomes, which contain miRNA and mRNA that is specific to the original tumor cell. Accurate quantification of these markers may help identify early cancer, as well as provide signatures for predicting outcome. Traditionally, relative levels of mRNA expression are determined using reverse-transcription—real-time PCR.

Overview to approach: Here the idea is to count how many copies of mRNA from a dozen or so genes are present in the sample. An initial reverse transcription step makes DNA copies of all desired regions of mRNA, and then one or two ligation probe pairs per transcript can be used to accurately quantify the amount of each transcript of interest.

The challenge here again is to avoid having polymerase extend the upstream probe in such a way that it destroys the downstream probe without a ligation step. This is accomplished by incorporating thiophosphate linkages in the $2^{nd}$ and $3^{rd}$ position from the 5' phosphate end, (which will be liberated by the 5'→3' nuclease activity of the polymerase,). To minimize polymerase displacement of those bases as it extends one base too many (which would make it impossible to ligate to the downstream primer), the target bases at the ligation junction would preferentially be AT rich on the 3' side, and GC rich on the 5' side.

Unlike the case for identifying rare mutations, there is no need to determine any sequence information between the two ligation probes. Thus, they may be designed to be directly adjacent to each other. In this alternative approach, downstream second oligonucleotide probe contain an apurinic (AP) site at the position adjacent to the desired 5' phosphate. This 5' phosphate is liberated using a thermostable EndoIII (such as Tma EndoIII). This enzyme cleaves AP sites leaving a 5' phosphate when the probe is bound to the target. The endonuclease also cleaves single-stranded probe, but with lower efficiency, and thus probe hybridized to template would be the preferred substrate. When using thermostable EndoIII to liberate the 5' phosphate, there is no need to add thermostable polymerase at this step, since ligase can immediately seal the nick at the junction.

While this protocol is written for coding mRNA, it is also equally valid for quantifying non-coding RNA. Such non-coding RNA may also be present in tumor-derived exosomes.

Detailed Protocol for Quantification of Tumor-Specific mRNA Isolated from Exosomes:

Step 1: Use reverse transcriptase (RT) with either gene-specific primers or non-specific dN-dT10 priming to generate cDNA copies of 3' ends of transcripts. Incubate at 37° C. for 1 hour, then heat kill RT at 94° C. for 5 minute and simultaneously activate Hot start Taq polymerase. Reaction also contains upstream first oligonucleotide probes (5' Universal Primer U1, followed by UniTaq Ai, followed by target gene-specific sequence at the 3' end), downstream second oligonucleotide probes (5' of 20 base extra overhang, where 8-10 bases are complementary to 3' end of Univ.Primer U2' sequence, followed by target gene-specific sequence—UniTaq Bi'—Univ.Primer U2'), Hot start Taq polymerase, and thermostable ligase (preferably from strain AK16D). The downstream probe has thiophosphate linkages in the $2^{nd}$ and $3^{rd}$ position from the 5' phosphate end, (which will be liberated by the 5'→3' nuclease activity of the polymerase,) such that the polymerase does not digest the downstream probe, but rather falls off to allow a ligation step.

Step 2: Add Universal Primer U1, Universal Primer U2. Incubate at 55° C. to allow unligated downstream probes to self-hairpin to the 8-10 bases that are complementary to 3' end, which extends to create longer hairpins that render these downstream probe refractory to further amplification. Ideally, the universal primer tails U1 and U2 on the composite ligation probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR primers binding to incorrect products). Further the universal primers U1 and U2 contain a short sequence in common (i.e. 6-10 bases) to avoid primer dimer formation. Then, allow amplification to proceed for 8-20 cycles. These universal amplification conditions amplify products of the sequence:

Univ.Primer U1-UniTaq Ai—Gene Target Region-UniTaq Bi'—Univ.Primer U2'

Step 3: Open tube, dilute 10- to 100-fold and distribute aliquots to Taqman wells, each well containing the following primers: Universal Primer U2 and UniTaq specific primers of the format F1-UniTaq Bi—Q—UniTaq Ai (where F1 is a fluorescent dye that is quenched by Quencher Q). Under these conditions, the following product will form:

F1-UniTaq Bi—Q-UniTaq Ai—Gene Target Region-UniTaq Bi'—Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

In an alternative approach, accurate quantification of tumor-specific mRNA may be performed using Zipcode array, Zipcode Taqman or traditional Taqman detection. This approach would use upstream first oligonucleotide probes (5' Universal Primer U1, followed by Zipcode Zi, followed by target gene-specific sequence at the 3' end), and downstream second oligonucleotide probes (5' of 20 base extra overhang, where 8-10 bases are complementary to 3' end of Univ.Primer U2' sequence, followed by target gene-specific sequence—Univ.Primer U2'). After universal PCR amplification, products of the following sequence are formed:

Univ.Primer U1—Zipcode Zi—Gene Target Region—Univ.Primer U2'

For detection using universal (zipcode) arrays containing a collection of capture oligonucleotides, the Univ.Primer U2 would contain a reporter label, i.e. a fluorescent group, while the Univ.Primer U1 would contain a 5' phosphate, and amplification would continue for a total of about 30 to 40 cycles. This would allow for use of lambda exonuclease to digest the second strand, rendering the fluorescently labeled product single-stranded and suitable for hybridization on a universal (zipcode) array.

In addition, the above constructs can include unique sequence (ranging from 0 to 10 bases) internal to the Universal primers (Unique Ai, Unique Bi), to amplify fragments of the sequence:

Univ.Primer U1—Unique Ai—Zipcode Zi—Gene Target Region—Unique Bi—Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the zipcode sequence.

In an alternative approach, accurate quantification of tumor-specific mRNA may be performed using split Zipcode sequences. This approach would use upstream first oligonucleotide probe (5' Universal Primer U1, a first half zipcode sequence Ai and a short sequence Ci, followed by target gene-specific sequence at the 3' end), and downstream second oligonucleotide probe (5' of 20 base extra overhang, where 8-10 bases are complementary to 3' end of Univ.Primer U2' sequence, followed by target gene-specific sequence—the complement of the short sequence Ci', a second half zipcode sequence Ai—Univ.Primer U2'). After universal PCR amplification, these conditions amplify fragments of the sequence:

Univ.Primer U1—$1^{st}$ ½ Zipcode Zi—Short Ci—Gene Target Region—Short Ci'—$2^{nd}$ ½ Zipcode Zi—Univ.Primer U2'

When the Short Ci transiently hybridizes to Short Ci', the $1^{st}$ ½ Zipcode Zi sequence is brought in proximity to the $2^{nd}$ ½ Zipcode Zi, and the transient hybridization may be stabilized when hybridizing both Zipcode Zi half sequences to the full-length Zipcode Zi' sequence on a zipcode array.

In addition, the above constructs can include unique sequence (ranging from 0 to 10 bases) internal to the Universal primers (Unique Ai, Unique Bi), represented as follows.

Univ.Primer U1—Unique Ai—$1^{st}$ ½ Zipcode Zi—Short Ci—Gene Target Region—Short Ci'—$2^{nd}$ ½ Zipcode Zi—Unique Bi—Univ.Primer U2'

For detection using Zipcode Taqman assays, after the 8-20 cycles of universal amplification, the sample would be diluted 10- to 100-fold and unique primers would be added that overlap with the Unique Ai the Unique Bi sequence for each product. The Taqman probe would be to the full-length zipcode sequence.

Since each junction sequence between the target sequences is unique, the products of the initial universal amplification may also be identified and quantified using next-generation sequencing. Under these conditions, the LDR probes may be hybridized directly adjacent to each other, or alternatively allow polymerase to fill in sequence between the two primers prior to clipping the 5' end of the downstream primer to liberate the 5' phosphate.

One would like to include "low-level" housekeeping genes as controls. Alternatively, one can compare Ct values of genes predicted to increase in expression/copy number to those genes predicted to decrease in expression/copy number.

An alternative to Step 1 above would use thermostable EndoIII (preferably Tma EndoIII), in the presence of upstream first oligonucleotide probe (5' Universal Primer U1, followed by target-specific sequence at the 3' end), downstream second oligonucleotide probe (5' of 20 base extra overhang, where 8-10 bases are complementary to 3' end of Univ.Primer U2' sequence, an apurinic sites, followed by target-specific sequence—Univ.Primer U2'), dNTPs, and thermostable ligase (preferably from strain AK16D). The downstream probe is longer and has a higher Tm value than the upstream probe, such that when cooling from 94° C. one pauses at 70° C. to allow the downstream probe to anneal first and be clipped with the EndoIII to liberate the 5' end, then when the reaction is cooled to 65° C. or 60° C., allowing the upstream probe to hybridize directly adjacent to the 5' phosphate liberated downstream probe, and then thermostable ligase seals the nick.

Prophetic Example 4

Accurate Quantification of Tumor-Specific miRNA Isolated from Exosomes or Argonaut Proteins Overview of approach: Approach is the same as for mRNA, except the initial miRNA specific primers have a small hairpin which forms at low temperature, and allows for hybridization and extension on the miRNA target. At the higher temperatures suitable for LDR ligations, the hairpin is single-stranded and provides additional bases for allowing the downstream LDR primer to hybridize. The approach of using miRNA specific primers with a small hairpin was developed at ABI.

Prophetic Example 5

Accurate Quantification of Tumor-Specific Copy Changes in DNA Isolated from Circulating Tumor Cells Copy changes in tumor DNA can be a strong predictor of outcome. Over the last several years, most copy number work has been performed on SNP chips, where bioinformatic approaches average the signal across a region to determine relative copy number. For low numbers of cells, digital PCR approaches are used to obtain an accurate count of starting molecules.

Overview of Approach:

Generally, copy changes occur over large regions of DNA, such as chromosomal arms. Since we are dealing with very low numbers of tumor cells, one could improve accuracy by interrogating multiple regions of a given chromosomal arm simultaneously, and adding or averaging the resultant signal. Likewise, specific genes are amplified in some tumors (i.e. Her2-neu, IGF2), which may predict outcome or guide therapy.

Detailed Protocol for Quantification of Tumor-Specific Copy Changes in DNA Isolated from Circulating Tumor Cells:

Step 1: Denature genomic DNA from serum (94° C., 5 minutes to activate Hot start Taq polymerase) in the presence of upstream first oligonucleotide probe (5' Universal Primer U1, followed by UniTaq Ai, followed by target-specific sequence at the 3' end), downstream second oligonucleotide probe (5' of 20 base extra overhang, where 8-10 bases are complementary to 3' end of Univ.Primer U2' sequence, followed by target gene-specific sequence—UniTaq Bi'—Univ.Primer U2'), Hot start Taq polymerase, and thermostable ligase (preferably from strain AK16D).

Step 2: Add Hot Start dNTPs, Universal Primer U1, Universal Primer U2. Incubate at 55° C. to allow unligated downstream probes to self-hairpin to the 8-10 bases that are complementary to 3' end, which extends to create longer hairpins that render these downstream probes refractory to further amplification. Ideally, the universal primer tails U1 and U2 on the composite ligation probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite ligation probes binding to incorrect products). Further the universal primers U1 and U2 contain a short sequence in common (i.e. 6-10 bases) to avoid primer dimer formation. Then, allow amplification to proceed for 8-20 cycles. These conditions amplify fragments of the sequence:
Univ.Primer U1-UniTaq Ai—Target Region-UniTaq Bi'—Univ.Primer U2'

Step 3: Open tube, dilute 10- to 100-fold and distribute aliquots to wells for digital PCR, each well containing the following primers: Universal Primer U2 and UniTaq specific primers of the format F1-UniTaq Bi—Q—UniTaq Ai (where F1 is a fluorescent dye that is quenched by Quencher Q). Each well contains a set of ligation products for a given chromosomal arm or gene region, as well as for a control region. Under these conditions, the following product will form, after the digital PCR:
F1-UniTaq Bi—Q-UniTaq Ai—Target Region-UniTaq Bi'—Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye. The total droplets with fluorescent signal for the target region are compared with the total droplets with fluorescent signal for the control region to determine relative copy number.

Chromosomes that rarely undergo copy change in colon cancer: 2, 11, 16
Chromosomal arms that often undergo copy gain in colon cancer: 7p, 7q, 8q, 13q, 20p, 20q
Chromosomal arms that often undergo copy loss in colon cancer: 1p, 4p, 4q, 8p, 14q, 17p, 18p, 18q
Loss of 8p and 18q correlates with poor prognosis.
Her2-Neu amplification suggests treatment with Herceptin.
IGF2 amplification suggests treatment with an inhibitor of IGFR As an alternative to using digital PCR, the ligation products could be quantified by using next generation sequencing. To assure the ligation step took place on genomic DNA, the ligation probes hybridize about 10-20 bases apart, and the gap filled with polymerase prior to the ligation step, similar to the procedure described in Prophetic Example 2. This approach may be used when interrogating many regions simultaneously and looking for focused gene-specific deletions or amplifications.

Prophetic Example 6

Detection of Mutations in DNA Isolated from Circulating Tumor Cells

Circulating tumor cells provide the advantage of concentrating the mutation-containing DNA, so there is no longer a need to find low-level mutations in an excess of wild-type sequence. However, since there are a low number of starting DNA molecules, it is important to amplify all regions accurately, and verify mutations are truly present.

Overview of Approach:

The approach here is the same as that for finding known common point mutations, or for sequencing multiple exons, as outlined in Prophetic Examples 2 and 3 above. However, when dealing with low amounts of input DNA, there is the potential for polymerase error. Consequently it will be necessary to confirm presence of the mutation on both strands in multiple reads.

Since the DNA is being obtained from a few captured tumor cells, if a mutation is present, it should be present in some if not most of the captured cells. This opens the prospect for doing a PCR-LDR-PCR (UniTaq) assay.

Detailed Protocol for Detection of Mutations in DNA Isolated from Circulating Tumor Cells.

Step 1: Denature genomic DNA from captured CTCs (94° C. 5 minutes) to activate hot-start Taq polymerase in the presence of gene-specific primers containing Uracil, and PCR amplify DNA for 10-20 cycles. Heat kill Taq polymerase by incubating at 99° C. for 30 minutes. The purpose of heat killing polymerase after limited PCR cycles is to avoid spurious extension products among ligation probes during the 30-minute incubation with the mix containing UNG and AP endonuclease.

Step 2: Add UNG and AP endonuclease, Hot-start Taq polymerase, fresh dNTPs if needed, Universal Primer U1, Universal Primer U2. Incubate at 37° C. for 30 minute to destroy original primers, activate polymerase at 95° C. for 5 minutes. Reaction contains upstream first oligonucleotide probes (5' Universal Primer U1, followed by UniTaq Ai, followed by target-specific sequence with a C:A or G:T mismatch at the penultimate base, and the mutation base at the 3' end), downstream second oligonucleotide probes (5' of 20 base extra overhang, where 8-10 bases are complementary to 3' end of Univ.Primer U2' sequence, followed by target-specific sequence—UniTaq Bi'—Univ.Primer U2'), Taq polymerase, and thermostable ligase (preferably from strain AK16D). Perform one or more ligation reactions, where the annealing temperature cycles one or more times between 60° C. for ligation (10 minutes) and 75° C. (1 minute). This will allow for ligation events to occur if mutant DNA is present. The downstream probe has thiophosphate linkages in the $2^{nd}$ and $3^{rd}$ position from the 5' phosphate end, (which will be liberated by the 5'→3' nuclease activity of the polymerase,) such that the polymerase does not digest the downstream probe, but rather falls off to allow a ligation step. A further option is to design the downstream probe so it is longer and has a higher Tm value than the upstream probe, such that when cooling from 94° C. one pauses at 70° C. to allow the downstream probe to anneal first, then when the reaction is cooled to 65° C. or 60° C., allowing the upstream probe to hybridize and polymerase to clip the 5' tail from the downstream probe, and then thermostable ligase seals the nick. This should limit polymerase extension of upstream probe before downstream probe hybridizes.

Step 3: Add Universal Primer U1, Universal Primer U2. Incubate at 55° C. to allow unligated downstream probes to self-hairpin to the 8-10 bases that are complementary to 3' end, which extends to create longer hairpins that render these downstream probes refractory to further amplification. Then, allow PCR amplification to proceed for 0-15 cycles. Ideally, the universal primer tails U1 and U2 on the composite ligation probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite LDR primers binding to incorrect products). Further the universal primers U1 and U2 contain a short sequence in common (i.e. 6-10 bases) to avoid primer dimer formation. These conditions amplify fragments of the sequence:

Univ.Primer U1-UniTaq Ai—Upstream Target-Mutation-Downstream Target—UniTaq Bi'—Univ.Primer U2'

Step 4: Open tube, dilute 10- to 100-fold and distribute aliquots to Taqman wells, each well containing the following primers: Universal Primer U2 and UniTaq speicific primers of the format F1-UniTaq Bi—Q-UniTaq Ai (where F1 is a fluorescent dye that is quenched by Quencher Q). Under these conditions, the following product will form:

F1-UniTaq Bi—Q-UniTaq Ai—Upstream Target-Mutation-Downstream Target—UniTaq Bi'—Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye.

In an alternative approach, how highly sensitive mutation detection may be performed using Zipcode array, Zipcode Taqman or traditional Taqman detection as described in prophetic Example 3 resulting in the following products:

Univ.Primer U1—Zipcode Zi—Upstream Target-Mutation-Downstream Target—Univ.Primer U2'

In an alternative approach, highly sensitive mutation detection may be performed using split Zipcode sequences as described in prophetic Example 3 above, resulting in the following products:

Univ.Primer U1—1$^{st}$ ½ Zipcode Zi—Short Ci—Upstream Target-Mutation-Downstream Target—Short Ci'—2$^{nd}$ ½ Zipcode Zi—Univ.Primer U2'

Since there is the primary amplification of PCR products, it is possible to skip Step 3. Further, the upstream LDR probes do not need a universal sequence, such that ligation products from Step 2 would be of the following form:

UniTaq Ai—Upstream Target-Mutation-Downstream Target—UniTaq Bi'—Univ.Primer U2'

This will still allow ligation products of Step 4 to be of the following form:

F1-UniTaq Bi—Q-UniTaq Ai—Upstream Target-Mutation-Downstream Target—UniTaq Bi'—Univ.Primer U2'

Also, if the universal primer PCR amplification of Step 4 is skipped, an alternative to getting rid of unused PCR primers using UNG and AP endonuclease in Step 2 is to use a heat sensitive phosphatase (i.e. CIAP) to destroy dNTP's after Step 1 and before Step 2. No fresh dNTPs would be added in Step 2 because they would not be needed for Step 3.

Prophetic Example 7

Accurate Quantification of Tumor-Specific mRNA Isolated from Exosomes or Circulating Tumor Cells See approach as outlined in Prophetic Example 3 above. When isolating mRNA from circulating tumor cells, the total amount may be quite low. Therefore, it may be prudent to use more than one ligation probe set for a given mRNA transcript, and have the readout in digital PCR. Proceed with Steps 1 and 2 as outlined for Steps 1 and 2 of Prophetic Example 3 above, then:

Step 3: Open tube, dilute 10- to 100-fold and distribute aliquots to wells for digital PCR, each well containing the following primers: Universal Primer U2 and UniTaq specific primers of the format F1-UniTaq Bi—Q-UniTaq Ai. (where F1 is a fluorescent dye that is quenched by Quencher Q). Each well contains a set of ligation products for a given mRNA region, as well as for a control region. Under these conditions, the following product will form, after the digital PCR:

F1-UniTaq Bi—Q-UniTaq Ai—Target Region—UniTaq Bi'—Univ.Primer U2'

This will hairpin, such that the UniTaq B1 sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye. The total droplets with fluorescent signal for the target region are compared with the total droplets with fluorescent signal for the control region to determine relative mRNA expression levels.

Prophetic Example 8

Prenatal Diagnostic Applications from Maternal Serum Samples

Overview: Recent work has shown that fetal DNA as a percentage of maternal DNA in the serum is at approximately 6%, 20%, and 26% in the 1$^{st}$, 2$^{nd}$, and 3$^{rd}$ trimester respectively. Due to how DNA is degraded, maternal DNA is usually about 160 bases and still associated with the H1 histone, while fetal DNA is about 140 bases and not associated with histone. Depending on the clinical need, and where the knowledge will provide the best care, tests may be developed with sufficient sensitivity to detect fetal DNA in the appropriate trimester.

Aneuploidy Through Counting Copy Number (e.g., Trisomy 21).

See approach Prophetic Example 5 described above. It is wisest to use a large number of regions to interrogate chromosome 21 and a control chromosome (e.g. chromosome 2), to show that the chromosomal count for fetal 21 is statistically higher than for fetal control (e.g., chromosome 2). By using an internal control chromosome in each digital amplification well, the method does not depend on the exact amplification conditions or efficiency per cycle.

An alternative approach depends on interrogating individual SNPs, and is better suited for disease mutations, as described below.

Inherited Diseases Containing Common Mutations in Known Genes (e.g. Sickle Cell Anemia, Cystic Fibrosis).

Sequence analysis readily determines presence of the recessive allele in both parents. If the mutation is different in the parents, it is possible to determine if the child is a compound heterozygote for the disease by evaluating cell-free DNA from the maternal serum. To obtain the full answer from analysis of fetal DNA in the maternal serum may require two parts to this assay. The first is to establish phase for the maternal SNPs that surround the disease gene. This may be accomplished by isolating high molecular weight DNA from WBC or metaphase chromosomes, and distributing into 96 or 384 well plates such that there is less than one chromosome per well. Subsequently, whole genome amplification is used to determine which wells contain the chromosome, and then the phase of 96 neighboring SNPs to the maternal disease allele are determined for the gene in question. Once this is accomplished, one scores for presence of the disease allele from the father (as described in Prophetic Example 2 above), and using digital PCR verifies that the chromosome that is inherited from the mother also contains a disease allele.

The key issue will be how important is it for the family to get the right answer. It is straightforward to determine if both parents are carriers, and if the mutations are different, relatively straightforward to determine if the father's disease allele is present in the fetus. If it is absent, then the fetus will be either disease free or a carrier. If it is present, then the chances of inheriting the maternal allele and getting the disease are 50%. If the error rate for the overall fetal DNA test is at 3%, is it worth it to get the wrong answer? It may be more prudent to do an amniocentesis and directly test for the presence of the maternal allele.

Consequently, the recommendation is to just sequence the gene as described in Prophetic Example 2 above, and score for the paternal disease allele. If present, or if the paternal and maternal disease-specific mutations are identical, recommend amniocentesis.

Inherited Diseases Containing Uncommon Mutations in Known Genes. (e.g. Familial Adenomatous Polyposis).

The approach described in Prophetic Example 2 can be utilized to detect these inherited disease mutations.

Inherited Diseases Arising from Known or Sporadic Copy Number Loss or Gain in Known Gene (e.g. Duchenne's Muscular Dystrophy).

See approach in Prophetic Example 5 above. If the mother is a carrier, and the region of copy loss is known, this will be easier to perform. If the mother is not a carrier, it is probably best to use sequencing to count copy number at multiple closely-spaced sequences throughout the DMD gene.

Prophetic Example 9

Paternity Testing

Overview: The basic approach is to look for presence of alleles present in the father, but absent in the mother. There are two general ways to approach this. One can start with SNPs where the common allele has a frequency around 70-75%, so that there is about a 50% chance the mother is homozygous for the major allele. One starts with about 48 SNPs of which about half of them (24) the mother will be homozygous for the common allele, and there is a 50% chance the father will be either heterozygous or homozygous for the minority allele. One simply scores for the presence of the minority allele in the maternal blood, similar to looking for mutations, but one also quantifies the amount present just to confirm it's a minority allele from the father. A second approach is to start with alleles with frequency around 50%, then there is a 50% chance the mother is homozygous for one of the alleles, and then there is a 75% chance the father will have the other allele at that position. It is a little less informative in differentiating the fathers, but more positions will be informative.

Detailed Protocol for Detection of SNP Allele Markers:

Step 1: Denature genomic DNA from serum (94° C. 1 minute) in the presence of 2 upstream first oligonucleotide probes (5' Universal Primer U1, followed by UniTaq A1i, followed by target-specific sequence and the SNP1 base at the 3' end, or Universal Primer U1, followed by UniTaq A2i, followed by target-specific sequence and the SNP2 base at the 3' end), downstream second oligonucleotide probes (5' of 20 base extra overhang, where 8-10 bases are complementary to 3' end of Univ.Primer U2' sequence, followed by target-specific sequence—UniTaq Bi'—Univ.Primer U2'), Taq polymerase, and thermostable ligase (preferably from strain AK16D). Perform one or more LDR reactions, where the annealing temperature cycles one or more times between 60° C. for ligation (10 minutes) and 75° C. (1 minute). This will allow for ligation events to occur for each SNP that is present.

Step 2: Add hot start dNTP's Universal Primer U1, Universal Primer U2. Incubate at 55° C. (activates dNTPs) to allow unligated downstream probes to self-hairpin to the 8-10 bases that are complementary to 3' end, which extends to create longer hairpins that render these downstream probes refractory to further amplification. Then, allow PCR amplification to proceed for 8-20 cycles. Ideally, the universal primer tails U1 and U2 on the composite ligation probes are slightly shorter than Universal primers U1 and U2. This allows initial universal amplification at a lower cycling temperature (i.e. 55° C. annealing) followed by higher cycling temperature (i.e. 65° C. annealing) such that the universal primers U1 and U2 bind preferentially to the desired product (compared to composite ligation probes binding to incorrect products). Further the universal primers U1 and U2 contain a short sequence in common (i.e. 6-10 bases) to avoid primer dimer formation. These conditions amplify fragments of the sequence:

Univ.Primer U1-UniTaq A1i—Upstream Target-SNP1-Downstream Target—UniTaq Bi'—Univ.Primer U2'

Univ.Primer U1-UniTaq A2i—Upstream Target-SNP2-Downstream Target—UniTaq Bi'—Univ.Primer U2'

Step 3: Open tube, dilute 10- to 100-fold and distribute aliquots to Taqman wells, each well containing the following primers: Universal Primer U2 and UniTaq speicific primers of the format F1-UniTaq Bi—Q-UniTaq A1i, and F2-UniTaq Bi—Q-UniTaq A2i. (where F1 and F2 are fluorescent dyes that are quenched by Quencher Q). Under these conditions, the following product will form:

F1-UniTaq Bi—Q-UniTaq A1i—Upstream Target-SNP1-Downstream Target—UniTaq Bi' Univ.Primer U2'

F2-UniTaq Bi—Q-UniTaq A2i—Upstream Target-SNP2-Downstream Target—UniTaq Bi'—Univ.Primer U2'

This will hairpin, such that the UniTaq Bi sequence pairs with the UniTaq Bi' sequence. When Universal Primer U2 binds to the Univ.Primer U2' sequence, the 5'→3' exonuclease activity of polymerase digests the UniTaq Bi sequence, liberating the F1 fluorescent dye if SNP1 was originally present, and F2 fluorescent dye if SNP2 was originally present.

In an alternative approach, SNP detection may be performed using Zipcode array, Zipcode Taqman or traditional Taqman detection (see Prophetic Example 1) to form the following products.

Univ.Primer U1—Zipcode A1i—Upstream Target-SNP1-Downstream Target—Univ.Primer U2'

Univ.Primer U1—Zipcode A2i—Upstream Target-SNP2-Downstream Target—Univ.Primer U2'

In an alternative approach, SNP detection may be performed using split Zipcode sequences (see Prophetic Example 1) to form the following products:

Univ.Primer U1—$1^{st}$ ½ Zipcode Zi—Short Ci—Upstream Target-SNP1-Downstream Target—Short Ci'—$2^{nd}$ ½ Zipcode Zi—Univ.Primer U2'

Univ.Primer U1—$1^{st}$ ½ Zipcode Zi—Short Ci—Upstream Target-SNP2-Downstream Target—Short Ci'—$2^{nd}$ ½ Zipcode Zi—Univ.Primer U2'

Although the invention has been described in detail for the purpose of illustration, it is understood that such details are solely for that purpose and variations can be made therein by those skilled in the art without departing from the spirit and scope of the invention which is defined by the following claims.

What is claimed is:

1. A method for identifying a presence of one or more target nucleotide sequences in a sample comprising:
   providing a sample potentially containing the one or more target nucleotide sequences;
   providing one or more oligonucleotide probe sets, each set comprising (a) a first oligonucleotide probe having a 5' primer-specific portion and a target-specific portion, and (b) a second oligonucleotide probe having a 3' primer-specific portion, a target specific portion, and a 5' nucleotide sequence, wherein said 5' nucleotide sequence is complementary to at least a portion of the 3' primer-specific portion and hybridizes to said complementary portion of the 3' primer-specific portion to form a hairpinned second oligonucleotide probe when said second probe is not hybridized to a target nucleotide sequence, wherein the first and second oligonucleotide probes of a probe set are configured to hybridize adjacent to one another on the target nucleotide sequence with a junction between the first and second oligonucleotide probes, and wherein, in a probe set, the target specific portion of the second oligonucleotide probe has an overlapping identical nucleotide at the junction with the first oligonucleotide probe;
   contacting the sample and the one or more oligonucleotide probe sets under conditions effective for first and second oligonucleotide probes of a probe set to hybridize at adjacent positions in a base specific manner to their corresponding target nucleotide sequences, if present in the sample, wherein upon hybridization the overlapping identical nucleotide of the second oligonucleotide probe forms a flap at the junction comprising the overlapping identical nucleotide;
   cleaving the overlapping identical nucleotide of the second oligonucleotide probe with an enzyme having 5' nuclease activity, thereby liberating a phosphate at the second oligonucleotide probe's 5' end;
   ligating first and second oligonucleotide probes of the one or more oligonucleotide probe sets together at the junction to form ligated product sequences, wherein each ligated product sequence comprises the 5' primer-specific portion, the target-specific portions, and the 3' primer-specific portions of the first and second oligonucleotide probes of an oligonucleotide probe set;
   detecting the ligated product sequences in the sample; and
   identifying the presence of one or more target nucleotide sequences in the sample based on said detecting.

2. The method of claim 1 further comprising:
   amplifying the target nucleotide sequences in the sample prior to said contacting.

3. The method of claim 1, wherein said detecting comprises:
   sequencing the ligated product sequences in the sample.

4. The method of claim 1, wherein said detecting comprises:
   separating the ligated product sequences by size.

5. The method of claim 1, wherein one of the oligonucleotide probes in a probe set further comprises a zip-code portion, wherein the zip-code portions hybridize to their complementary capture oligonucleotides under uniform hybridization conditions, said method further comprising:
   providing a collection of the capture oligonucleotides and
   contacting the ligation product sequence with the collection of capture oligonucleotides under conditions effective to hybridize the zip-code portion of each ligated product sequence to its complementary capture oligonucleotide in the collection with minimal non-specific hybridization and under uniform hybridization conditions, whereby said detecting takes place after hybridization of the ligated product sequences to their complementary capture oligonucleotides.

6. The method of claim 1 further comprising:
   providing one or more oligonucleotide primer sets, each set comprising (a) a first oligonucleotide primer comprising the same nucleotide sequence as the 5' primer-specific portion of the ligated product sequence and (b) a second oligonucleotide primer comprising a nucleotide sequence that is complementary to the 3' primer-specific portion of the ligated product sequence;
   blending the ligated product sequences, the one or more oligonucleotide primer sets, and a DNA polymerase to form a polymerase chain reaction mixture; and
   subjecting the polymerase chain reaction mixture to one or more polymerase chain reaction cycles comprising a denaturation treatment, a hybridization treatment, and an extension treatment thereby forming primary extension products, whereby said detecting involves detection of the primary extension products.

7. The method of claim 1, wherein the first and second oligonucleotide probes of the one or more oligonucleotide probe sets further comprise a first and second tag portion, respectively, wherein the first and second tag portions of an oligonucleotide probe set are complementary to each other, and wherein the first and second tag portions for each different oligonucleotide probe set have different nucleotide sequences, said method further comprising:
   subjecting the sample, after said ligating, to conditions effective for the first and second tag portions of a particular ligated product sequence to hybridize, thereby forming hairpinned ligated product sequences; and
   removing unligated oligonucleotide probes from the sample after said subjecting.

8. The method of claim 1, wherein the one or more oligonucleotide probe sets further comprise a third oligonucleotide probe having a target-specific target portion, wherein the second and third oligonucleotide probes of a probe set are configured to hybridize adjacent to one another on the target nucleotide sequence with a junction between the second and third oligonucleotide probes during said contacting, and wherein, in a probe set, the target specific portion of the third oligonucleotide probe has an overlapping identical nucleotide at the junction with the second oligonucleotide probe in a probe set that is removed during said cleaving to allow ligation between the second and third oligonucleotide probes at the junction to form a ligated product sequence comprising the first, second, and third oligonucleotide probes of a probe set.

9. The method of claim 1, wherein the sample is selected from the group consisting of tissue, cells, serum, blood, plasma, amniotic fluid, sputum, urine, bodily fluids, bodily secretions, bodily excretions, cell-free circulating nucleic acids, cell-free circulating fetal nucleic acids in pregnant woman, circulating tumor cells, tumor, tumor biopsy, and exosomes.

10. The method of claim 1, wherein the one or more target nucleotide sequences are low abundance nucleic acid molecules comprising one or more nucleotide base insertions, deletions, translocations, mutations, and/or damaged nucleotide bases.

11. The method of claim 10, wherein the low abundance nucleic acid molecules with one or more nucleotide base insertions, deletions, translocations, mutations and/or damaged nucleotide bases are identified and distinguished from an excess of nucleic acid molecules in the sample having a similar nucleotide sequence as the low abundance nucleic acid molecules but without the one or more nucleotide base insertions, deletions, translocations, mutations, and/or damaged bases.

12. The method of claim 1, wherein the one or more target nucleotide sequences are quantified.

13. The method of claim 1, further comprising:
diagnosing or prognosing a disease state based on said identifying.

14. The method of claim 1, further comprising:
distinguishing a genotype or disease predisposition based on said identifying.

* * * * *